(12) United States Patent
Jones, II et al.

(10) Patent No.: US 7,816,544 B2
(45) Date of Patent: Oct. 19, 2010

(54) SYNTHESIS OF ROCAGLAMIDE NATURAL PRODUCTS VIA PHOTOCHEMICAL GENERATION OF OXIDOPYRYLIUM SPECIES

(75) Inventors: Guilford Jones, II, Waltham, MA (US); Baudouin Gerard, Cambridge, MA (US); John A. Porco, Jr., Jamaica Plain, MA (US)

(73) Assignee: Trustees of Boston University, Boston, MA (US)

( * ) Notice: Subject to any disclaimer, the term of this patent is extended or adjusted under 35 U.S.C. 154(b) by 315 days.

(21) Appl. No.: 10/593,502

(22) PCT Filed: Mar. 23, 2005

(86) PCT No.: PCT/US2005/010005
§ 371 (c)(1),
(2), (4) Date: Nov. 9, 2007

(87) PCT Pub. No.: WO2005/092876
PCT Pub. Date: Oct. 6, 2005

(65) Prior Publication Data
US 2008/0177093 A1    Jul. 24, 2008

Related U.S. Application Data

(60) Provisional application No. 60/555,448, filed on Mar. 23, 2004, provisional application No. 60/612,009, filed on Sep. 22, 2004.

(51) Int. Cl.
*C07D 313/00* (2006.01)
*C07D 307/93* (2006.01)
*C07D 311/00* (2006.01)

(52) U.S. Cl. .................. 549/354; 549/458; 549/402

(58) Field of Classification Search .............. 549/355, 549/402, 458
See application file for complete search history.

(56) References Cited

U.S. PATENT DOCUMENTS

| | | | |
|---|---|---|---|
| 5,169,943 | A | 12/1992 | Lubineau et al. |
| 6,099,751 | A | 8/2000 | Meyer et al. |
| 2008/0177093 | A1 | 7/2008 | Jones et al. |
| 2009/0299081 | A1 | 12/2009 | Porco |

FOREIGN PATENT DOCUMENTS

| | | |
|---|---|---|
| WO | WO-2005/092876 | 10/2005 |
| WO | WO-2007/139749 | 12/2007 |

OTHER PUBLICATIONS

Mandel et. al. J. Phys. Chem. A 2003, 107, 6334-6339.*
Sammes et al. J. Chem. Soc. Perkin Trans. I, 1993, 1261-1265.*
Dorwald F. A. Side Reactions in Organic Synthesis, 2005, Wiley: VCH, Weinheim p. IX of Preface p. 1-15.*
Bacher et al., "Thapsakins: possible biogenetic intermediates towards insecticidal cyclopenta[b]benzofurans from *Aglaia edulis*", *Phytochemistry*, 1999, 52: 253-263.
Bader et al., "Proton transfer in 3-hydroxylavone studied by high-resolution 10 K laser-excited Shpol'skii spectroscopy", *J. Phys. Chem. A*, 2002, 106: 2844-2849.
Baer, "Oxidative Cleavage of α-Keto Acids and α-Keto Alcohols by Means of Lead Tetra-acetate", *J. Chem. Soc.*, 1940, 62: 1597-1606.
Baldwin et al., "Expedient synthesis of a highly substituted tropolone via a 3-oxidopyrylium [5+2] cycloaddition reaction", *Tetrahedron Lett.*, 2003; 44: 4543-4545.
Baumann et al., "Inducible Expression and Phosphorylation of Coactivator BOB.1/OBF.1 in T Cells", *J. Biol. Chem.*, 2002, 277: 44791-44800.
Bohnenstengel et al., "Structure activity relationships of antiproliferative rocaglamide derivatives from *Aglaia* species (Meliaceae)", *Z. Naturforsch.* [*C*], 1999, 54: 55-60.
Bohnenstengel et al., "1H-cyclopenta[b]benzofuran lignans from *Aglaia* species inhibit cell proliferation and alter cell cycle distribution in human monocytic leukemia cell lines", *Z. Naturforsch.* [*C*], 1999, 54: 1075-1083.
Chou, "The host/guest type of excited-state proton transfer: a general review", J. Chin. Chem. Soc., 2001, 48: 651-682.
Cui et al., "Novel Cytotoxic 1H-Cyclopenta[b]Benzofuran Lignans from *Aglaia elliptica*", *Tetrahedron*, 1997, 53: 17625-17632.
Crout and Rathbone, "Catalysis Di-n-butyltin Oxide of a Tertiary Ketol Rearrangement: Synthesis of Intermediates and Analogues of Valine and Isoleucine Biosynthesis", *J. Chem. Soc. Chem. Commun.*, 1987, 290-291.
Creary et al., "Diels-Alder approach to bicyclic .alpha.-hydroxy ketones. Facile ketol rearrangements of strained .alpha.-hydroxy ketones", *J. Org. Chem.*, 1985, 50: 1932-1938.
Dumontet et al., "New nitrogenous and aromatic derivatives from *Aglaia argentwa* and *A. forbesii*", *Tetrahedron*, 1996, 52: 6931-6942.
Fahrig et al., "A Synthetic Derivative of the Natural Product Rocaglaol Is a Potent Inhibitor of Cytokine-Mediated Signaling and Shows Neuroprotective Activity in Vitro and in Animal Models of Parkinson's Disease and Traumatic Brain Injury", *Mol. Pharmacol.*, 2005, 67: 1544-1555.
Gerard et al., "A Biomimetic Approach to the Rocaglamides Employing Photogeneration of Oxidopyryliums Derived from 3-Hydroxyflavones", *J. Am. Chem. Soc.*, 2004, 126: 13620-13621.

(Continued)

*Primary Examiner*—D. Margaret Seaman
*Assistant Examiner*—Nizal S Chandrakumar
(74) *Attorney, Agent, or Firm*—Brenda Herschbach Jarrell; Charles E. Lyon; Choate, Hall & Stewart LLP

(57) ABSTRACT

The present invention provides new strategies for the synthesis of compounds of the rocaglamide family and related natural products. In particular, the new biomimetic synthetic approach involves photochemical generation of an oxidopyrylium species from a 3-hydroxychromone derivative followed by 1,3-dipolar cycloaddition of the oxidopyrylium species to a dipolarophile. This approach can be used for the formation of adducts containing an aglain core structure. Methods for the conversion of aglain core structures to aglain, rocaglamide and forbaglin ring systems are also provided. The present invention also relates to the use of rocaglamide/aglain/forbaglin derivatives for the manufacture of medicaments for use in the treatment of cancer or cancerous conditions, disorders associated with cellular hyperproliferation, or NF-κB-dependent conditions.

31 Claims, 22 Drawing Sheets

OTHER PUBLICATIONS

Hailes et al., "A biomimetic approach to the synthesis of rocaglamide based on a photochemical [2+2] cycloaddition of a cinnamate unit to a flavone", *Tetrahedron Lett.*, 1993, 34: 5313-5316.

Hausott et al., "Flavaglines: A group of efficient growth inhibitors block cell cycle progression and induce apoptosis in colorectal cancer cells", *Int. J. Cancer*, 2004, 109: 933-940.

Hendrickson and Farina, "A new 7-ring cycloaddition reaction", *J. Org.Chem.*, 1980, 45: 3359-3361.

Hwang et al., "Silvestrol and Episilvestrol, Potential Anticancer Rocaglate Derivatives from *Aglaia silvestris*", *J. Org. Chem.*, 2004, 69: 3350-3358.

Itoh, "Fluorescence studies of the excited-state proton transfer in substituted 3-hydroxychromones in supersonic jet", *Pure and Applied Chemistry*, 1993, 65: 1629-1634.

Ishibashi et al., "Insecticidal 1H-Cyclopentatetrahydro[b]Benzofurans from *Aglaia odorata*", *Phytochemistry*, 1993, 32: 307-310.

Kasha, "Proton-transfer spectroscopy. Perturbation of the tautomerization potential", *J. Chem. Soc. Faraday Trans. 2*, 1986, 82: 2379-2392.

King et al., "X-Ray Crystal Structure of Rocaglamide, a Novel Antileukemic 1H-Cyclopenta[b]benzofuran from *Aglaia elliptifolia*", *J. Chem. Soc., Chem. Commun.*, 1982, 1150-1151.

Klymchenko et al., "3-Hydroxychromone dyes exhibiting excited-state intramolecular proton transfer in water with efficient two-band fluorescence", *New J. Chem.*, 2004, 28: 687-692.

Klymchenko, "Elimination of hydrogen bonding effect on solvatochromism of 3-hydroxyflavones", *J. Phys. Chem. A*, 2003, 107: 4211-4216.

Kraus and Sy, "A synthetic approach to rocaglamide via reductive cyclization of .delta.-keto nitriles", *J. Org. Chem.*, 1989, 54: 77-83.

Kumar et al., "Intramolecular excited-state proton-transfer studies on flavones in different environments", Spectrochim. Acta, Part A, 2001, 57: 299-308.

Laermer et al., "Femtosecond spectroscopy of excited-state proton transfer in 2-(2'-hydroxyphenyl)benzothiazole", *Chem. Phys. Lett.*, 1988, 148: 119-124.

Lee et al., "Cytostatic mechanism and antitumor potential of novel 1H-cyclopenta[b]benzofuran lignans isolated from *Aglaia elliptica*", *Chem. Biol. Interact.*, 1998, 115: 215-228.

Lee and Wu, "Total Synthesis of Kaempferol and Methylated Kaempferol Derivatives", *J. Chin. Chem. Soc.*, 2001, 48: 201-206.

Lui et al., "A general protocol for the hydroxylation of C-14 in gibberellins: synthesis of 14β-hydroxy-$GA_1$ methyl ester", *Tetrahedron*, 1998, 54: 11637-11650.

Mandal et al., "Evidence of ground-state proton-transfer reaction of 3-hydroxyflavone in neutral alcoholic solvents", J. Phys. Chem. A, 2003; 107: 6334-6339.

Matsuura and Takemo, "Photoinduced reactions. 61. Photorearrangement of 3-hydroxyflavones to 3-aryl-3-hydroxy-1,2-indandiones", *Tetrahedron*, 1973, 3337-3340.

Ohse et al., "Cyclopentabenzofuran Lignan Protein Synthesis Inhibitors from *Aglaia odorata*", *J. Nat. Prod.*, 1996, 650-652.

Paquette and Hofferberth, "Effect of 9,10-cyclic acetal sterochemistry on feasible operation of the alpha-ketol rearrangement in highly functionalized paclitaxel (Taxol) precursors", *J. Org. Chem.*, 2003, 68: 2266-2275.

Proksch et al., "Chemistry and biological activity of rocaglamide derivatives and related compounds in *Aglaia* species (*Meliaceae*)", *Curr. Org. Chem.*, 2001, 5: 923-938.

Piers et al., "Sequential anionic 1,3-ester shifts and intramolecular stille couplings: a new protocol for the concise assembly of functionalized polycyclic dienes", *Synlett.*, 1999, 7: 1082-1084.

Roschal et al., "Flavonols and Crown-Flavonols as Metal Cation Chelators. The Different Nature of $Ba^{2+}$ and $Mg^{2+}$ Complexes", J. Phys. Chem. A, 1998, 102: 5907-5914.

Sammes et al., "The preparation and some reactions of 3-oxidopyrylium", *J. Chem. Soc. Perkin Trans. I*, 1983, 1261-1265.

Schwartz et al., "Direct observation of fast proton transfer: femtosecond photophysics of 3-hydroxyflavone", *J. Phys. Chem.*, 1992, 96: 3591-3598.

Shipman et al., "Synthesis of 1,3,2-dioxathiolane-4-methylene-2-oxides: Potential allene oxide equivalents", *Tetrahedron*, 1999, 55: 10845-10850.

Tamaki et al., "Syntheses of (−)-(7S)- and (+)-(7R)-K252a dimers", *Tetrahedron Lett.*, 2002, 43: 379-382.

Tanaka et al., "Synthesis of flavonol derivatives as probes of biological processes", *Tetrahedron Lett.*, 2000, 41: 9735-9739.

Trost et al., "An unusual oxidative cyclization. A synthesis and absolute stereochemical assignment of (−)-rocaglamide", *J. Am. Chem. Soc.*, 1990, 112: 9022-9024.

Wender et al., "The First Synthesis of a Daphnane Diterpene: The Enantiocontrolled Total Synthesis of (+)-Resiniferatoxin", *J. Am. Chem. Soc.*, 1997, 119: 12976-12977.

Wu et al., "Cytotoxic and antiplatelet aggregation principles from *Aglaia elliptifolia*", *J. Nat. Prod.*, 1997, 60: 606-608.

U.S. Appl. No. 60/802,560, filed May 22, 2006, Porco.
U.S. Appl. No. 60/555,448, filed Mar. 23, 2004, Porco et al.
U.S. Appl. No. 60/612,009, filed Sep. 22, 2004, Porco et al.

Adembri et al., "Influence of the solvent on the stereoselectivity of 1,3-dipolar cycloaddition of nitrile oxides on several 4-substituted 2-cyclopentenones," *J. Chem. Res.* 2003(3):126-127 (2003).

Altava et al., "On the origin of changes in topicity observed in Diels-Alder reactions catalyzed by Ti-TADDOLates," *Tetrahedron: Asymmetry* 11(24):4885-4893 (2000).

Bader et al., "Proton transfer in 3-hydroxylavone studied by high-resolution 10 K laser-excited Shpol'skii spectroscopy," *J. Phys. Chem. A.* 106:2844-2849 (2002).

Bauer et al., "Catalytic enantioselective reactions driven by photoinduced electron transfer," *Nature* 436:1139-1140 (2005).

Beck et al., "Grossansätze zur Herstellung von α,α,α¹,α¹-Tetraaryl-1,3-dioxolan-4,5-dimethanolen (TADDOLe): Nützliche Hilfsstoffe für die EPC-Synthese und ihre Struktur im Festkörper," *Chimia* 45:238-244 (1991).

Bhasker Gondi et al., "Hydrogen Bond Catalyzed Enantioselective Vinylogous Mukaiyama Aldol Reaction,"*Org. Lett.* 7(25):5657-5660 (2005).

Brader et al., "Bisamides, lignans, triterpenes, and insecticidal Cyclopenta[b]benzofurans from *Aglaia* species," *J. Nat. Prod.* 61:1482-1490 (1998).

Burke, "Targeting IkappaB kinase for the treatment of inflammatory and other disorders," *Curr. Opin. Drug Discov. Devel.* 6:720-728 (2003).

Chaidir et al., "New Insecticidal Rocaglamide Derivatives from Flowers of *Aglaia duperreana* (*Meliaceae*),"*Phytochemistry* 52:837-842 (1999).

Cuenca et al., "Highly enantioselective protonation of the 3,4-dihydro-2-methylnaphthalen-1(2H)-one Li-enolate by TADDOLs," *Helv. Chim. Acta* 83:3153-3162 (2000).

Cui et al., "Novel Cytotoxic 1H-Cyclopenta[b]Benzofuran Lignans from *Aglaia elliptica*," *Tetrahedron* 53:17625-17632 (1997).

Das et al., "A critical role for NF-kappa B in GATA3 expression and TH2 differentiation in allergic airway inflammation," *Nature Immunol.* 2:45-50 (2001).

Demchenko, "Elimination of the Hydrogen Bonding Effect on the Solvatochromism of 3-Hydrxyflavones" *J. Phys. Chem. A* 107:4211-4216 (2003).

Diedrichs et al., "A Highly Efficient Synthesis of Rocaglaols by a Novel α-Arylation of Ketones," *Eur J. Org. Chem.* 9:1731-1735 (2005).

Dumontet et al., "New nitrogenous and aromatic derivatives from *Aglaia argentwa* and *A. forbesii*," *Tetrahedron* 52: 6931-6942 (1996).

Gagliardo et al., "Persistent Activation of Nuclear Factor-{kappa}B Signaling Pathway in Severe Uncontrolled Asthma," *Am. J. Respir. Crit. Care Med.* 168:1190-1198 (2003).

Garg and Aggarwal, "Nuclear transcription factor-κB as a target for cancer drug development," *Leukemia* 16:1053-1056 (2002).

Gerard et al., "A Biomimetic Approach to the Rocaglamides Employing Photogeneration of Oxidopyryliums Derived from 3-Hydroxyflavones," *J. Am. Chem. Soc.* 126:13620-13621 (2004).

Gerard et al., "Enantioselective Photocycloaddition Mediated by Chiral Brønsted Acids: Asymmetric Synthesis of the Rocaglamides," *J. Am. Chem. Soc.* 128:7754-7755 (2006).

Le Gourrierecet al., "Excited State Intramolecular Proton Transfer Part 2: ESIPT to Oxygen" *Prog. React. Kinet.* 19:211-275 (1994).

Greene et al., "Decarbalkoxylation of [beta]-keto esters-a new mild procedure," *Tetrahedron Lett.* 2707-2708 (1976).

Grosch et al., "Highly Enantioselective Diels-Alder Reactions of a Photochemically Generated o-Quinodimethane and Olefins," *Angew. Chem., Int. Ed.*, 42:3693-3696 (2003).

Gussregen et al., "Insecticidal rocaglamide derivatives from *Aglaia duppereana*," *Phytochemistry* 44:1455-1461 (1997).

Hailes et al., "A biomimetic approach to the synthesis of rocaglamide based on a photochemical [2+2] cycloaddition of a cinnamate unit to a flavone," *Tetrahedron Lett.*, 34:5313-5316 (1993).

Huang et al., "Tumor necrosis factor modulates transcription of myelin basic protein gene through nuclear factor kappa B in a human oligodendroglioma cell line," *Int. J. Dev. Neurosci.* 20:289-296 (2002).

International Search Report for PCT/US2007/012062, mailed Aug. 5, 2008.

International Search Report for PCT/US2005/010005, mailed Sep. 6, 2005.

Irurre et al., "Synthesis and structure of (4R,5R)-à,à,à',à'-2,2-hexaphenyl-4,5-dimethanol-1,3-dioxolane," *Tetrahedron: Asymmetry* 3:1591-1596 (1992).

Ito et al., "Preparation and structural analysis of several new alpha, alpha, alpha'-tetraaryl-1, 3-dioxolane-4, 5-dimethanols (taddols) and taddol analogs, their evaluation as titanium ligands in the enantioselective addition of methyltitanium and diethylzinc reagent," *Helvetica Chim. Acta* 77:2071-2110 (1994).

Jacobsen, "Highly Enantioselective Thiourea-Catalyzed Nitro-Mannich Reactions" *Angew. Chem., Int. Ed.* 44:466-468 (2005).

Jones et al, "NF-κB as an integrator of diverse signaling pathways," *Cardiovasc. Toxicol.* 3:229-254 (2003).

Kaltschmidt et al., "Transcription factor NF-κB is activated in primary neurons by amyloid β peptides and in neurons surrounding early plaques from patients with Alzheimer disease," *Proc. Natl. Acad. Sci. USA* 94:2642-2647 (1997).

Krishna, et al., "Studies towards the synthesis of FCRR toxin: an expedition entry into 7-5-6 ring systems via [5+2] oxidopyrylium-alkene cycloaddition." *Tetrahedron Lett.*, 45 (5) (2004).

Lei et al., "Total synthesis of the ubiquitin-activating enzyme inhibitor (+)-panepophenanthrin," *Angew. Chem., Int. Ed.* 42:3913-3917 (2003).

Legrand et al., "Synthesis, NMR conformational studies and host-guest behaviour of new (+)-tartaric acid derivatives," *Tetrahedron: Asymmetry* 16:635-640 (2005).

Lin et al., "NF-κB in cancer: a marked target," *Semin. Cancer Biol.* 13:107-114 (2003).

Liu et al., "A general protocol for the hydroxylation of C-14 in gibberellins: synthesis of 14β-hydroxy-GA$_1$ methyl ester," *Tetrahedron* 54:11637-11650 (1998).

Mattson et al., "NF-kappaB in neuronal plasticity and neurodegenerative disorders," *J. Clin. Invest.* 107:247-254 (2001).

McDougal et al., "Asymmetric Morita-Baylis-Hillman Reactions Catalyzed by Chiral Brønsted Acids," *J. Am. Chem. Soc.* 125:12094-12095 (2003).

Nugent et al., "Chiral Proton Catalysis: A Catalytic Enantioselective Direct Aza-Henry Reaction," *J. Am. Chem. Soc.* 126:3418-3419 (2004).

Nugroho et al., "Insecticidal Rocaglamide Derivatives from *Aglaia elliptica* and *A. harmisiana*," *Phytochemistry* 45:1579-1585 (1997).

Nugroho et al., "An Insecticidal Rocaglamide Derivatives and Related Compounds from *Aglaia odorata* (*Meliaceae*)," *Phytochemistry* 51:367-376 (1999).

Orlowski et al., "NF-κB as a therapeutic target in cancer," *Trends Mol. Med.* 8:385-389 (2002).

Paquette et al., "The α-Hydroxy Ketone (α-Ketol) and Related Rearrangements" *Org. React.* 62: 477-567 (2003).

Proksch et al., "Chemistry and biological activity of rocaglamide derivatives and related compounds in *Aglaia* species (*Meliaceae*)," *Curr. Org. Chem.* 5:923-938 (2001).

Quadrelli et al., "Intra- and Intermolecular Hydrogen Bonding Effects in Cycloadditions between Nitrile Oxides and 4-Benzoylamino-2-cyclopenten-1-ol and Its Derivatives," *Eur. J. Org. Chem.* 13:2058-2065 (2002).

Rastogi et al., "Intramolecular excited-state proton-transfer studies on flavones in different environments," *Spectrochim. Acta, Part A* 57:299-308 (2001).

Rentzea et al., "α-ketol-umlagerung von myrsinol zum iso-myrsinol and mögliche biogenese des myrsinan-derüstes," *Tetrahedron Lett.* 23:1785-1788 (1982).

Roshak et al., "Small-molecule inhibitors of NF-κB for the treatment of inflammatory joint disease," *Curr. Opin. Pharmacol.* 2:316-321 (2002).

Roshal et al., "Flavonols and Crown-Flavonols as Metal Cation Chelators. The Different Nature of $Ba^2$ and $Mg^{2+}$ Complexes" *J. Phys. Chem.* 102:5907-5914 (1998).

Samanta et al., "Evidence of Ground-State Proton Transfer Reaction of 3-Hydroxyflavone in Neutral Alcoholic Solvents" *J. Phys. Chem. A* 107:6334-6339 (2003).

Seebach et al., "On the Ti-TADDOLate-Catalyzed Diels-Alder Addition of 3-Butenoyl-1,3-Oxazolidin-2-One to Cyclopentadiene. General Features of Ti-BINOLate- and Ti-TADDOLate-Mediated Reactions," *J. Org. Chem.* 60:1788 (1995).

Seebach et al., "Mixed β-Peptides: A unique helical secondary structure in solution. Preliminary communication," *Helv. Chim. Acta* 80:2033-2038 (1997).

Seebach et al., "TADDOLs, Their Derivatives, and TADDOL Analogues: Versatile Chiral Auxiliaries," *Angew. Chem. Int. Ed.* 40:92-138 (2001).

Shoelson et al., "Inflammation and the IKK beta/I κβ/NF-κβ axis in obesity- and diet-induced insulin resistance," *Int. J. Obes. Relat. Metab. Disord.* 27 (Supp. 3):S49-S52 (2003).

Tanaka et al., "Enantioselective [2+2] photodimerization reactions of coumarins in solution," *Org. Lett.* 7:1501-1503 (2005).

Taylor et al., "Asymmetric Catalysis by Chiral Hydrogen-Bond Donors" *Angew. Chem., Int. Ed.* 45:1520-1543 (2006).

Thadani et al., "Enantioselective Diels—Alder reactions catalyzed by hydrogen bonding," *Proc. Natl. Acad. Sci. U.S.A.* 101:5846-5850 (2004).

Valen et al., "Nuclear factor kappa-B and the heart," *J. Am. Coll. Cardiol.* 38:307-314 (2001).

Van Heel et al., "Inflammatory bowel disease is associated with a TNF polymorphism that affects an interaction between the OCT1 and NF-κB transcription factors," *Hum. Mol. Genet.* 11:1281-1289 (2002).

Wessig, "Organocatalytic Enantioselective Photoreactions" *Angew. Chem., Int. Ed.* 45:2168-2171 (2006).

Yamamoto et al., "Bronsted Acid Catalysis of Achiral Enamine for Regio- and Enantioselective Nitroso Aldol Synthesis" *J. Am. Chem. Soc.* 127:1080-1081 (2005).

Yamamoto et al., "Role of the NF-κB Pathway in the Pathogenesis of Human Disease States," *Curr. Mol., Med.* 1:287-296 (2001).

Yamamoto et al., "Therapeutic potential of inhibition of the NF-κB pathway in the treatment of inflammation and cancer" *J. Clin. Invest.* 107:135-142 (2001).

Yang et al., "Essential Role of Nuclear Factor κB in the Induction of Eosinophilia in Allergic Airway Inflammation" *J. Exp. Med.* 188:1739-1750 (1998).

\* cited by examiner

US 7,816,544 B2

SYNTHESIS OF ROCAGLAMIDE NATURAL PRODUCTS VIA PHOTOCHEMICAL GENERATION OF OXIDOPYRYLIUM SPECIES

RELATED APPLICATIONS

This application is a U.S. National Phase Application under 35 U.S.C §371 of International Application PCT/US2005/10005 (published PCT application No. WO 2005/092876) filed Mar. 23, 2005, which claims priority from Provisional Application No. 60/555,448, filed on Mar. 23, 2004 and entitled "Synthesis of the Aglain Skeleton by Photogeneration and Dipolar Cycloaddition of Oxidopyryliums Derived from 2-Hydroxyflavones", and Provisional Application No. 60/612,009 filed on Sep. 22, 2004 and entitled "Synthesis of Rocaglamide Natural Products via Photochemical Generation of Oxidopyrylium Species". Each of the above-cited patent applications is incorporated herein by reference in its entirety.

BACKGROUND OF THE INVENTION

The plant genus *Aglaia* native of the tropical rain forests of Indonesia and Malaysia is the source of a unique group of densely functionalized natural products presented on FIG. 1 (P. Proksch et al., Curr. Org. Chem., 2001, 5: 923-938). The rocaglamides, including the parent molecule (compound 1; M. L. King et al., J. Chem. Soc., Chem. Commun., 1982, 1150-1151) and the recently isolated dioxanyloxy-modified derivative silvestrol (compound 2; B. Y. Hwang et al., J. Org. Chem., 2004, 69: 3350-3358), possess a cyclopenta[b]tetrahydrobenzofuran ring system (presented in red on FIG. 1). The structurally related aglains (e.g., compounds 3 and 4), which contain a cyclopenta[bc]benzopyran structure (presented in blue on FIG. 1), have also been isolated from *Aglaia* (V. Dumontet et al., Tetrahedron, 1996, 52: 6931-6942). The forbaglins (e.g., compound 5) are benzo[b]oxepines (in green on FIG. 1) derived from formal oxidative cleavage of the aglain core.

The rocaglamides have been shown to exhibit potent anticancer (M. L. King et al., J. Chem. Soc., Chem. Commun., 1982, 1150-1151) and antileukemic activity (S. K. Lee et al., Chem. Biol. Interact., 1998, 115: 215-228), as well as NF-κB inhibitory activity at nanomolar concentrations in human T cells (B. Baumann et al., J. Biol. Chem., 2002, 277: 44791-44800). The rocaglate silvestrol 2 displays cytotoxic activity against human cancer cells comparable to the anticancer drug Taxol (B. Y. Hwang et al., J. Org. Chem., 2004, 69: 3350-3358).

As proposed by Proksch (P. Proksch et al., Curr. Org. Chem., 2001, 5: 923-938) and Bacher (M. Bacher et al., Phytochemistry, 1999, 52: 253-263), and as shown on FIG. 2, the rocaglamides may be biosynthetically derived from reaction of trimethoxy-substituted 3-hydroxyflavone with cinnamide derivatives to afford the aglain core followed by skeletal rearrangement.

Although the rocaglamides have been the subject of a number of synthetic investigations (see, for example, G. A. Kraus and J. O, Sy, J. Org. Chem., 1989, 54: 77-83; B. Trost et al., J. Am. Chem. Soc., 1990, 112: 9022-9024), including a biomimetic approach involving a [2+2] photocycloaddition (H. C. Hailes et al., Tetrahedron Lett., 1993, 34: 5313-5316), syntheses of the related aglain (V. Dumontet et al., Tetrahedron, 1996, 52: 6931-6942), aglaforbesin (V. Dumontet et al., Tetrahedron, 1996, 52: 6931-6942), or forbaglins have not been reported. Moreover, a unified synthetic approach to these molecules based on biosynthetic considerations still remains to be developed.

SUMMARY OF THE INVENTION

The present invention provides new methods for the synthesis of natural products. In particular, the invention encompasses novel strategies for the biomimetic preparation of compounds in the rocaglamide/aglain/forbaglin family.

More specifically, one aspect of the present invention relates to the use of a photochemically generated oxidopyrylium species as an intermediate in a chemical reaction. In certain preferred embodiments, the photochemical reaction leading to the formation of the oxidopyrylium species comprises an excited state intramolecular proton transfer.

For example, the oxidopyrylium species may be produced by photochemical irradiation of a 3-hydroxychromone derivative (I) with the following chemical structure:

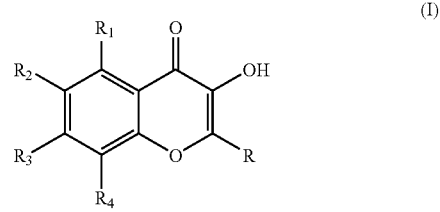

wherein $R_1$, $R_2$, $R_3$, $R_4$ and R are identical or different and selected from the group consisting of hydrogen, halogen, hydroxy, alkoxy, aryloxy, heteroalkoxy, heteroaryloxy, thioalkyl, thioaryl, acyl, aliphatic, alicyclic, heteroaliphatic, heterocyclic, aromatic, heteroaromatic, aryl, heteroaryl, alkylamino, amino alkyl, arylamino, amino aryl, a protecting group, —$NO_2$, —CN, —$CF_3$, —$CH_2CF_3$, —$CHCl_2$, —$CH_2OH$, —$CH_2CH_2OH$, —$CH_2SO_2CH_3$, —C(=O)$R_x$, —$CO_2(R_x)$, —C(=O)N($R_x$)$_2$, —OC(=O)N($R_x$)$_2$, —OC(=O)$R_x$, —$OCO_2R_x$, —S(O)$R_x$, —S(O)$_2R_x$, —$NR_x$(CO)$R_x$, —N($R_x$)$CO_2R_x$, —N($R_x$)C(=O)N($R_x$)$_2$, —N($R_x$)S(O)$_2R_x$, and —S(O)$_2$N($R_x$)$_2$, wherein each occurrence of $R_x$ is independently selected from the group consisting of hydrogen, aliphatic, alicyclic, heteroaliphatic, heterocyclic, aromatic, heteroaromatic, aryl, and heteroaryl.

In particular, the oxidopyrylium species may be produced by photochemical irradiation of a 3-hydroxyflavone derivative (II) with the following chemical structure:

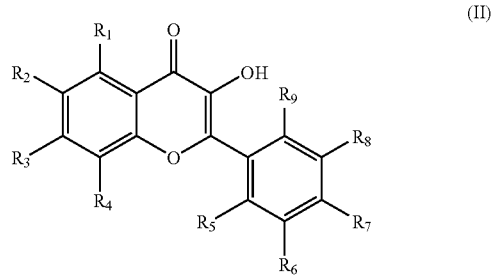

wherein $R_1$, $R_2$, $R_3$, $R_4$, $R_5$, $R_6$, $R_7$, $R_8$ and $R_9$ are identical or different and selected from the group consisting of hydrogen, halogen, hydro y, alkoxy, aryloxy, heteroalkoxy, heteroaryloxy, thioalkyl, thioaryl, acyl, aliphatic, alicyclic, heteroaliphatic, heterocyclic, aromatic, heteroaromatic, aryl, heteroaryl, alkylamino, amino alkyl, arylamino, amino aryl, a protecting group, —NO$_2$, —CN, —CF$_3$, —CH$_2$CF$_3$, —CHCl$_2$, —CH$_2$OH, —CH$_2$CH$_2$OH, —CH$_2$SO$_2$CH$_3$, —C(=O)R$_x$, —CO$_2$(R$_x$), —C(=O)N(R$_x$)$_2$, —OC(=O)N(R$_x$)$_2$, —OC(=O)R$_x$, —OCO$_2$R$_x$, —S(O)R$_x$, —S(O)$_2$R$_x$, —NR$_x$(CO)R$_x$, —N(R$_x$)CO$_2$R$_x$, —N(R$_x$)C(=O)N(R)$_2$, —N(R$_x$)S(O)$_2$R$_x$, and —S(O)$_2$N(R$_x$)$_2$, wherein each occurrence of R$_x$ is independently selected from the group consisting of hydrogen, aliphatic, alicyclic, heteroaliphatic, heterocyclic, aromatic, heteroaromatic, aryl, and heteroaryl. In certain preferred embodiments, the 3-hydroxyflavone derivative has one of the following chemical structures:

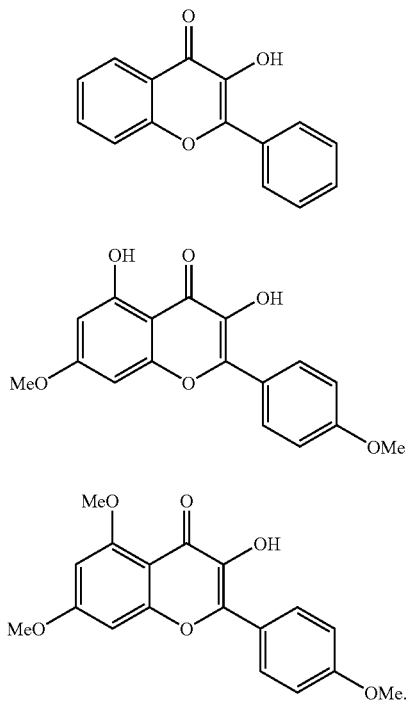

Alternatively, the oxidopyrylium species may be produced by photochemical irradiation of a 5-hydroxy-2,3-dihydro-pyran-4-one derivative (III) with the following chemical structure:

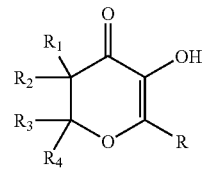

(III)

wherein R$_1$, R$_2$, R$_3$, R$_4$ and R are identical or different and selected from the group consisting of hydrogen, halogen, hydroxy, alkoxy, aryloxy, heteroalkoxy, heteroaryloxy, thioalkyl, thioaryl, acyl, aliphatic, alicyclic, heteroaliphatic, heterocyclic, aromatic, heteroaromatic, aryl, heteroaryl, alkylamino, amino alkyl, arylamino, amino aryl, a protecting group, —NO$_2$, —CN, —CF$_3$, —CH$_2$CF$_3$, —CHCl$_2$, —CH$_2$OH, —CH$_2$CH$_2$OH, —CH$_2$SO$_2$CH$_3$, —C(=O)R$_x$, —CO$_2$(R$_x$), —C(=O)N(R$_x$)$_2$, —OC(=O)N(R$_x$)$_2$, —OC(=O)R$_x$, —OCO$_2$R$_x$, —S(O)R$_x$, —S(O)$_2$R$_x$, —NR$_x$(CO)R$_x$, —N(R$_x$)CO$_2$R$_x$, —N(R$_x$)C(=O)N(R$_x$)$_2$, —N(R$_x$)S(O)$_2$R$_x$, and —S(O)$_2$N(R$_x$)$_2$, wherein each occurrence of R$_x$ is independently selected from the group consisting of hydrogen, aliphatic, alicyclic, heteroaliphatic, heterocyclic, aromatic, heteroaromatic, aryl, and heteroaryl.

In certain embodiments, the photochemically generated oxidopyrylium species is used as an intermediate in a cycloaddition, for example a 1,3-dipolar cycloaddition, leading to the formation of an adduct.

Another aspect of the present invention relates to a method comprising steps of: photochemically generating an oxidopyrylium species; and reacting the oxidopyrylium species thus obtained with a dipolarophile. In certain preferred embodiments, the oxidopyrylium species is produced by photoinduced excited state intramolecular proton transfer of a 3-hydroxychromone derivative of chemical structure (I), or a 3-hydroxyflavone derivative of chemical structure (II) or a 5-hydroxy-2,3-dihydro-pyran-4-one derivative of chemical structure (III), as described above.

In certain embodiments, the reaction between the oxidopyrylium species and the dipolarophile (e.g., a cinnamate derivative) comprises a cycloaddition, (e.g., a 1,3-dipolar cycloaddition), and results in the formation of an adduct. Preferably, the adduct comprises an aglain core structure. In other embodiments, the inventive method further comprises converting the adduct formed. For example, when the adduct formed comprises an aglain core structure, converting the adduct may result in the formation of a ring system selected from the group consisting of an aglain ring system, a rocaglamide ring system, and a forbaglin ring system.

In another aspect, the present invention provides a method for preparing a compound containing an aglain core structure, said method comprising steps of: producing an oxidopyrylium species (I$_T$) by photoinduced excited state intramolecular proton transfer of a 3-hydroxychromone derivative (I); and reacting the oxidopyrylium species with a dipolarophile (IV) to obtain the aglain core-containing compound (V). Compounds (I), (I$_T$), (IV), and (V) have the following chemical structures:

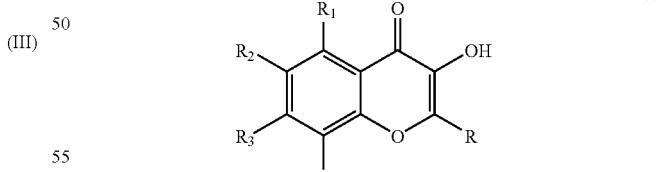

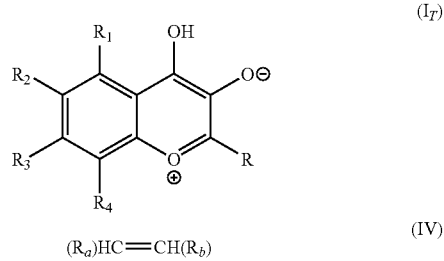

-continued (V)

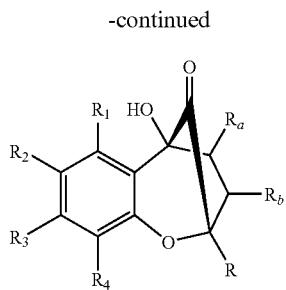

wherein $R_1$, $R_2$, $R_3$, $R_4$, R, $R_a$ and $R_b$ are identical or different and selected from the group consisting of hydrogen, halogen, hydroxy, alkoxy, aryloxy, heteroalkoxy, heteroaryloxy, thioalkyl, thioaryl, acyl, aliphatic, alicyclic, heteroaliphatic, heterocyclic, aromatic, heteroaromatic, aryl, heteroaryl, alkylamino, amino alkyl, arylamino, amino aryl, a protecting group, —$NO_2$, —CN, —$CF_3$, —$CH_2CF_3$, —$CHCl_2$, —$CH_2OH$, —$CH_2CH_2OH$, —$CH_2SO_2CH_3$, —C(=O)$R_x$, —$CO_2(R_x)$, —C(=O)N($R_x$)$_2$, —OC(=O)N($R_x$)$_2$, —OC(=O)$R_x$, —$OCO_2R_x$, —S(O)$R_x$, —S(O)$_2R_x$, —N$R_x$(CO)$R_x$, —N($R_x$)$CO_2R_x$, —N($R_x$)C(=O)N($R_x$)$_2$, —N($R_x$)S(O)$_2R_x$, and —S(O)$_2$N($R_x$)$_2$, wherein each occurrence of $R_1$ is independently selected from the group consisting of hydrogen, aliphatic, alicyclic, heteroaliphatic, heterocyclic, aromatic, heteroaromatic, aryl, and heteroaryl.

Alternatively, the method for preparing a compound containing an *aglain* core structure may comprising steps of: producing an oxidopyrylium species (II$_T$) by photoinduced excited state intramolecular proton transfer of a 3-hydroxy-flavone derivative (II); and reacting the oxidopyrylium species with a dipolarophile (IV) to obtain the aglain core-containing compound (V'). Compounds (II), (II$_T$), (IV), and (V') have the following chemical structures:

(II)

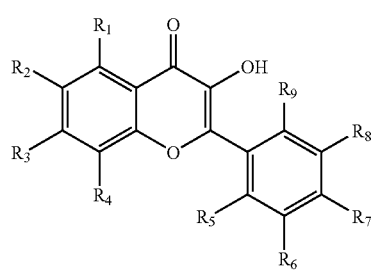

(II$_T$)

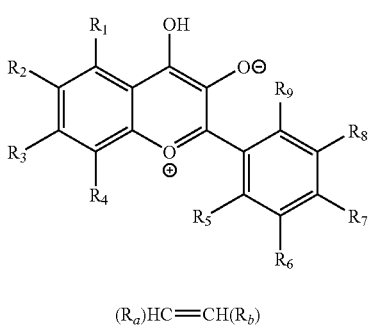

($R_a$)HC=CH($R_b$)   (IV)

-continued (V')

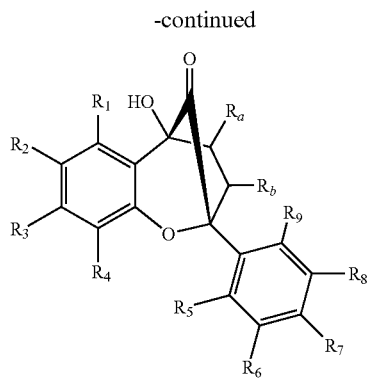

wherein $R_1$, $R_2$, $R_3$, $R_4$, $R_5$, $R_6$, $R_7$, $R_8$, $R_9$, $R_a$ and $R_b$ are identical or different and selected from the group consisting of hydrogen, halogen, hydroxy, alkoxy, aryloxy, heteroalkoxy, heteroaryloxy, thioalkyl, thioaryl, acyl, aliphatic, alicyclic, heteroaliphatic, heterocyclic, aromatic, heteroaromatic, aryl, heteroaryl, alkylamino, amino alkyl, arylamino, amino aryl, a protecting group, —$NO_2$, —CN, —$CF_3$, —$CH_2CF_3$, —$CHCl_2$, —$CH_2OH$, —$CH_2CH_2OH$, —$CH_2SO_2CH_3$, —C(=O)$R_x$, —$CO_2(R_x)$, —C(=O)N($R_x$)$_2$, —OC(=O)N($R_x$)$_2$, —OC(=O)$R_x$, —$OCO_2R_x$, —S(O)$R_x$, —S(O)$_2R_x$, —N$R_x$(CO)$R_x$, —N($R_x$)$CO_2R_x$, —N($R_x$)C(=O)N($R_x$)$_2$, —N($R_x$)S(O)$_2R_x$, and —S(O)$_2$N($R_x$)$_2$, wherein each occurrence of $R_1$ is independently selected from the group consisting of hydrogen, aliphatic, alicyclic, heteroaliphatic, heterocyclic, aromatic, heteroaromatic, aryl, and heteroaryl.

In certain preferred embodiments of these methods, the dipolarophile (IV) is a cinnamate derivative with the following chemical structure:

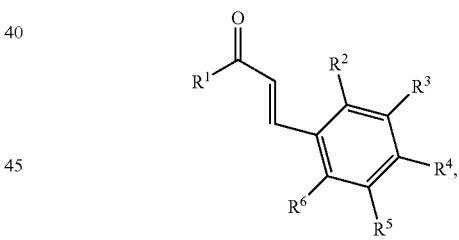

wherein $R^1$ is selected from the group consisting of hydrogen, hydroxy, alkoxy, aryloxy, heteroalkoxy, heteroaryloxy, acyl, aliphatic, alicyclic, heteroaliphatic, heterocyclic, aromatic, heteroaromatic, aryl, heteroaryl, alkylamino, amino alkyl, arylamino, amino aryl, and a protecting group; and wherein $R^2$, $R^3$, $R^4$, $R^5$, and $R^6$ are identical or different and selected from the group consisting of hydrogen, halogen, hydroxy, alkoxy, aryloxy, heteroalkoxy, heteroaryloxy, thioalkyl, thioaryl, acyl, aliphatic, alicyclic, heteroaliphatic, heterocyclic, aromatic, heteroaromatic, aryl, heteroaryl, alkylamino, amino alkyl, arylamino, amino aryl, a protecting group, —$NO_2$, —CN, —$CF_3$, —$CH_2CF_3$, —$CHCl_2$, —$CH_2OH$, —$CH_2CH_2OH$, —$CH_2SO_2CH_3$, —C(=O)$R_x$, —$CO_2(R_x)$, —C(=O)N($R_x$)$_2$, —OC(=O)N($R_x$)$_2$, —OC(=O)$R_x$, —$OCO_2R_x$, —S(O)$R_x$, —S(O)$_2R_x$, —N$R_x$(CO)$R_x$, —N($R_x$)$CO_2R_x$, —N($R_x$)C(=O)N($R_x$)$_2$, —N($R_x$)S(O)$_2R_x$, and —S(O)$_2$N($R_x$)$_2$, wherein each occurrence of $R_x$ is independently selected from the group consisting of hydrogen, aliphatic, alicyclic, heteroaliphatic, heterocyclic, aromatic, heteroaromatic, aryl, and heteroaryl.

In certain embodiments, the inventive methods further comprise converting the compound with an aglain core structure obtained. For example, the aglain core-containing compound may be converted into a compound with a ring system selected from the group consisting of an aglain ring system, a rocaglamide ring system, and a forbaglin ring system. Conversion into a compound with an aglain ring system may involve a reduction. Conversion into a compound with a rocaglamide ring system may comprise an α-ketol (acyloin) rearrangement (preferably under basic conditions), and optionally a hydroxyl-directed reduction. Conversion into a compound with a forbaglin ring system may comprise an oxidative cleavage.

In another aspect, the present invention relates to a method for preparing an aglain derivative, the method comprising steps of: producing an oxidopyrylium species ($I_T$) by photo-induced excited state intramolecular proton transfer of a 3-hydroxychromone derivative (I); reacting the oxidopyrylium species with a dipolarophile (IV) to obtain a compound with an aglain core structure (V); and converting the compound with the aglain core structure into an aglain derivative (VI). Compounds (I), ($I_T$), (IV), and (V) are as described above and compound (VI) has the following chemical structure:

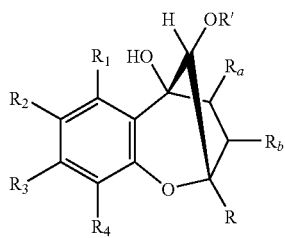

(VI)

wherein $R_1$, $R_2$, $R_3$, $R_4$, R, $R_a$ and $R_b$ are identical or different and selected from the group consisting of hydrogen, halogen, hydroxy, alkoxy, aryloxy, heteroalkoxy, heteroaryloxy, thioalkyl, thioaryl, acyl, aliphatic, alicyclic, heteroaliphatic, heterocyclic, aromatic, heteroaromatic, aryl, heteroaryl, alkylamino, amino alkyl, arylamino, amino aryl, a protecting group, —NO$_2$, —CN, —CF$_3$, —CH$_2$CF$_3$, —CHCl$_2$, —CH$_2$OH, —CH$_2$CH$_2$OH, —CH$_2$SO$_2$CH$_3$, —C(=O)R$_x$, —CO$_2$(R$_x$), —C(=O)N(R$_x$)$_2$, —OC(=O)N(R$_x$)$_2$, —OC(=O)R$_x$, —OCO$_2$R$_x$, —S(O)R$_x$, —S(O)$_2$R$_x$, —NR$_x$(CO)R$_x$, —N(R$_x$)CO$_2$R$_x$, —N(R$_x$)C(=O)N(R$_x$)$_2$, —N(R$_x$)S(O)$_2$R$_x$, and —S(O)$_2$N(R$_x$)$_2$, wherein each occurrence of R$_x$ is independently selected from the group consisting of hydrogen, aliphatic, alicyclic, heteroaliphatic, heterocyclic, aromatic, heteroaromatic, aryl, and heteroaryl; and wherein R' is selected from the group consisting of hydrogen, alkoxy, aryloxy, heteroalkoxy, heteroaryloxy, acyl, aliphatic, alicyclic, heteroaliphatic, heterocyclic, aromatic, heteroaromatic, aryl, heteroaryl, alkylamino, amino alkyl, arylamino, amino aryl, a protecting group, —CH$_2$OH, —CH$_2$CH$_2$OH, —CH$_2$SO$_2$CH$_3$, —C(=O)R$_x$, —CO$_2$(R$_x$), —C(=O)N(R$_x$)$_2$, —S(O)R$_x$, —NR$_x$(CO)R$_x$, —N(R$_x$)CO$_2$R$_x$, —N(R$_x$)C(=O)N(R$_x$)$_2$, and —N(R$_x$)S(O)$_2$R$_x$, wherein each occurrence of R$_x$ is independently selected from the group consisting of hydrogen, aliphatic, alicyclic, heteroaliphatic, heterocyclic, aromatic, heteroaromatic, aryl, and heteroaryl.

Alternatively, the method for preparing an aglain derivative comprises steps of: producing an oxidopyrylium species (II$_T$) by photoinduced excited state intramolecular proton transfer of a 3-hydroxyflavone derivative (II); reacting the oxidopyrylium species with a dipolarophile (IV) to obtain a compound with an aglain core structure (V'); and converting the compound with an aglain core structure into an aglain derivative (VI'). Compounds (II), (II$_T$), (IV), and (V') are as described above and compound (VI') has the following chemical structure:

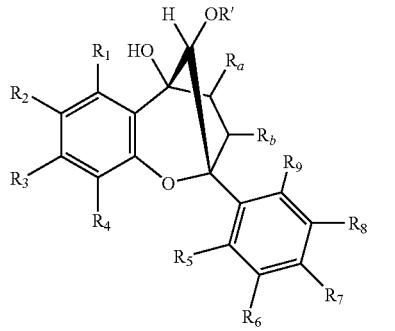

(VI')

wherein $R_1$, $R_2$, $R_3$, $R_4$, $R_5$, $R_6$, $R_7$, $R_8$, $R_9$, $R_a$ and $R_b$ are identical or different and selected from the group consisting of hydrogen, halogen, hydroxy, alkoxy, aryloxy, heteroalkoxy, heteroaryloxy, thioalkyl, thioaryl, acyl, aliphatic, alicyclic, heteroaliphatic, heterocyclic, aromatic, heteroaromatic, aryl, heteroaryl, alkylamino, amino alkyl, arylamino, amino aryl, a protecting group, —NO$_2$, —CN, —CF$_3$, —CH$_2$CF$_3$, —CHCl$_2$, —CH$_2$OH, —CH$_2$CH$_2$OH, —CH$_2$SO$_2$CH$_3$, —C(=O)R$_x$, —CO$_2$(R$_x$), —C(=O)N(R$_x$)$_2$, —OC(=O)N(R$_x$)$_2$, —OC(=O)R$_x$, —OCO$_2$R$_x$, —S(O)R$_x$, —S(O)$_2$R$_x$, —NR$_x$(CO)R$_x$, —N(R$_x$)CO$_2$R$_x$, —N(R$_x$)C(=O)N(R$_x$)$_2$, —N(R$_x$)S(O)$_2$R$_x$, and —S(O)$_2$N(R$_x$)$_2$, wherein each occurrence of R$_x$ is independently selected from the group consisting of hydrogen, aliphatic, alicyclic, heteroaliphatic, heterocyclic, aromatic, heteroaromatic, aryl, and heteroaryl; and wherein R' is selected from the group consisting of hydrogen, alkoxy, aryloxy, heteroalkoxy, heteroaryloxy, acyl, aliphatic, alicyclic, heteroaliphatic, heterocyclic, aromatic, heteroaromatic, aryl, heteroaryl, alkylamino, amino alkyl, arylamino, amino aryl, a protecting group, —CH$_2$OH, —CH$_2$CH$_2$OH, —CH$_2$SO$_2$CH$_3$, —C(=O)R$_x$, —CO$_2$(R$_x$), —C(=O)N(R$_x$)$_2$, —S(O)R$_x$, —NR$_x$(CO)R$_x$, —N(R$_x$)CO$_2$R$_x$, —N(R$_x$)C(=O)N(R$_x$)$_2$, and —N(R$_x$)S(O)$_2$R$_x$, wherein each occurrence of R$_x$ is independently selected from the group consisting of hydrogen, aliphatic, alicyclic, heteroaliphatic, heterocyclic, aromatic, heteroaromatic, aryl, and heteroaryl.

In certain embodiments of these methods, the dipolarophile (IV) is a cinnamate derivative as described above.

In certain preferred embodiments, converting the compound with an aglain core structure into an aglain derivative involves a reduction, for example carried out in the presence of NaBH$_4$, Me$_4$NBH(OAc)$_3$ or another suitable reducing agent. Alternatively, addition of nucleophiles, e.g., Grignard or alkyllithium reagents, may be performed to convert the aglain core-containing compound into an aglain derivative.

In another aspect, the present invention relates to a method for preparing a rocaglamide derivative, the method comprising steps of: producing an oxidopyrylium species (I$_T$) by photoinduced excited state intramolecular proton transfer of a 3 hydroxychromone derivative (I); reacting the oxidopyrylium species obtained with a dipolarophile (IV) to obtain a compound with an aglain core structure (V); and converting the compound with an aglain core structure into a rocaglamide derivative (VII). Compounds (I), (I$_T$), (IV), and (V) are as described above and (VII) has the following chemical structures:

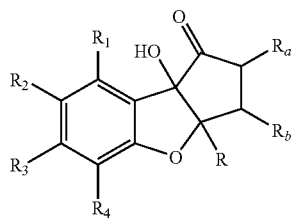

(VII)

wherein $R_1$, $R_2$, $R_3$, $R_4$, R, $R_a$ and $R_b$ are identical or different and selected from the group consisting of hydrogen, halogen, hydroxy, alkoxy, aryloxy, heteroalkoxy, heteroaryloxy, thioalkyl, thioaryl, acyl, aliphatic, alicyclic, heteroaliphatic, heterocyclic, aromatic, heteroaromatic, aryl, heteroaryl, alkylamino, amino alkyl, arylamino, amino aryl, a protecting group, —NO$_2$, —CN, —CF$_3$, —CH$_2$CF$_3$, —CHCl$_2$, —CH$_2$OH, —CH$_2$CH$_2$OH, —CH$_2$SO$_2$CH$_3$, —C(=O)R$_x$, —CO$_2$(R$_x$), —C(=O)N(R$_x$)$_2$, —OC(=O)N(R$_x$)$_2$, —OC(=O)R$_x$, —OCO$_2$R$_x$, —S(O)R$_x$, —S(O)$_2$R$_x$, —NR$_x$(CO)R$_x$, —N(R$_x$)CO$_2$R$_x$, —N(R$_x$)C(=O)N(R$_x$)$_2$, —N(R$_x$)S(O)$_2$R$_x$, and —S(O)$_2$N(R$_x$)$_2$, wherein each occurrence of R$_x$ is independently selected from the group consisting of hydrogen, aliphatic, alicyclic, heteroaliphatic, heterocyclic, aromatic, heteroaromatic, aryl, and heteroaryl.

Alternatively, the method for preparing a rocaglamide derivative comprises steps of: producing an oxidopyrylium species (II$_T$) by photoinduced excited state intramolecular proton transfer of a 3-hydroxyflavone derivative (II); reacting the oxidopyrylium species obtained with a dipolarophile (IV) to obtain a compound with an aglain core structure (V'); and converting the compound with an aglain core structure into a rocaglamide derivative (VII'). Compounds (II), (II$_T$), (IV), and (V') are as described above and (VII') has the following chemical structures:

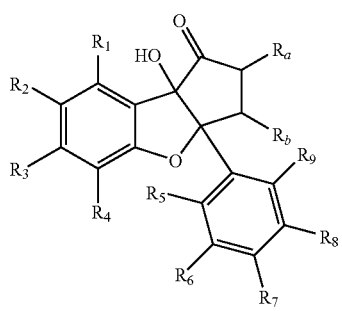

(VII')

wherein $R_1$, $R_2$, $R_3$, $R_4$, $R_5$, $R_6$, $R_7$, $R_8$, $R_9$, $R_a$ and $R_b$ are identical or different and selected from the group consisting of hydrogen, halogen, hydroxy, alkoxy, aryloxy, heteroalkoxy, heteroaryloxy, thioalkyl, thioaryl, acyl, aliphatic, alicyclic, heteroaliphatic, heterocyclic, aromatic, heteroaromatic, aryl, heteroaryl, alkylamino, amino alkyl, arylamino, amino aryl, a protecting group, —NO$_2$, —CN, —CF$_3$, —CH$_2$CF$_3$, CHCl$_2$, —CH$_2$OH, —CH$_2$CH$_2$OH, —CH$_2$SO$_2$CH$_3$, —C(=O)R$_x$, —CO$_2$(R$_x$), —C(=O)N(R$_x$)$_2$, —OC(=O)N(R$_x$)$_2$, —OC(=O)R$_x$, —OCO$_2$R$_x$, —S(O)R$_x$, —S(O)$_2$R$_x$, —NR$_x$(CO)R$_x$, —N(R$_x$)CO$_2$R$_x$, —N(R$_x$)C(=O)N(R$_x$)$_2$, —N(R$_x$)S(O)$_2$R$_x$, and —S(O)$_2$N(R$_x$)$_2$, wherein each occurrence of R$_x$ is independently selected from the group consisting of hydrogen, aliphatic, alicyclic, heteroaliphatic, heterocyclic, aromatic, heteroaromatic, aryl, and heteroaryl.

In certain embodiments of these methods, the dipolarophile (IV) is a cinnamate derivative as described above.

In certain preferred embodiments, converting the compound with an aglain core structure into a rocaglamide derivative comprises an α-ketol (acyloin) rearrangement and optionally a hydroxyl-directed reduction. Preferably, the α-ketol rearrangement is carried out under basic conditions.

Another aspect of the present invention relates to a method for preparing a rocaglamide derivative, the method comprising steps of: producing an oxidopyrylium species (I$_T$) by photoinduced excited state intramolecular proton transfer of a 3-hydroxychromone derivative (I); reacting the oxidopyrylium species obtained with a dipolarophile (IV) to obtain a compound with an aglain core structure (V); and converting the compound with an aglain core structure into a rocaglamide derivative (VIII). Compounds (I), (I$_T$), (IV), and (V) are as described and compound (VIII) has the following chemical structures:

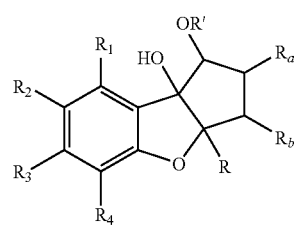

(VIII)

wherein $R_1$, $R_2$, $R_3$, $R_4$, R, $R_a$ and $R_b$ are identical or different and selected from the group consisting of hydrogen, halogen, hydroxy, alkoxy, aryloxy, heteroalkoxy, heteroaryloxy, thioalkyl, thioaryl, acyl, aliphatic, alicyclic, heteroaliphatic, heterocyclic, aromatic, heteroaromatic, aryl, heteroaryl, alkylamino, amino alkyl, arylamino, amino aryl, a protecting group, —NO$_2$, —CN, —CF$_3$, —CH$_2$CF$_3$, —CHCl$_2$, —CH$_2$OH, —CH$_2$CH$_2$OH, —CH$_2$SO$_2$CH$_3$, —C(=O)R$_x$, —CO$_2$(R$_x$), —C(=O)N(R$_x$)$_2$, —OC(=O)N(R$_x$)$_2$, —OC(=O)R$_x$, —OCO$_2$R$_x$, —S(O)R$_x$, —S(O)$_2$R$_x$, —NR$_x$(CO)R$_x$, —N(R$_x$)CO$_2$R$_x$, —N(R$_x$)C(=O)N(R$_x$)$_2$, —N(R$_x$)S(O)$_2$R$_x$, and —S(O)$_2$N(R$_x$)$_2$, wherein each occurrence of R$_x$ is independently selected from the group consisting of hydrogen, aliphatic, alicyclic, heteroaliphatic, heterocyclic, aromatic, heteroaromatic, aryl, and heteroaryl; and wherein R' is selected from the group consisting of hydrogen, alkoxy, aryloxy, heteroalkoxy, heteroaryloxy, acyl, aliphatic, alicyclic, heteroaliphatic, heterocyclic, aromatic, heteroaromatic, aryl, heteroaryl, alkylamino, amino alkyl, arylamino, amino aryl, a protecting group, —CH$_2$OH, —CH$_2$CH$_2$OH, —CH$_2$SO$_2$CH$_3$, —C(=O)R$_x$, —CO$_2$(R$_x$), —C(=O)N(R$_x$)$_2$, —S(O)R$_x$, —NR$_x$(CO)R$_x$, —N(R$_x$)CO$_2$R$_x$, —N(R$_x$)C(=O)N(R$_x$)$_2$, and —N(R$_x$)S(O)$_2$R$_x$, wherein each occurrence of R$_x$ is independently selected from the group consisting of hydrogen, aliphatic, alicyclic, heteroaliphatic, heterocyclic, aromatic, heteroaromatic, aryl, and heteroaryl.

Alternatively, the method for preparing a rocaglamide derivative comprises steps of: producing an oxidopyrylium species $(II_T)$ by photoinduced excited state intramolecular proton transfer of a 3-hydroxyflavone derivative (II); reacting the oxidopyrylium species obtained with a dipolarophile (IV) to obtain a compound with an aglain core structure (V'); and converting the compound with an aglain core structure into a rocaglamide derivative (VIII'). Compounds (II), $(II_T)$, (IV), and (V') are as described above and compound (VIII') has the following chemical structures:

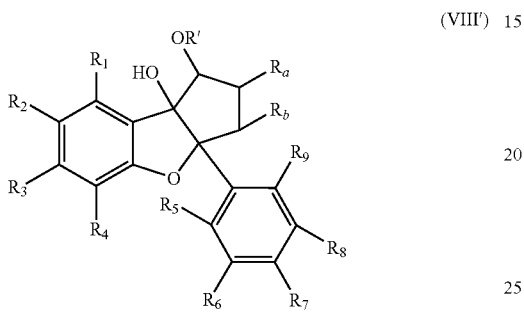

(VIII')

wherein $R_1$, $R_2$, $R_3$, $R_4$, $R_5$, $R_6$, $R_7$, $R_8$, $R_9$, $R_a$ and $R_b$ are identical or different and selected from the group consisting of hydrogen, halogen, hydroxy, alkoxy, aryloxy, heteroalkoxy, heteroaryloxy, thioalkyl, thioaryl, acyl, aliphatic, alicyclic, heteroaliphatic, heterocyclic, aromatic, heteroaromatic, aryl, heteroaryl, alkylamino, amino alkyl, arylamino, amino aryl, a protecting group, $-NO_2$, $-CN$, $-CF_3$, $-CH_2CF_3$, $-CHCl_2$, $-CH_2OH$, $-CH_2CH_2OH$, $-CH_2SO_2CH_3$, $-C(=O)R_x$, $-CO_2(R_x)$, $-C(=O)N(R_x)_2$, $-OC(=O)N(R_x)_2$, $-OC(=O)R_x$, $-OCO_2R_x$, $-S(O)R_x$, $-S(O)_2R_x$, $-NR_x(CO)R_x$, $-N(R_x)CO_2R_x$, $-N(R_x)C(=O)N(R_x)_2$, $-N(R_x)S(O)_2R_x$, and $-S(O)_2N(R_x)_2$, wherein each occurrence of $R_x$ is independently selected from the group consisting of hydrogen, aliphatic, alicyclic, heteroaliphatic, heterocyclic, aromatic, heteroaromatic, aryl, and heteroaryl; and wherein R' is selected from the group consisting of hydrogen, alkoxy, aryloxy, heteroalkoxy, heteroaryloxy, acyl, aliphatic, alicyclic, heteroaliphatic, heterocyclic, aromatic, heteroaromatic, aryl, heteroaryl, alkylamino, amino alkyl, arylamino, amino aryl, a protecting group, $-CH_2OH$, $-CH_2CH_2OH$, $-CH_2SO_2CH_3$, $-C(=O)R_x$, $-CO_2(R_x)$, $-C(=O)N(R_x)_2$, $-S(O)R_x$, $-NR_x(CO)R_x$, $-N(R_x)CO_2R_x$, $-N(R_x)C(=O)N(R_x)_2$, and $-N(R_x)S(O)_2R_x$, wherein each occurrence of $R_x$ is independently selected from the group consisting of hydrogen, aliphatic, alicyclic, heteroaliphatic, heterocyclic, aromatic, heteroaromatic, aryl, and heteroaryl.

In certain embodiments of these methods, the dipolarophile (IV) is a cinnamate derivative as described above.

In certain preferred embodiments, converting the compound with an aglain core structure into a rocaglamide derivative comprises an α-ketol (acyloin) rearrangement and optionally a hydroxyl-directed reduction. Preferably, the α-ketol rearrangement is carried out under basic conditions.

In another aspect, the present invention relates to a method for preparing a forbaglin derivative, the method comprising steps of: producing an oxidopyrylium species $(I_T)$ by photoinduced excited state intramolecular proton transfer of a 3-hydroxychromone derivative (I); reacting the oxidopyrylium species obtained with a dipolarophile (IV) to obtain a compound with an aglain core structure (V); and converting the compound with an aglain core into a forbaglin derivative (IX). Compounds (I), $(I_T)$, (IV), and (V) are as described above and compound (IX) has the following chemical structures:

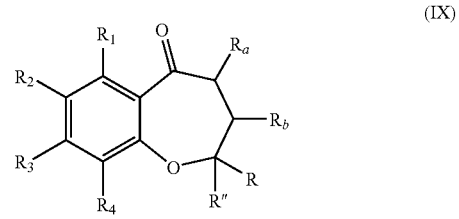

(IX)

wherein $R_1$, $R_2$, $R_3$, $R_4$, R, R", $R_a$ and $R_b$ are identical or different and selected from the group consisting of hydrogen, halogen, hydroxy, alkoxy, aryloxy, heteroalkoxy, heteroaryloxy, thioalkyl, thioaryl, acyl, aliphatic, alicyclic, heteroaliphatic, heterocyclic, aromatic, heteroaromatic, aryl, heteroaryl, alkylamino, amino alkyl, arylamino, amino aryl, a protecting group, $-NO_2$, $-CN$, $-CF_3$, $-CH_2CF_3$, $-CHCl_2$, $-CH_2OH$, $-CH_2CH_2OH$, $-CH_2SO_2CH_3$, $-C(=O)R_x$, $-CO_2(R_x)$, $-C(=O)N(R_x)_2$, $-OC(=O)N(R_x)_2$, $-OC(=O)R_x$, $-OCO_2R_x$, $-S(O)R_x$, $-S(O)_2R_x$, $-NR_x(CO)R_x$, $-N(R_x)CO_2R_x$, $-N(R_x)C(=O)N(R_x)_2$, $-N(R_x)S(O)_2R_x$, and $-S(O)_2N(R_x)_2$, wherein each occurrence of $R_x$ is independently selected from the group consisting of hydrogen, aliphatic, alicyclic, heteroaliphatic, heterocyclic, aromatic, heteroaromatic, aryl, and heteroaryl.

Alternatively, the method for preparing a forbaglin derivative comprises steps of: producing an oxidopyrylium species $(II_T)$ by photoinduced excited state intramolecular proton transfer of a 3-hydroxyflavone derivative (II); reacting the oxidopyrylium species obtained with a dipolarophile (IV) to obtain a compound with an aglain core structure (V'); and converting the compound with an aglain core into a forbaglin derivative (IX'). Compounds (II), $(II_T)$, (IV), and (V') are as described above and compound (IX') has the following chemical structures:

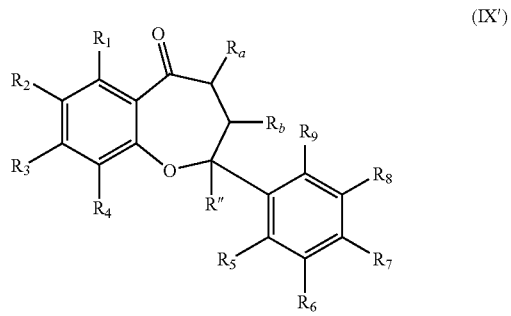

(IX')

wherein $R_1$, $R_2$, $R_3$, $R_4$, $R_5$, $R_6$, $R_7$, $R_8$, $R_9$, R", $R_a$ and $R_b$ are identical or different and selected from the group consisting of hydrogen, halogen, hydroxy, alkoxy, aryloxy, heteroalkoxy, heteroaryloxy, thioalkyl, thioaryl, acyl, aliphatic, alicyclic, heteroaliphatic, heterocyclic, aromatic, heteroaromatic, aryl, heteroaryl, alkylamino, amino alkyl, arylamino, amino aryl, a protecting group, $-NO_2$, $-CN$, $-CF_3$, $-CH_2CF_3$, $-CHCl_2$, $-CH_2OH$, $-CH_2CH_2OH$, —CH$_2$SO$_2$CH$_3$, —C(=O)R$_x$, —CO$_2$(R$_x$), —C(=O)N(R$_x$)$_2$, —OC(=O)N(R$_x$)$_2$, —OC(=O)R$_x$, —OCO$_2$R$_x$, —S(O)R$_x$, —S(O)$_2$R$_x$, —NR$_x$(CO)R$_x$, —N(R$_x$)CO$_2$R$_x$, —N(R$_x$)C(=O)N(R$_x$)$_2$, —N(R$_x$)S(O)$_2$R$_x$, and —S(O)$_2$N(R$_x$)$_2$, wherein each occurrence of R$_x$ is independently selected from the group consisting of hydrogen, aliphatic, alicyclic, heteroaliphatic, heterocyclic, aromatic, heteroaromatic, aryl, and heteroaryl.

In certain embodiments of these methods, the dipolarophile (IV) is a cinnamate derivative as described above.

In certain preferred embodiments, converting the compound with an aglain core structure into a forbaglin derivative comprises an oxidative cleavage, for example, an oxidative cleavage carried out in the presence of Pb(OAc)$_4$.

Another aspect of the present invention relates to aglain core containing compounds (V) and (V'), aglain derivatives (VI) and (VI'), rocaglamide derivatives (VII), (VII'), (VIII) and (VIII'), and forbaglin derivatives (IX) and (IX') prepared by the methods disclosed herein.

Another aspect of the present invention relates to the use of these compounds and derivatives for the manufacture of medicaments for use in the treatment of disease states including cancer or cancerous conditions, conditions associated with cellular hyperproliferation, and NF-κB-associated conditions.

For example, cancer and cancerous conditions that may be treated by such medicaments include leukemia, sarcoma, breast, colon, bladder, pancreatic, endometrial, head and neck, mesothelioma, myeloma, oesophagal/oral, testicular, thyroid, cervical, bone, renal, uterine, prostate, brain, lung, ovarian, skin, liver and bowel and stomach cancers, tumors and melanomas. Conditions associated with cellular hyperproliferation that can be treated using the inventive medicaments may be selected from the group consisting of atherosclerosis, restenosis, rheumatoid arthritis, osteoarthritis, inflammatory arthritis, psoriasis, periodontal disease and virally induced cellular hyperproliferation. NF-κB associated conditions that can be treated using the medicaments disclosed herein may be selected from the group consisting of immunological disorders, septic shock, transplant rejection, radiation damage, reperfusion injuries after ischemia, arteriosclerosis and neurodegenerative diseases.

DEFINITIONS

Figure 1:
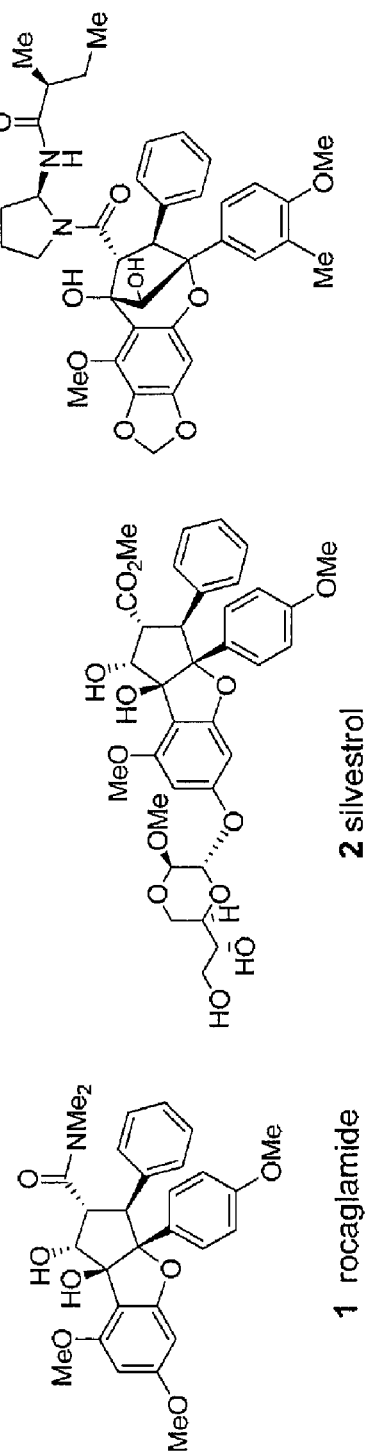
FIG. 1 shows the chemical structures of Rocaglamide and related natural compounds isolated from the plant genus *Aglaia*.
Figure 1:
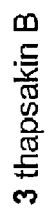
Figure 1:
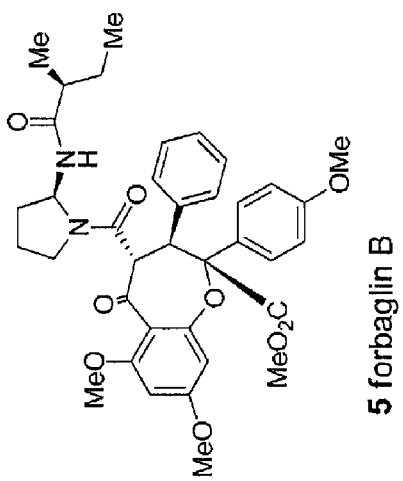
Figure 1:
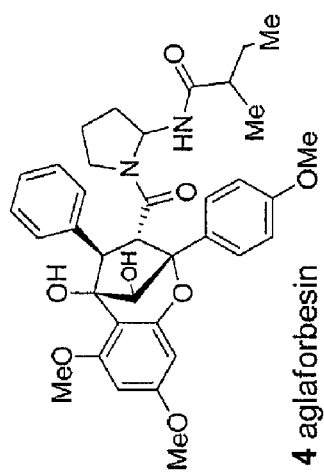
Figure 2:
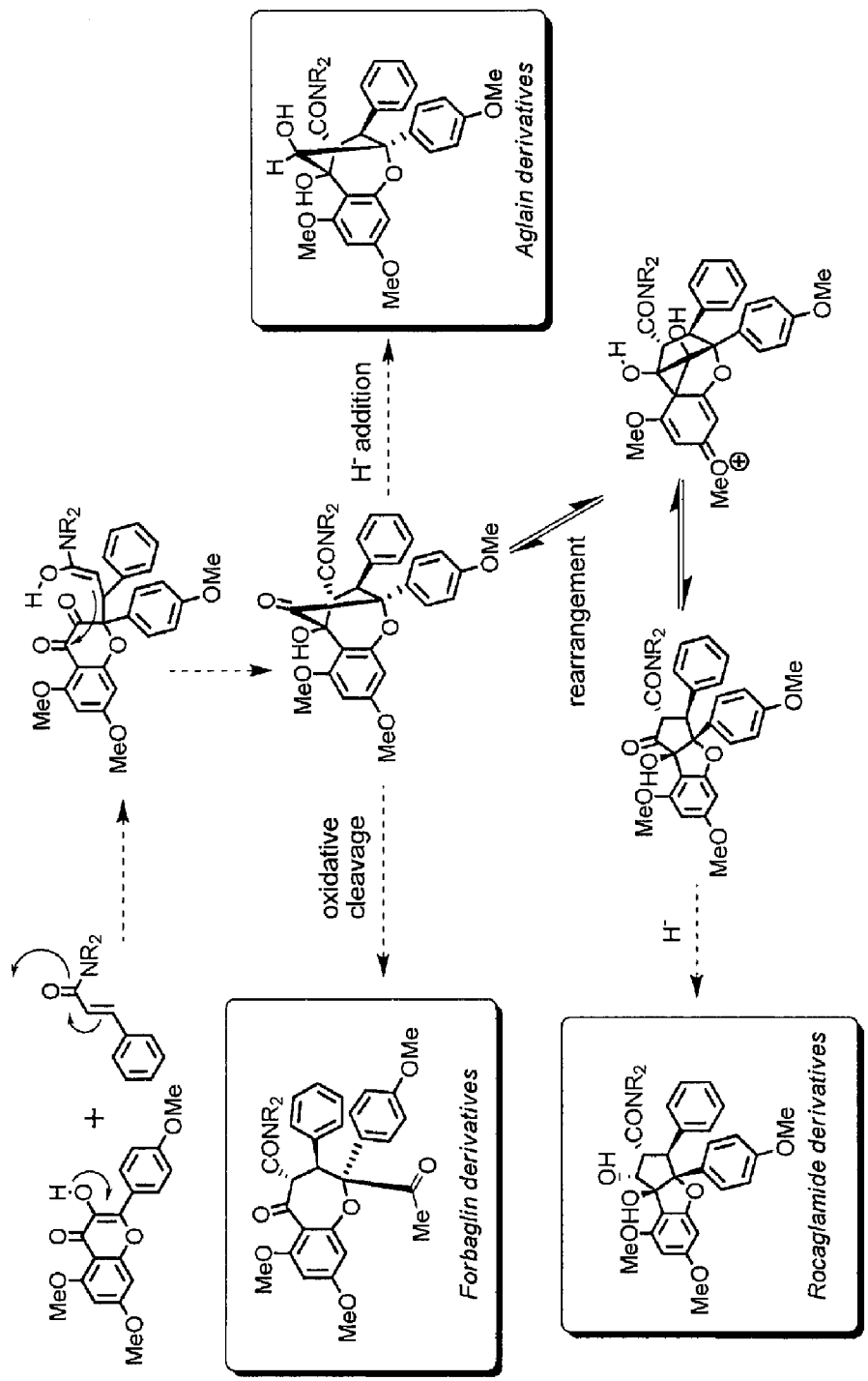
FIG. 2 shows a reaction scheme proposed by Proksch and coworkers (Curr. Org. Chem., 2001, 5: 923-938) for the biosynthetic preparation of the rocaglamides.

Throughout the specification, several terms are employed that axe defined in the following paragraphs.

The terms "oxidopyrylium species" and "oxidopyrylium ylide species" are used herein interchangeably. An oxidopyrylium species is a dipolar entity, i.e., an electrically neutral molecule carrying a positive charge and a negative charge in one of its major canonical descriptions. In the context of the present invention, an oxidopyrylium species preferably comprises the following chemical group/motif:

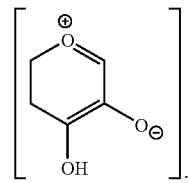

Preferred oxidopyrylium species have chemical structure (I$_T$) or (II$_T$). In most of the inventive methods provided herein, an oxidopyrylium species is, photochemically generated and used as an intermediate in a chemical reaction.

The terms "photochemically generated" and "generated in a photochemical reaction" are used herein interchangeably to characterize a chemical entity whose formation is caused/initiated by absorption of ultraviolet, visible, or infrared radiation. Similarly, a chemical process or reaction is "photoinduced" if it is caused/initiated by absorption of ultraviolet, visible, or infrared radiation. A wide variety of chemical processes/reactions may be photoinduced including, but not limited to, additions, cyclizations, eliminations, enolizations, rearrangements, isomerizations, oxidations, reductions, substitutions, and the like.

As used herein, the term "intermediate" refers to a molecular entity with a lifetime appreciably longer than a molecular vibration that is formed (directly or indirectly) from one or more reactants and reacts further to give (either directly or indirectly) the product(s) of a chemical reaction.

The term "cycloaddition", as used herein, refers to a chemical reaction in which two or more π-electron systems (e.g., unsaturated molecules or parts of the same unsaturated molecule) combine to form a cyclic product in which there is a net reduction of the bond multiplicity. In a cycloaddition, the n electrons are used to form new a bonds. The product of a cycloaddition is called an "adduct" or a "cycloadduct". Different types of cycloaddition are known in the art including, but not limited to, 1,3-dipolar cycloadditions and Diels-Alder reactions.

As used herein, the term "converting" refers to a process or reaction that is aimed at modifying a chemical compound. A variety of processes or reactions can be used to convert or modify a chemical compound including, but not limited to, additions, eliminations, substitutions, oxidations, reductions, enolizations, rearrangements, isomerizations, and the like.

The term "alipitatic", as used herein, includes both saturated and unsaturated, straight chain (i.e., unbranched) or branched aliphatic hydrocarbons, which are optionally substituted with one or more functional groups. As will be appreciated by one of ordinary skill in the art, the term "aliphatic" is intended herein to include, but is not limited to, alkyl, alkenyl, or alkynyl moieties. As used herein, the term "alkyl" includes straight and branched alkyl groups. An analogous convention applies to other generic terms such as "alkenyl", "alkynyl" and the like. Furthermore, as used herein, the terms "alkyl", "alkenyl", "alkynyl" and the like encompass both substituted and unsubstituted groups. In certain embodiments, as used herein, "lower alkyl" is used to indicate those alkyl groups (substituted, unsubstituted, branched or unbranched) having 1-6 carbon atoms. "Lower alkelnyl" and "lower alkynyl" respectively include corresponding 1-6 carbon moieties.

In certain embodiments, the alkyl, alkenyl and alkynyl groups employed in the invention contain 1-20; 2-20; 3-20; 4-20; 5-20; 6-20; 7-20 or 8-20 aliphatic carbon atoms. In certain other embodiments, the alkyl, alkenyl, and alkynyl groups employed in the invention contain 1-10; 2-10; 3-10; 4-10; 5-10; 6-10; 7-10 or 8-10 aliphatic carbon atoms. In yet other embodiments, the alkyl, alkenyl, and alkynyl groups employed in the invention contain 1-8; 2-8; 3-8; 4-8; 5-8; 6-20 or 7-8 aliphatic carbon atoms. In still other embodiments, the alkyl, alkenyl, and alkynyl groups employed in the invention contain 1-6; 2-6; 3-6; 4-6 or 5-6 aliphatic carbon atoms. In yet other embodiments, the alkyl, alkenyl, and alkynyl groups employed in the invention contain 1-4; 2-4 or 3-4 carbon atoms. Illustrative aliphatic groups thus include, but are not limited to, for example, methyl, ethyl, n-propyl, isopropyl, alkyl, n-butyl, sec-butyl, isobutyl, tert-butyl, n-pentyl, sec-pentyl, isopentyl, tert-pentyl, n hexyl, sec-hexyl, moieties and the like, which again, may bear one or more substituents. Alkenyl groups include, but are not limited to, for example, ethenyl, propenyl, butenyl, 1-methyl-2-buten-1-yl, and the like. Representative alkynyl groups include, but are not limited to, ethynyl, 2-propynyl (propargyl), 1-propynyl and the like.

The term "alicyclic", as used herein, refers to compounds which combine the properties of aliphatic and cyclic compounds and include, but are not limited to, monocyclic, or polycyclic aliphatic hydrocarbons and bridged cycloalkyl compounds, which are optionally substituted with one or more functional groups. As will be appreciated by one of ordinary skill in the art, the term "alicyclic" is intended herein to include, but is not limited to, cycloalkyl, cycloalkenyl, and cycloalkynyl moieties, which are optionally substituted with one or more functional groups. Illustrative alicyclic groups thus include, but are not limited to, for example, cyclopropyl, —$CH_2$-cyclopropyl, cyclobutyl, —$CH_2$-cyclobutyl, cyclopentyl, —$CH_2$-cyclopentyl, cyclohexyl, —$CH_2$-cyclohexyl, cyclohexenylethyl, cyclohexanylethyl, norborbyl moieties and the like, which again, may bear one or more substituents.

The term "alkoxy" or "alkyloxy", as used herein refers to a saturated (i.e., O-alkyl) or unsaturated (i.e., O-alkenyl and O-alkynyl) group attached to the parent molecular moiety through an oxygen atom. In certain embodiments, the alkyl group contains 1-20; 2-20; 3-20; 4-20; 5-20; 6-20; 7-20 or 8-20 aliphatic carbon atoms. In certain other embodiments, the alkyl group contains 1-10; 2-10; 3-10; 4-10; 5-10; 6-10; 7-10 or 8-10 aliphatic carbon atoms. In yet other embodiments, the alkyl, alkenyl, and alkynyl groups employed in the invention contain 1-8; 2-8; 3-8; 4-8; 5-8; 6-20 or 7-8 aliphatic carbon atoms. In still other embodiments, the alkyl group contains 1-6; 2-6; 3-6; 4-6 or 5-6 aliphatic carbon atoms. In yet other embodiments, the alkyl group contains 1-4; 2-4 or 3-4 aliphatic carbon atoms. Examples of alkoxy groups, include but are not limited to, methoxy, ethoxy, propoxy, isopropoxy, n-butoxy, i-butoxy, sec-butoxy, tert-butoxy, neopentoxy, n-hexoxy and the like.

The term "thioalkyl", as used herein, refers to a saturated (i.e., S-alkyl) or unsaturated (i.e., S-alkenyl and S-alkynyl) group attached to the parent molecular moiety through a sulfur atom. In certain embodiments, the alkyl group contains 1-20 aliphatic carbon atoms. In certain other embodiments, the alkyl group contains 1-10 aliphatic carbon atoms. In yet other embodiments, the alkyl, alkenyl, and alkynyl groups employed in the invention contain 1-8 aliphatic carbon atoms. In still other embodiments, the alkyl group contains 1-6 aliphatic carbon atoms. In yet other embodiments, the alkyl group contains 1-4 aliphatic carbon atoms. Examples of thioalkyl groups include, but are not limited to, methylthio, ethylthio, propylthio, isopropylthio, n-butylthio, and the like.

The term "alkylamino" refers to a group having the structure —$NHR_a$ wherein $R_a$ is aliphatic or alicyclic, as defined herein. The term "amino alkyl" refers to a group having the structure $NH_2R_a$—, wherein $R_a$ is aliphatic or alicyclic, as defined herein. In certain embodiments, the aliphatic or alicyclic group contains 1-20 aliphatic carbon atoms. In certain other embodiments, the aliphatic or alicyclic group contains 1-10 aliphatic carbon atoms. In still other embodiments, the aliphatic or alicyclic group contains 1-6 aliphatic carbon atoms. In yet other embodiments, the aliphatic or alicyclic group contains 1-4 aliphatic carbon atoms. In yet other embodiments, $R_a$ is an alkyl, alkenyl, or alkynyl group containing 1-8 aliphatic carbon atoms. Examples of alkylamino groups include, but are not limited to, methylamino, ethylamino, iso-propylamino and the like.

Some examples of substituents (or functional groups) of the above-described aliphatic (and other) moieties of compounds of the invention include, but are not limited to aliphatic, alicyclic, heteroaliphatic, heterocyclic, aromatic, heteroaromatic, aryl, heteroaryl, alkylaryl, heteroalkylaryl, alkylheteroaryl, heteroalkylheteroaryl, alkoxy, aryloxy, heteroalkoxy, heteroaryloxy, alkylthio, arylthio, heteroalkylthio, heteroarylthio, F, Cl, Br, I, —OH, —NO$_2$, —CN, —CF$_3$, —CH$_2$CF$_3$, —CHCl$_2$, —CH$_2$OH, —CH$_2$CH$_2$OH, —CH$_2$NH$_2$, —CH$_2$SO$_2$CH$_3$, —C(=O)R$_x$, —CO$_2$(R$_x$), —C(=O)N(R$_x$)$_2$, —OC(=O)R$_x$, —OCO$_2$R$_x$, —OC(=O)N (R$_x$)$_2$, —N(R$_x$)$_2$, —OR$_x$, —SR$_x$, —S(O)R$_x$, —S(O)$_2$R$_x$, —NR$_x$(CO)R$_x$, —N(R$_x$)CO$_2$R$_x$, —N(R$_x$)S(O)$_2$R$_x$, —N(R$_x$)C(=O)N(R$_x$)$_2$, —S(C))$_2$N(R$_x$)$_2$, wherein each occurrence of R$_x$ independently includes, but is not limited to, aliphatic, alicyclic, heteroaliphatic, heterocyclic, aryl, heteroaryl, alkylaryl, alkylheteroaryl, heteroalkylaryl or heteroalkylheteroaryl, wherein any of the aliphatic, alicyclic, heteroaliphatic, heterocyclic, alkylaryl, or alkylheteroaryl groups described above and herein may be substituted or unsubstituted, branched or unbranched, saturated or unsaturated, and wherein any of the aryl or heteroaryl substituents described above and herein may be substituted or unsubstituted.

In general, the term "aromatic moiety" or "aromatic", as used herein, refers to a stable mono- or poly-cyclic, unsaturated moiety having preferably 3-14 carbon atoms, each of which may be substituted or unsubstituted. In certain embodiments, the term "aromatic moiety" refers to a planar ring having p-orbitals perpendicular to the plane of the ring at each ring atom and satisfying the Huckel rule where the number of g electrons in the ring is (4n+2) wherein n is an integer. A mono- or polycyclic, unsaturated moiety that does not satisfy one or all of these criteria for aromaticity is defined herein as "non-aromatic", and is encompassed by the term "alicyclic".

In general, the term "heteroaromatic", as used herein, refers to a stable mono- or polycyclic, unsaturated moiety having preferably 3-14 carbon atoms, each of which may be substituted or unsubstituted; and comprising at least one heteroatom selected from O, S and N within the ring (i.e., in place of a ring carbon atom). In certain embodiments, the term "heteroaromatic moiety" refers to a planar ring comprising at least one heteroatom, having p-orbitals perpendicular to the plane of the ring at each ring atom, and satisfying the Huckel rule where the number of π electrons in the ring is (4n+2) wherein n is an integer.

It will also be appreciated that aromatic and heteroaromatic moieties, as defined herein may be attached via an alkyl or heteroalkyl moiety and thus also include -(alkyl)aromatic, -(heteroalkyl)aromatic, -(heteroalkyl)heteroaromatic, and -(heteroalkyl)heteroaromatic moieties. Thus, as used herein, the phrases "aromatic or heteroaromatic moieties" and "aromatic, heteroaromatic, -(alkyl)aromatic, -(heteroalkyl)aromatic, -(heteroalkyl)heteroaromatic, and -(heteroalkyl) heteroaromatic" are interchangeable. Substituents include, but are not limited to, any of the previously mentioned substituents, i.e., the substituents recited for aliphatic moieties, or for other moieties as disclosed herein, resulting in the formation of a stable compound.

The term "aryl", as used herein, does not differ significantly from the common meaning of the term in the art, and refers to an unsaturated cyclic moiety comprising at least one aromatic ring. In certain embodiments, the term "aryl" refers to a mono- or bicyclic carbocyclic ring system having one or two aromatic rings including, but not limited to, phenyl, naphthyl, tetrahydronaphthyl, indanyl, indenyl and the like.

The term "heteroaryl", as used herein, refers to a cyclic aromatic radical having from five to ten ring atoms of which one ring atom is selected from S, O and N; zero, one or two ring atoms are additional heteroatoms independently selected from S, O and N; and the remaining ring atoms are carbon, the radical being joined to the rest of the molecule via any of the ring atoms, such as, for example, pyridyl, pyrazinyl, pyrimidinyl, quinolinyl, isoquinolinyl, and the like.

It will be appreciated that aryl and heteroaryl groups (including bicyclic aryl groups) can be unsubstituted or substituted, wherein substitution includes replacement of one or more of the hydrogen atoms thereon independently with any one or more substituents. Suitable substituents include, but are not limited to, any of the previously mentioned substituents, i.e., the substituents recited for aliphatic moieties, or for other moieties as disclosed herein, resulting in the formation of a stable compound.

The term "cycloalkyl", as used herein, refers specifically to groups having three to seven, preferably three to ten carbon atoms. Suitable cycloalkyls include, but are not limited to, cyclopropyl, cyclobutyl, cyclopentyl, cyclohexyl, cycloheptyl and the like, which, as in the case of aliphatic, alicyclic, heteroaliphatic or heterocyclic moieties, may optionally be substituted with any of the previously mentioned substituents.

The term "heteroaliphatic", as used herein, refers to aliphatic moieties in which one or more carbon atoms in the main chain have been substituted with a heteroatom. Thus, a heteroaliphatic group refers to an aliphatic chain which contains one or more oxygen, sulfur, nitrogen, phosphorus or silicon atoms, e.g., in place of carbon atoms. Heteroaliphatic moieties may be linear or branched, and saturated or unsaturated. In certain embodiments, heteroaliphatic moieties are substituted by independent replacement of one or more of the hydrogen atoms thereon with one or more of the previously mentioned substituents.

The term "heterocycloalkyl", "heterocycle" or "heterocyclic", as used herein, refers to compounds which combine the properties of heteroaliphatic and cyclic compounds and include, but are not limited to, saturated and unsaturated mono- or polycyclic cyclic ring systems having 5-16 atoms wherein at least one ring atom is a heteroatom selected from O, S and N (wherein the nitrogen and sulfur heteroatoms may optionally be oxidized), wherein the ring systems are optionally substituted with one or more functional groups, as defined herein. In certain embodiments, the term "heterocycloalkyl", "heterocycle" or "heterocyclic" refers to a non-aromatic 5-, 6- or 7-membered ring or a polycyclic group wherein at least one ring atom is a heteroatom selected from O, S and N (wherein the nitrogen and sulfur heteroatoms may optionally be oxidized), including, but not limited to, a bi- or tri-cyclic group, comprising fused six-membered rings having between one and three heteroatoms independently selected from oxygen, sulfur and nitrogen, wherein (i) each 5-membered ring has 0 to 2 double bonds, each 6-membered ring has 0 to 2 double bonds and each 7-membered ring has 0 to 3 double bonds, (ii) the nitrogen and sulfur heteroatoms may optionally be oxidized, (iii) the nitrogen heteroatom may optionally be quaternized, and (iv) any of the above heterocyclic rings may be fused to an aryl or heteroaryl ring. Representative heterocycles include, but are not limited to, heterocycles such as furanyl, thiofuranyl, pyranyl, pyrrolyl, pyrazolyl, imidazolyl, thienyl, pyrrolidinyl, pyrazolinyl, pyrazolidinyl, imidazolinyl, imidazolidinyl, piperidinyl, piperazinyl, oxazolyl, oxazolidinyl, isooxazolyl, isoxazolidinyl, dioxazolyl, thiadiazolyl, oxadiazolyl, tetrazolyl, triazolyl, thiatriazolyl, oxatriazolyl, thiadiazolyl, oxadiazolyl, morpholinyl, thiazolyl, thiazolidinyl, isothiazolyl, isothiazolidinyl, dithiazolyl, dithiazolidinyl, tetrahydrofuryl, and benzo-fused derivatives thereof. The term "heterocycle, or heterocycloalkyl or heterocyclic" also encompasses heterocycle, or heterocycloalkyl or heterocyclic groups that are substituted by the independent replacement of one, two or three of the hydrogen atoms thereon with any of the previously mentioned substituents. Additionally, it will be appreciated that any of the alicyclic or heterocyclic moieties described above and herein may comprise an aryl or heteroaryl moiety fused thereto.

The terms "halo" and "halogen", as used herein, refer to an atom selected from fluorine, chlorine, bromine and iodine.

The term "haloalkyl" denotes an alkyl group, as defined above, having one, two, or three halogen atoms attached thereto and is exemplified by such groups as chloromethyl, bromoethyl, trifluoromethyl, and the like.

The term "amino", as used herein, refers to a primary ($-NH_2$), secondary ($-NHR_x$), tertiary ($-NR_xR_y$) or quaternary ($-N^+R_xR_yR_z$) amine, where $R_x$, $R_y$ and $R_z$ are independently an aliphatic, alicyclic, heteroaliphatic, heterocyclic, aromatic or heteroaromatic moiety, as defined herein. Examples of amino groups include, but are not limited to, methylamino, dimethylamino, ethylamino, diethylamino, diethylaminocarbonyl, methylethylamino, iso-propylamino, piperidino, trimethylamino, and propylamino.

The term "acyl", as used herein, refers to a group having the general formula $-C(=O)R_b$, where $R_b$ is an aliphatic, alicyclic, heteroaliphatic, heterocyclic, aromatic or heteroaromatic moiety, as defined herein.

As used herein, the terms "aliphatic", "heteroaliphatic", "alkyl", "alkenyl", "alkynyl", "heteroalkyl", "heteroalkenyl", "heteroalkynyl", and the like encompass substituted and unsubstituted, saturated and unsaturated, and linear and branched groups. Similarly, the terms "alicyclic", "heterocyclic", "heterocycloalkyl", "heterocycle" and the like encompass substituted and unsubstituted, and saturated and unsaturated groups. Additionally, the terms "cycloalkyl", "cycloalkenyl", "cycloalkynyl", "heterocycloalkyl", "heterocycloalkenyl", "heterocycloalkynyl", "aromatic", "heteroaromatic", "aryl", "heteroaryl" and the like encompass both substituted and unsubstituted groups.

By the term "protecting group", as used herein, it is meant that a particular functional moiety, e.g., O, S, or N, is temporarily blocked so that a reaction can be carried out selectively at another reactive site in a multifunctional compound. In preferred embodiments, a protecting group reacts selectively in good yield to give a protected substrate that is stable to the projected reactions; the protecting group must be selectively removed in good yield by readily available, preferably non-toxic reagents that do not attack the other functional groups; the protecting group forms an easily separable derivative (more preferably without the generation of new stereogenic centers); and the protecting group has a minimum of additional functionality to avoid further sites of reaction. Oxygen, sulfur, nitrogen and carbon protecting groups may be utilized. For example, oxygen protecting groups include, but are not limited to, methyl ethers, substituted methyl ethers (e.g., MOM (methoxymethyl ether), MTM (methylthiomethyl ether), BOM (benzyloxymethyl ether), PMBM or MPM (p-methoxybenzyloxymethyl ether), to name a few), substituted ethyl ethers, substituted benzyl ethers, silyl ethers (e.g., TMS (trimethylsilyl ether), TES (triethylsilylether), TIPS (triisopropylsilyl ether), TBDMS (t-butyldimethylsilyl ether), tribenzyl silyl ether, TBDPS (t-butyldiphenyl silyl ether), to name a few), esters (e.g., formate, acetate, benzoate (Bz), trifluoroacetate, dichloroacetate, to name a few), carbonates, cyclic acetals and ketals. In certain other exemplary embodiments, nitrogen protecting groups are utilized. Nitrogen protecting groups include, but are not limited to, carbamates (including methyl, ethyl and substituted ethyl carbamates (e.g., Troc), to name a few) amides, cyclic imide derivatives, N-Alkyl and N-Aryl amines, imine derivatives, and enamine derivatives, to name a few. It will be appreciated that the present invention is not intended to be limited to these protecting groups; rather, a variety of additional equivalent protecting groups can be readily identified using the above criteria and utilized in the present invention. Additionally, a variety of protecting groups are described in "*Protective Groups in Organic Synthesis*" T. W. Greene and P. G. Wuts (Eds.), John Wiley & Sons: New York, 1999 (3$^{rd}$ Ed), the entire contents of which are incorporated herein by reference.

As used herein, the term "medicament" refers to any substance or combination of substances that has a beneficial or therapeutic effect. In preferred embodiments of the present invention, the manufacture of a medicament comprises the use of at least one derivative of the rocaglamide/aglain/forbaglin family prepared by the methods provided herein. For example, a medicament according to the present invention may comprise one or more derivatives of the rocaglamide/aglain/forbaglin family as active ingredient(s). A medicament may further comprise one or more other active ingredients, such as drugs or therapeutic agents known in the art or newly discovered agents whose activity is to be tested, and/or one or more pharmaceutically acceptable carriers. As used herein, the term "pharmaceutically acceptable carrier" refers to a carrier medium which does not interfere with the effectiveness of the biological activity of the active ingredients and which is not excessively toxic to the hosts at the concentrations at which it is administered. The term includes solvents, dispersion media, coatings, antibacterial and antifungal agents, isotonic agents, absorption delaying agents, and the like. The use of such media and agents for pharmaceutically active substances is well known in the art (see, for example, Remington's Pharmaceutical Sciences, E. W. Martin, 18$^{th}$ Ed., 1990, Mack Publishing Co.: Easton, Pa.).

The term "treatment" is used herein to characterize a method or process that is aimed at (1) delaying or preventing the onset of a disease or condition; or (2) slowing down or stopping the progression, aggravation, or deterioration of the symptoms of the disease or condition; or (3) bringing about ameliorations of the symptoms of the disease or condition; or (4) curing the disease or condition. The treatment may be administered prior to the onset of the disease, for a prophylactic or preventive action. Alternatively or additionally, the treatment may be administered after initiation of the disease or condition, for a therapeutic action.

DETAILED DESCRIPTION OF CERTAIN PREFERRED EMBODIMENTS

The present invention is directed to a new, unified biomimetic approach to the synthesis of rocaglamides and related aglains and forbaglins. An embodiment of this new approach is outlined in FIG. 3.

Figure 3:
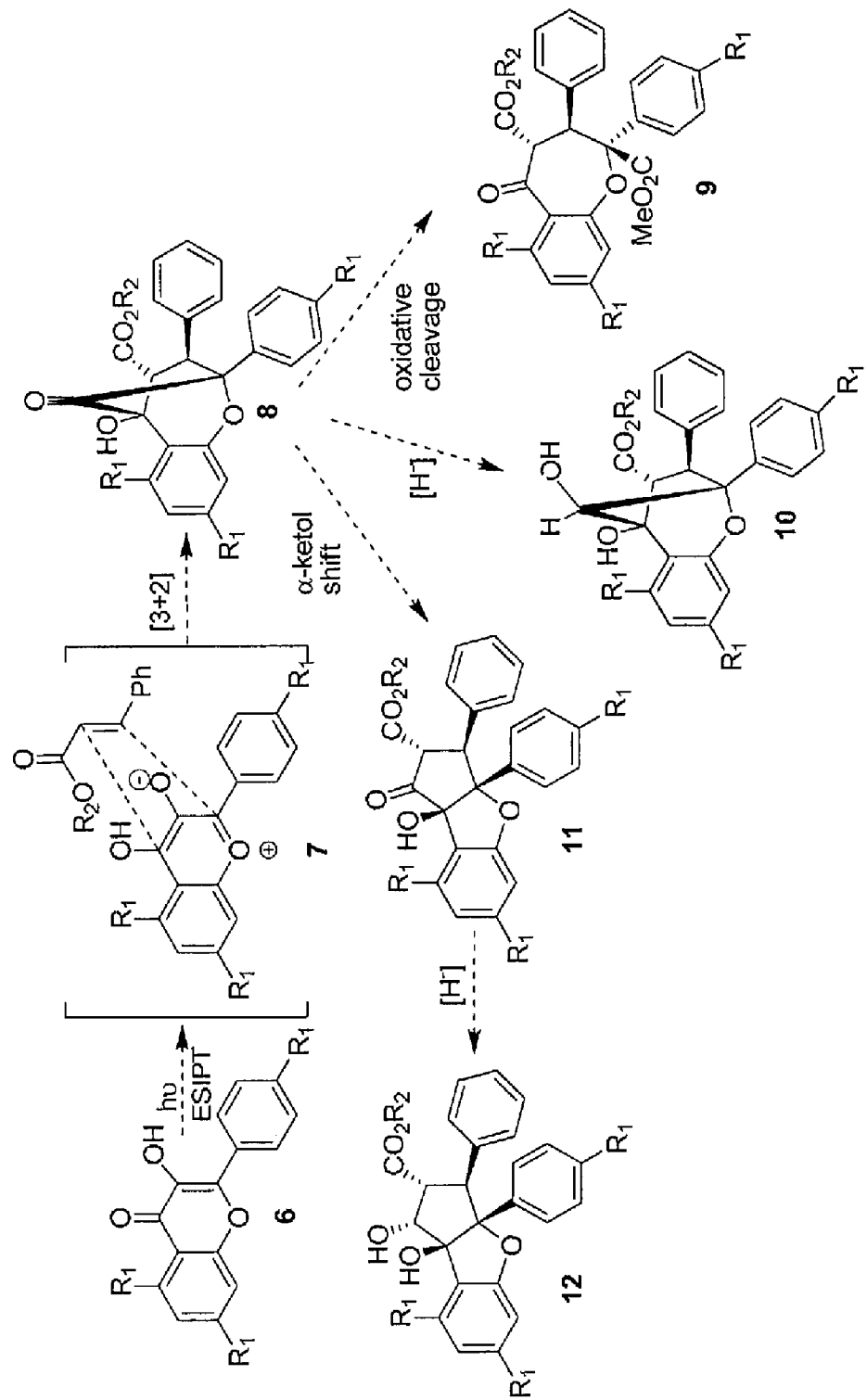
FIG. 3 shows an embodiment of the inventive unified biomimetic approach to the synthesis of Aglains-Forbaglins-Rocaglamides.

More specifically, the inventive synthetic method shown in FIG. 3 involves photochemical generation of an oxidopyrylium species (compound 7) via excited state intramolecular proton transfer (ESIPT) of a 3-hydroxyflavone derivative 6 followed by 1,3-dipolar cycloaddition (i.e., [3+2]cycloaddition) of the oxidopyrylium species to a dipolarophile, such as a cinnamate derivative. This reaction results in the formation of the adduct 8, which contains an aglain core structure. Conversion of 8 by oxidative cleavage yields forbaglin 9, while reduction of the adduct 8 produces aglain 10. Core structure 8 may alternatively be converted to hydrorocaglate 11 by α-ketol (acyloin) rearrangement; and hydroxyl-directed reduction of 11 affords rocaglate 12.

I. Excited State Intramolecular Proton Transfer (ESIPT)

An ESIPT phenomenon involves a very fast intramolecular transfer of a proton. In some cases, this process takes place in only tens or hundreds of femtoseconds (M. Kasha, J. Chem. Soc. Faraday Trans. 2, 1986, 82: 2379-2392; B. J. Schwartz et al., J. Phys. Chem., 1992, 96: 3591-3598; F. Laermer et al., Chem. Phys. Lett., 1988, 148: 119-124).

Literature reports have documented excited state intramolecular proton transfer (see, for example, P.-T. Chou, J. Chin. Chem. Soc., 2001, 48: 651-682; A. D. Roschal et al., J. Phys. Chem. A, 1998, 102: 5907-5914; A. Bader et al., J. Phys. Chem. A, 2002, 106: 2844-2849 and references therein; A. Samanta et al., J. Phys. Chem. A, 2003; 107: 6334-6339; A. P. Demchenlco, J. Phys. Chem. A, 2003, 107: 4211-4216; R. Rastogi et al., Spectrochem. Acta, Part A, 2001, 57: 299-308) of 3-hydroxyflavone derivatives leading to the formation of an oxidopyrylium species (J. Hendrickson and J. S. Farina, J. Org. Chem., 1980, 45: 3359-3361; P. G. Sammes et al., J. Chem. Soc. Perkin Trans. I, 1983, 1261-1265; P. A. Wender et al., J. Am. Chem. Soc., 1997, 119: 12976-12977; J. E. Baldwin et al., Tetrahedron Lett., 2003; 44: 4543-4545).

Figure 4:
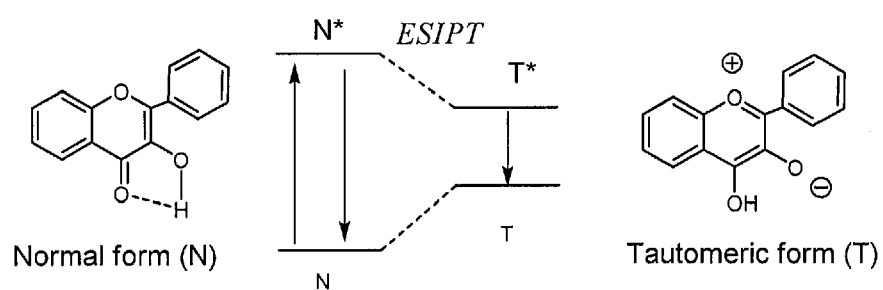
FIG. 4 is a scheme showing the excited state intramolecular proton transfer (ESIPT) process and fluorescence emission taking place upon photoirradiation of the parent molecule, 3-hydroxyflavone.

The overall ESIPT process (shown on FIG. 4 in the case of the parent molecule, 3-hydroxyflavone, 3-HF) involves generation of a putative tautomeric form of 3-HF, where the proton of the hydroxyl group at position C3 migrates to the ketone group at position C4 to give an oxidopyrylium species (tautomeric form T).

Although ESIPT processes of 3-HF derivatives have been reported in the literature to produce excited state species such as the oxidopyrylium, there are no reports of chemical reactions using these species. The present invention encompasses the recognition by the Applicants that the reactivity of such oxidopyrylium species can be advantageously exploited in chemical reactions.

Accordingly, one aspect of the present invention relates to the use of photochemically generated oxidopyrylium species as intermediates in chemical reactions. Preferably, the oxidopyrylium species is photochemically generated via a process comprising an excited state intramolecular proton transfer.

As will be appreciated by those of ordinary skill in the art, any organic molecule which can produce an oxidopyrylium species upon photochemical excitation is suitable for use in the practice of the present invention. Particularly suitable compounds comprise a 5-hydroxy-pyran-4-one group/motif, including, but not limited to, 5-hydroxy-2,3-dihydro-pyran-4-one derivatives. 3-hydroxychromone derivatives (M. Itoh, Pure and Applied Chemistry, 1993, 65: 1629-1634; A. S. Klymchenko et al., New J. Chem., 2004, 28: 687-692) and 3-hydroxyflavone derivatives. When the photochemically generated oxidopyrylium species is used in the preparation of rocaglamides and related aglains and forbaglins according to the new synthetic approach provided herein, the oxidopyrylium species is preferably generated by photochemical excitation of a 3-hydroxychromone derivative of chemical structure (I) or 3-hydroxyflavone derivative of chemical structure (II).

Methods for photochemically exciting organic molecules are known in the art. Photochemical irradiation of 3-hydroxyflavone derivatives is described in Example 1 and Example 5.

II. Cycladdition Reactivity of Oxidopyrylium Species

In preferred embodiments, the photochemically generated oxidopyrylium species is used as a reactive intermediate in a cycloaddition, such as a 1,3-dipolar cycloaddition.

Initial efforts by the Applicants toward understanding the cycloaddition reactivity of the oxidopyrylium species T (see FIG. 4) were focused on model studies using 3-hydroxyflavone, the parent compound and simplest molecule of the 3-hydroxyflavone family.

Oxidopyrylium Species Generated from 3-Hydroxyflavone

Figure 5:
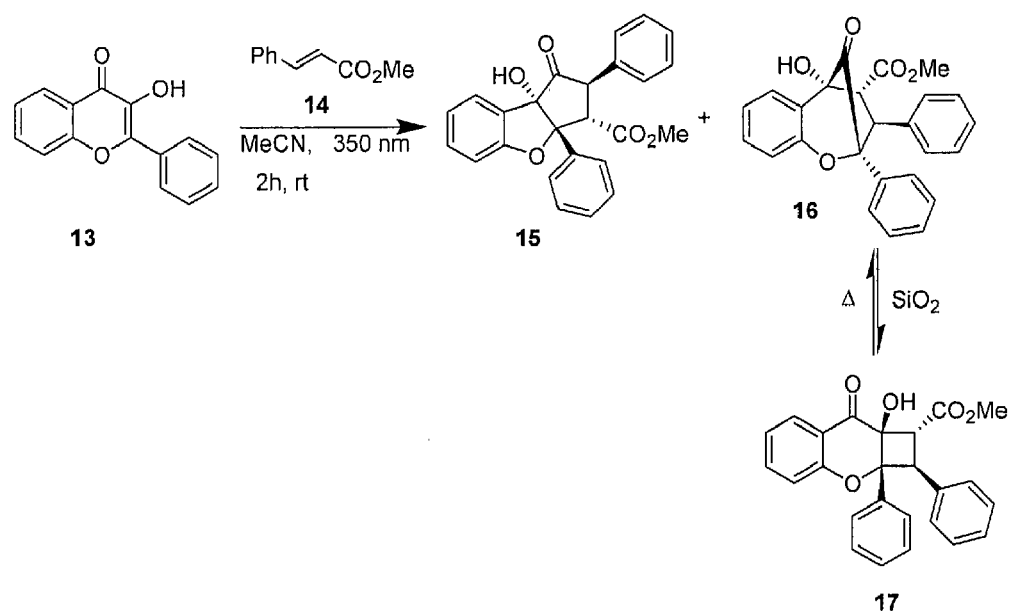
FIG. 5 shows the reaction of photochemical [3+2]cycloaddition between 3-hydroxyflavone 13 and methyl cinnamate 14.

Photoirradiation of 3-hydroxyflavone 13 in presence of the dipolarophile methyl cinnamate 14 was carried out in acetonitrile using a 450 W pressure mercury lamp (uranium filter, λ>350 nm). After irradiation at room temperature for 2 hours, compound 13 was consumed and a mixture of products was obtained, resulting, presumably, from [3+2]cycloaddition (see FIG. 5 and Example 1).

Figure 6:
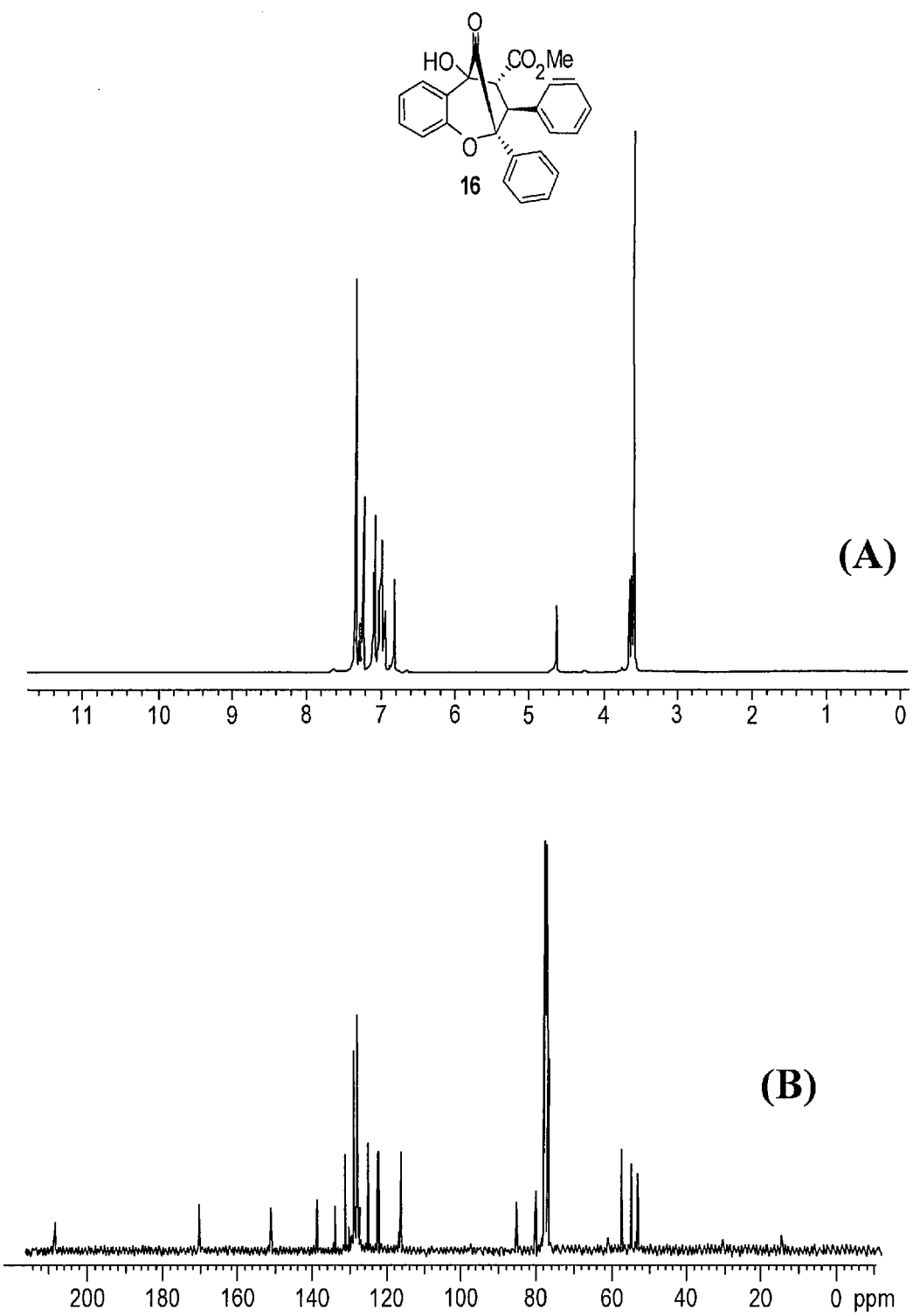
FIG. 6 shows the $^1$H-NMR (400 MHz, CDCl$_3$) (A) and $^{13}$C-NMR (75 MHz, CDCl$_3$) (B) spectra recorded for compound 16, which results from photochemical [3+2]cycloaddition between 3-hydroxyflavone 13 and methyl cinnamate 14.
Figure 7:
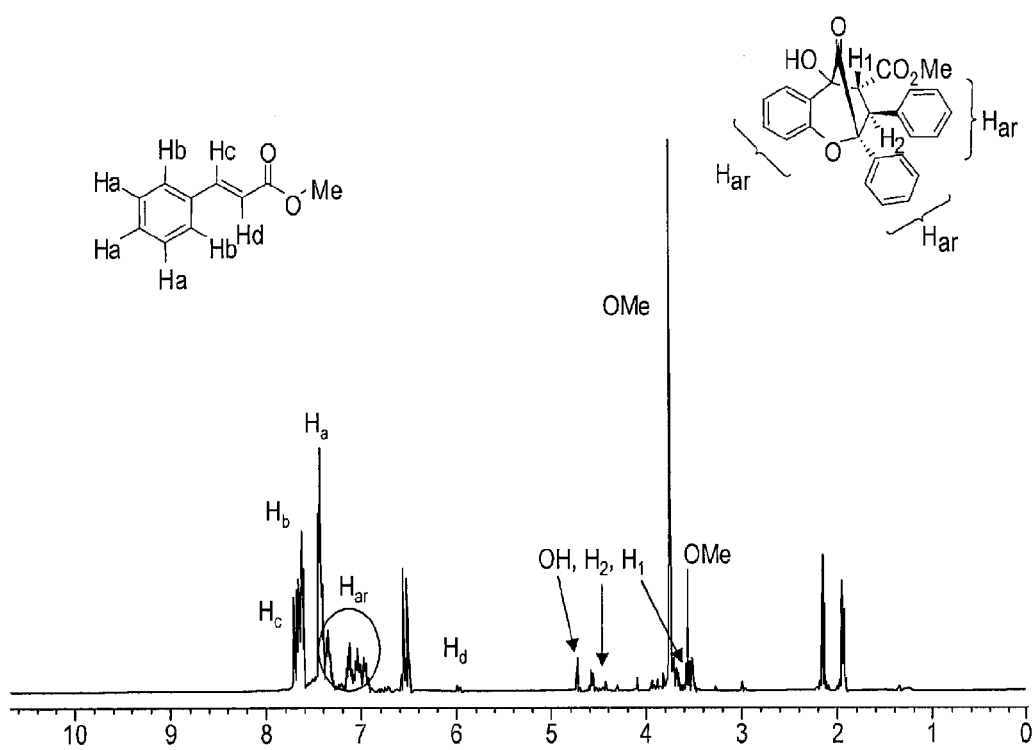
FIG. 7 shows the $^1$H-NMR spectrum (400 MHz, CD$_3$CN) of a mixture of 3-hydroxyflavone 13 (1 equivalent) and methyl cinnamate 14 (5 equivalents) after 2 hours of irradiation. The chemical structure of methyl cinnamate 14 is presented in red and the chemical structure of compound 16, the main product of the reaction, is presented in blue.
Figure 8A:
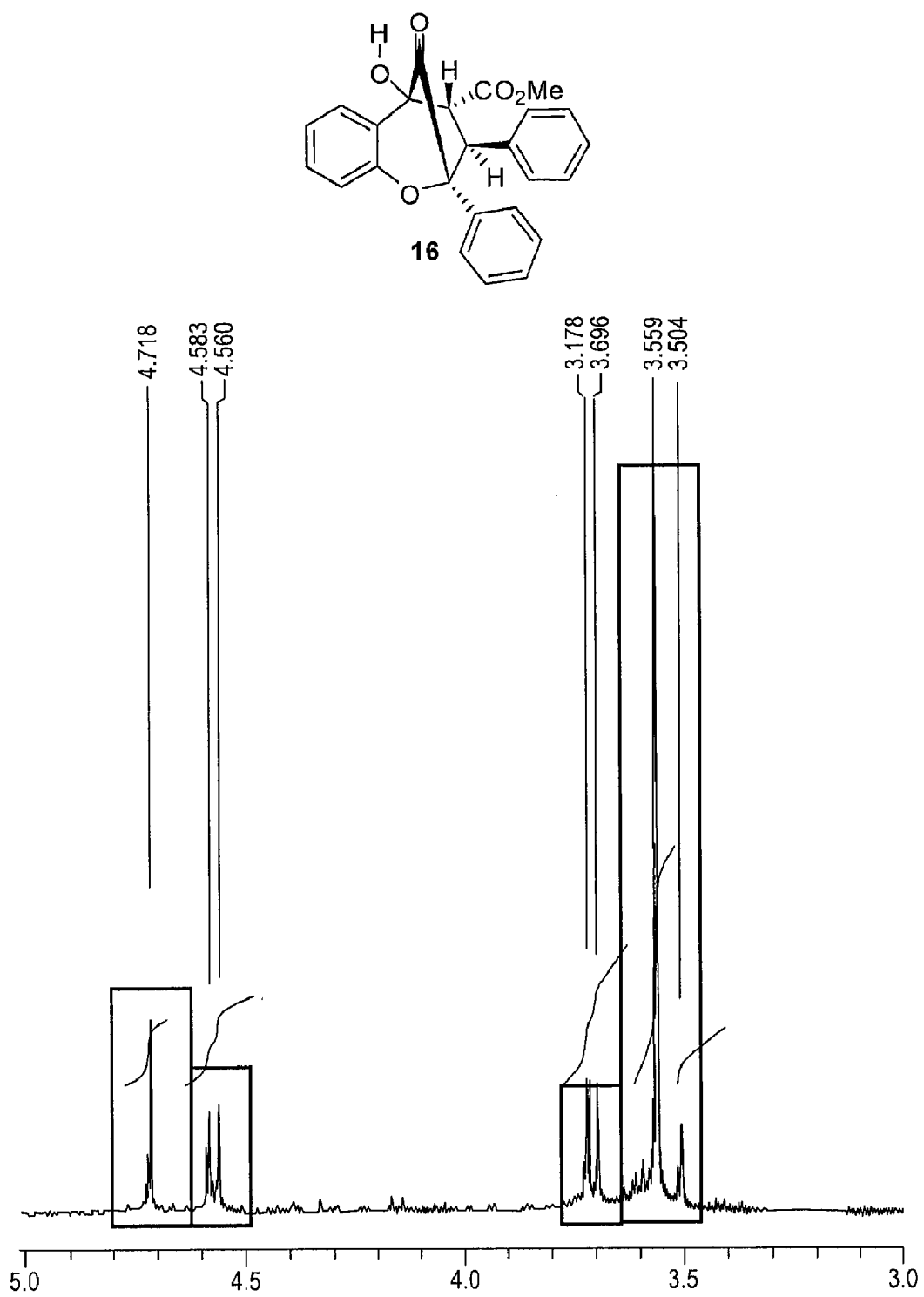
FIG. 8 shows parts (3 to 5 ppm) of expanded $^1$H-NMR spectra (400 MHz, CD$_3$CN) recorded for compound 16 (FIG. 8(A)); and for a mixture of 3 hydroxyflavone 13 and methyl cinnamate 14 after 2 hours of irradiation (FIG. 8(B)).
Figure 8B:
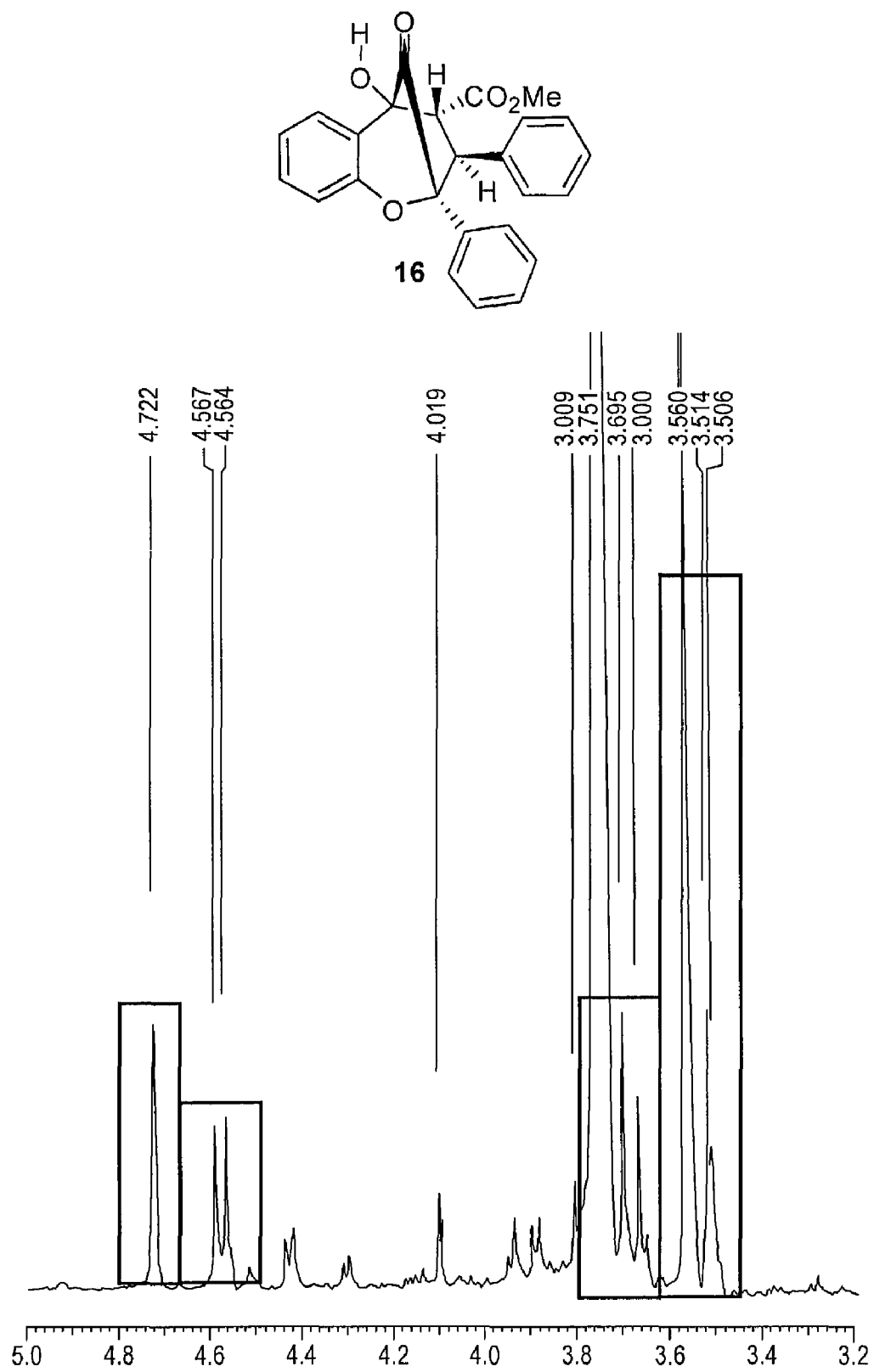

Based on spectroscopic data and X-ray analysis of a crystalline derivative (see Example 1), the major compound (56%) was confirmed to be the endo cycloadduct 16 in which the phenyl ring of the dipolarophile is anti to the oxido bridge (P. G. Sammes and L. J. Street, J. Phys. Chem., 1998, 102: 5907-5914). $^1$H-NMR and $^{13}$C-NMR spectra recorded for compound 16 are presented in FIG. 6. Interestingly, an equilibrium between 16 and the benzo[b]cyclobutapyran-8-one 17 is observed during silica gel purification resulting from an acid-mediated ketol shift (X. Creary et al., J. Org. Chem., 1985, 50: 1932-1938). The equilibrium between the two core structures was found to be controlled by temperature: heating a mixture of compounds 16 and 17 (ethyl acetate, 65° C.) was observed to lead to the formation of compound 16 exclusively. Monitoring of the photocycloaddition by $^1$H-NMR (in $CD_3CN$) also confirmed formation of 16 as the major product (see FIG. 7 and FIGS. 8(A and B)).

Compound 15 (14%) was identified as a cyclopenta[b] tetrahydrobenzofuran by further conversion into a crystalline derivative. In contrast to 16, compound 15 is derived from exo [3+2]cycloaddition to an aglaforbesin type ring system (see compound 4 in FIG. 1) followed by acycloin rearrangement during the photoirradiation process (further experiments to support the ESIPT mechanism were conducted using 3-methoxyflavone). Irradiation (350 nm, acetonitrile, 5 equivalents of 18, at room temperature) did not give a [3+2]cycloadduct but instead provided a product resulting from oxidative photocycloaddition (T. Matsuura and T. Takemo, Tetrahedron, 1973, 3337-3340).

Conversion of Cycloadduct 16

Figure 9:
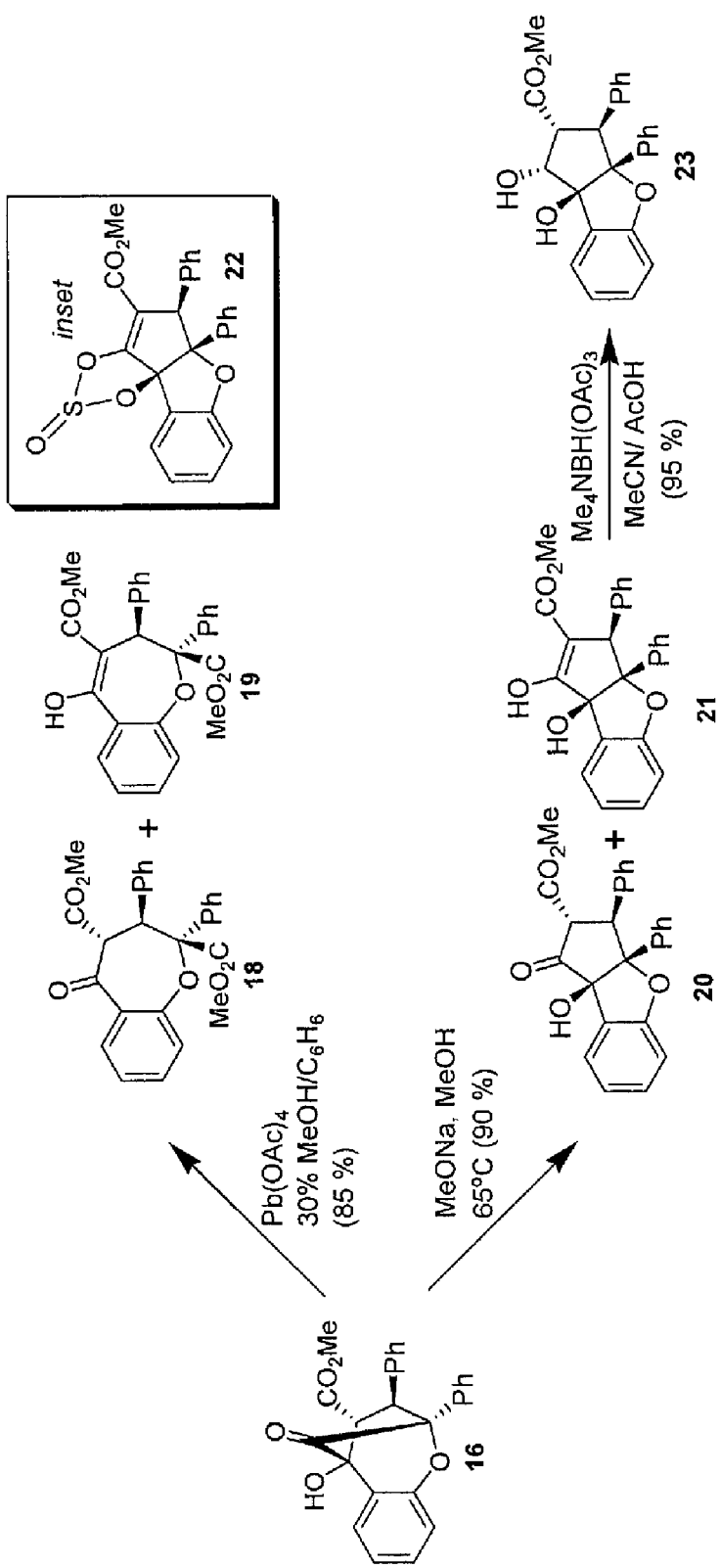
FIG. 9 shows an example of chemical conversion of an aglain core structure to forbaglin and rocaglamide ring systems.

Cycloadduct 16, which contains an aglain core structure, was then evaluated for its ability to be converted to compounds containing rocaglamide and forbaglin ring systems (as shown on FIG. 9). Oxidative cleavage of the aglain core to the forbaglin ring system may be conducted using $Pb(OAc)_4$ (E. Baer, J. Am. Chem. Soc., 1940, 62: 1597-1606). Treatment of cycloadduct 16 with $Pb(OAc)_4$ in benzene/methanol at room temperature afforded benzo[b]oxepines 18:19 as a 2:1 mixture of keto-enol tautomers (85%) (see Example 2).

The aglain core structure of compound 16 may alternatively be converted to dehydrorocaglate by α-ketol (acyloin) rearrangement (L. A. Paquette and J. E. Hofferberth, Org. React., 2003, 62: 477-567; for ketol shifts in biogenesis, see, for example, M. Rentzea and E. Hecker, Tetrahedron Lett., 1982, 23: 1785-1788; and D. H. G. Crout and D. L. Rathbone, J. Chem. Soc. Chem. Commun., 1987, 290-291)

Attempted thermal acycloin rearrangement (J. Lui et al., Tetrahedron, 1998, 54: 11637-11650) of compound 16 did not afford any observable ketol shift product. Acyloin rearrangements have alternatively been conducted using acidic or basic conditions or employing metal catalysis and have been used with success in a number of natural product syntheses (for K252a, see, for example, K. Tamalki et al., Tetrahedron Lett., 2002, 43: 379-382; for Taxanes, see, for example, L. Paquette and J. E. Hofferberth, J. Org. Chem., 2003, 68: 2266-2275).

Treatment of cycloadduct 16 with protic or Lewis acidic conditions ($BF_3$, $Et_2O$, $ZnCl_2$) resulted in decomposition of the starting material. However, treatment of cycloadduct 16 under basic conditions (2.5 equivalents of NaOMe, methanol) (X. Creary et al., J. Org. Chem., 1985, 50: 1932-1938), afforded a 1:1 mixture of keto-enol tautomers 20:21 (see Example 3). The success of basic conditions for α-ketol rearrangement may be explained by the fact that such basic conditions favor the formation of the enolate of 21, which may drive the ketol shift equilibrium (E. Piers et al., Synlett., 1999, 7: 1082-1084) towards the rocaglamide core.

Further proof for this assumption was provided by treatment of cycloadduct 16 with NaH (2.1 equivalent, tetrahydrofuran, room temperature) and quenching of the reaction mixture with thionyl chloride, which led to the formation of the stable 1,3,2-dioxathiolane 22 (48%) (M. Shipman et al., Tetrahedron, 1999, 55: 108445-10850) (see Example 3).

Figure 10:
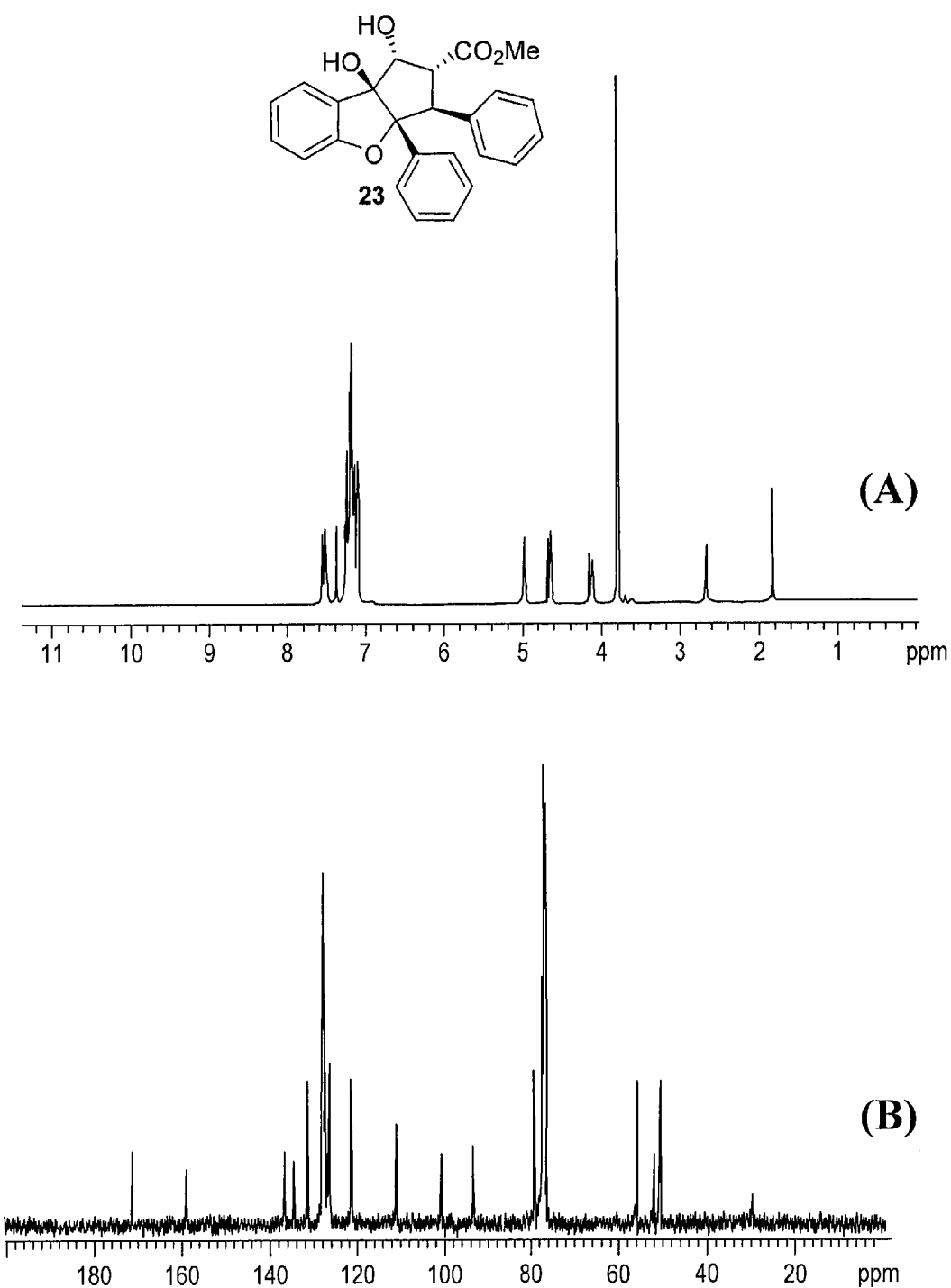
FIG. 10 shows the $^1$H-NMR (400 MHz, CDCl$_3$) (A) and $^{13}$C-NMR (75 MHz, CDCl$_3$) (B) spectra recorded for compound 23.

Hydroxyl-directed reduction (B. Trost et al., J. Am. Chem. Soc., 1990, 112: 9022-9024) of 20:21 afforded rocagolate 23 (95%) (see Example 4). The $^1$H-NMR and $^{13}$C-NMR spectra of compound 23 are presented on FIG. 10.

Oxidopyrylium Species Generated from Methoxy-Substituted 3-Hydroxyflavone

Figure 11:
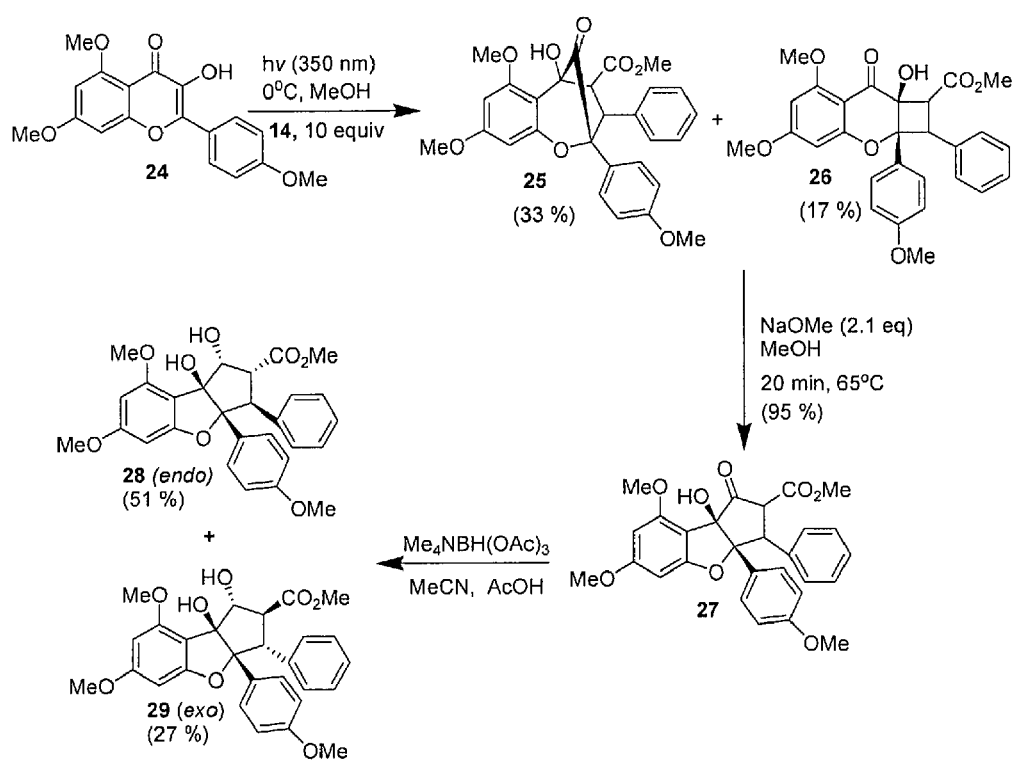
FIG. 11 is a scheme presenting an example of synthesis of (i) methyl rocaglate from trimethoxy-substituted 3-hydroxyflavone.
Figure 12:
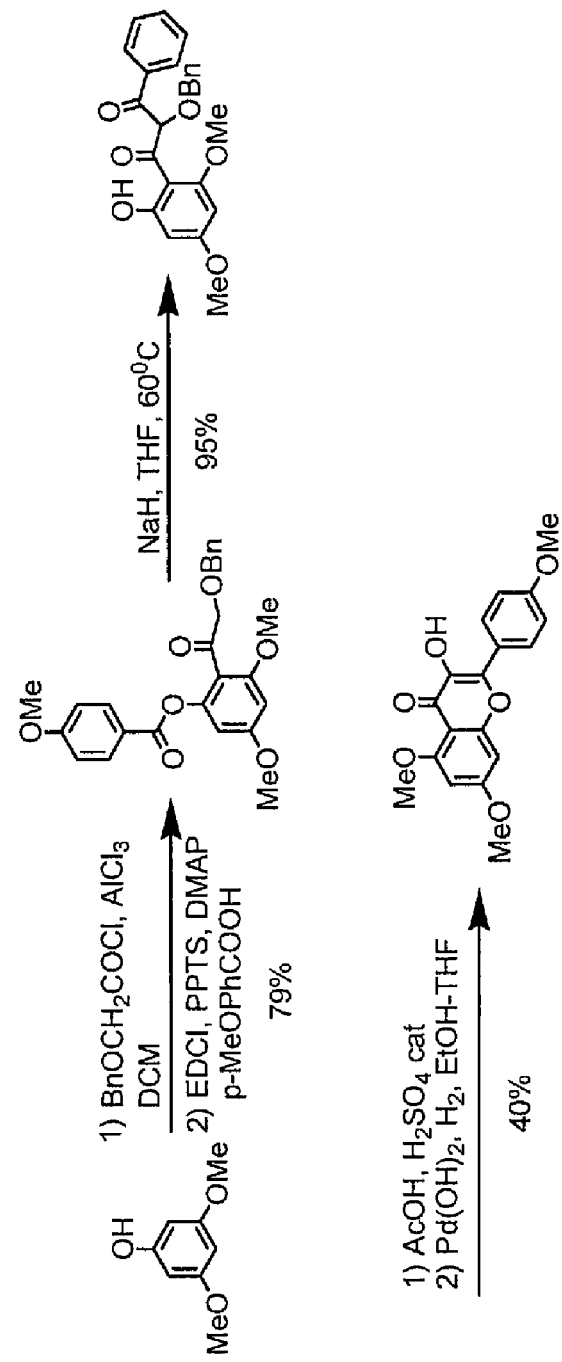
FIG. 12 shows the reaction sequence used to synthesize trimethoxy-substituted 3-hydroxyflavone 24.

3-Hydroxyflavone derivatives with methoxy substitutions were then evaluated for their suitability in the synthesis of rocaglamides and related compounds. The overall synthetic scheme is presented on FIG. 11 in the case of the trimethoxy-substituted 3-hydroxyflavone. Trimethoxy-substituted 3-hydroxyflavone was synthesized following a procedure adapted from a reaction sequence reported by H. Tanaka and coworkers (Tetrahedron Lett., 2000, 41: 9735-9739) as shown in FIG. 12. Photoirradiation (uranium filter) of kaempferol derivative 24 and methyl cinnamate 14 (Y.-J. Lee and T.-D. Wu, J. Chin. Chem. Soc., 2001, 48: 201-206) in methanol at 0° C. afforded the aglain 25 as well as benzo[b]cyclobutapyran-8-one 26 (33% and 17%, respectively) after purification on $SiO_2$ (see Example 5).

Conversion of Compounds 25 and 26

Basic conditions (NaOMe, methanol) were used to effect α-ketol rearrangement of compound 25 and compound 26 (see Example 6). In the case of compound 25, the reaction led to the formation of a mixture of eudo and exo cycloadducts 27, in which the endo isomer was obtained as a mixture of keto-enol tautomers 27'/27" (the chemical structures of compounds 27, 27' and 27" are presented on FIG. 12). In the case of compound 26, the base-mediated reaction only gave the endo cycloadduct 27.

Figure 14:
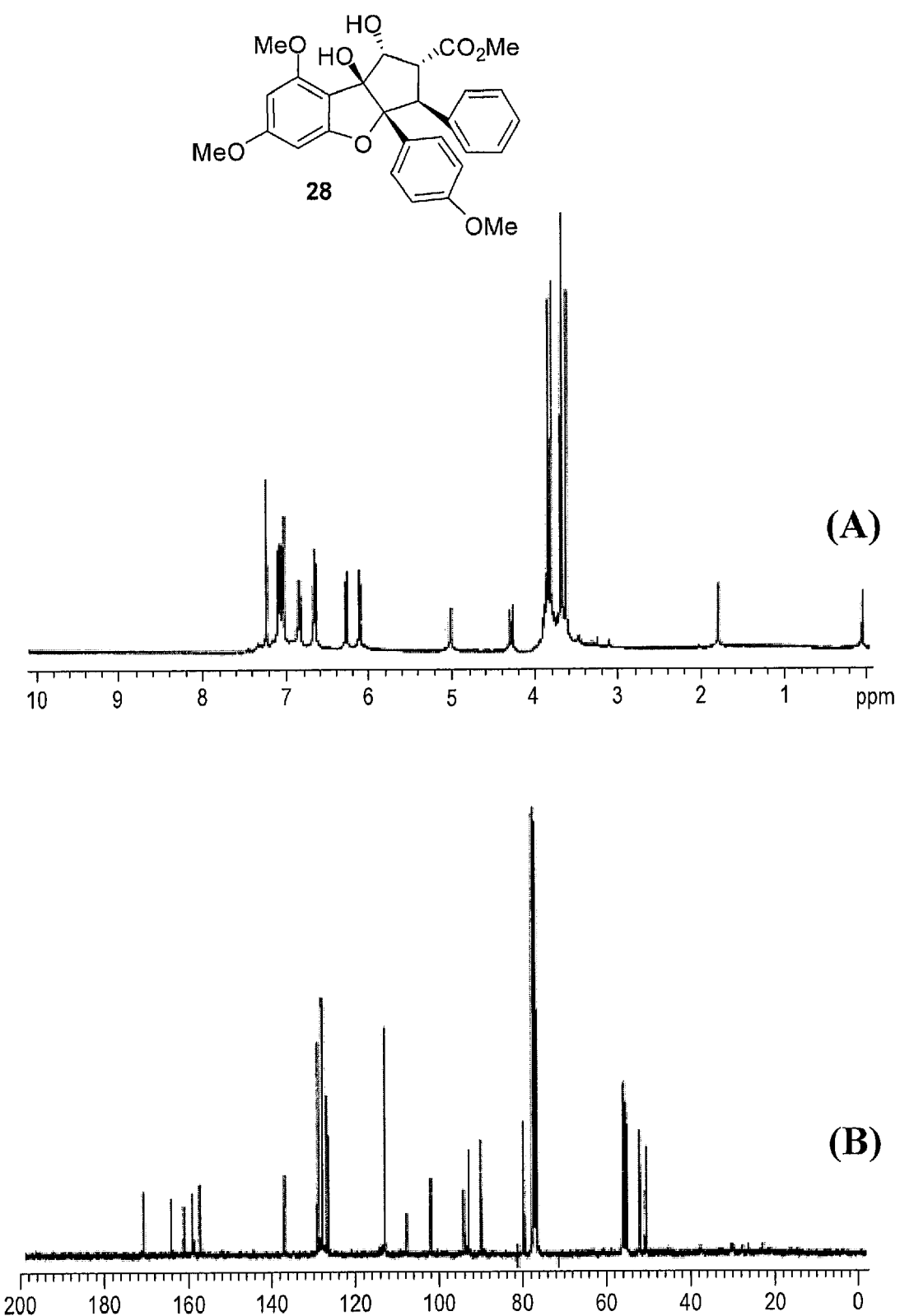
FIG. 14 shows the $^1$H-NMR (400 MHz, CDCl$_3$) (A) and $^{13}$C-NMR (75 MHz, CDCl$_3$) (B) spectra recorded for compound 28.
Figure 15:
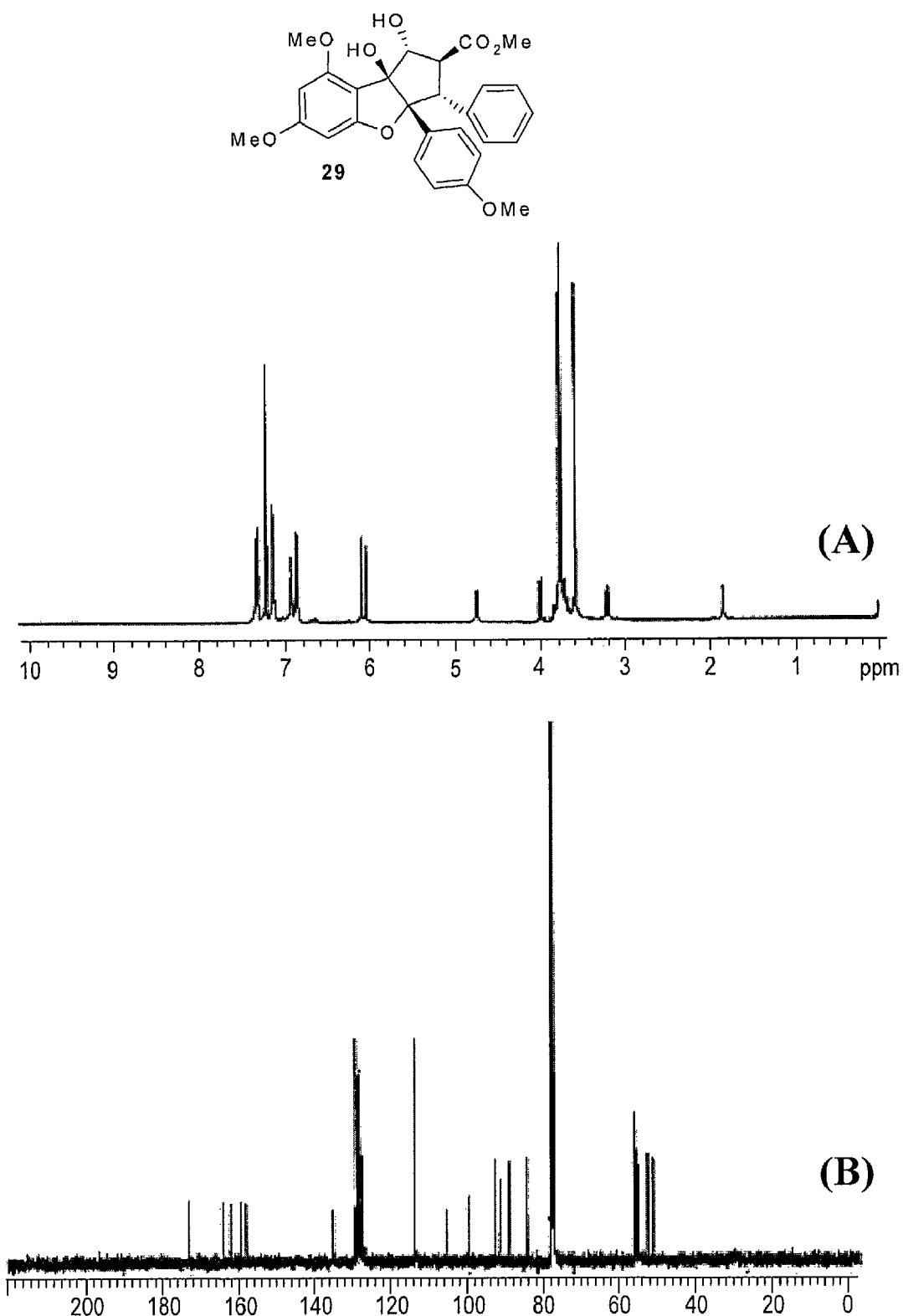
FIG. 15 shows the $^1$H-NMR (400 MHz, CDCl$_3$) (A) and $^{13}$C-NMR (75 MHz, CDCl$_3$) (B) spectra recorded for compound 29.
Figure 16:
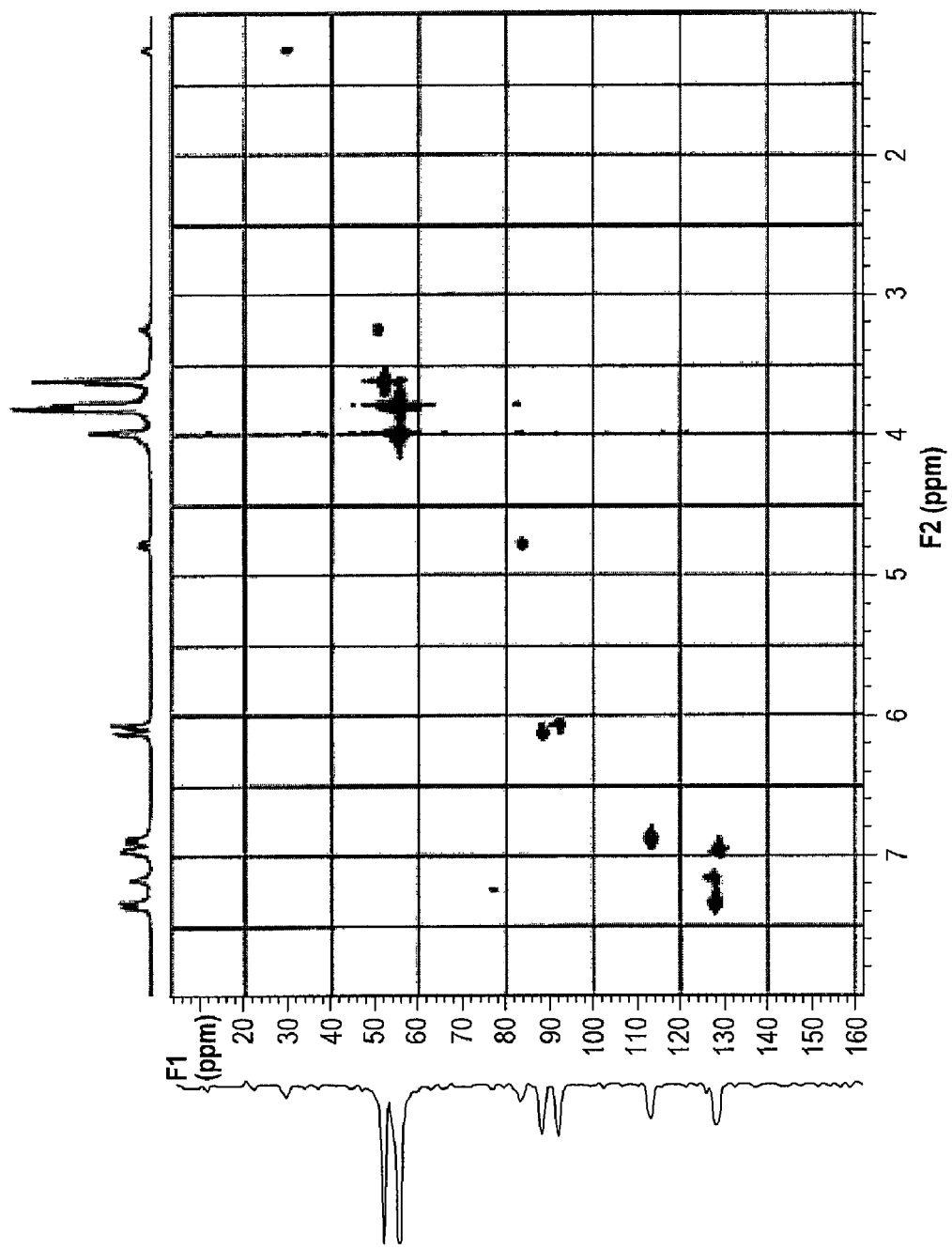
FIG. 16 shows the HMQC spectrum of synthetic exo methyl rocaglate 29 (500 MHz, CHCl$_3$, 25° C.).
Figure 17:
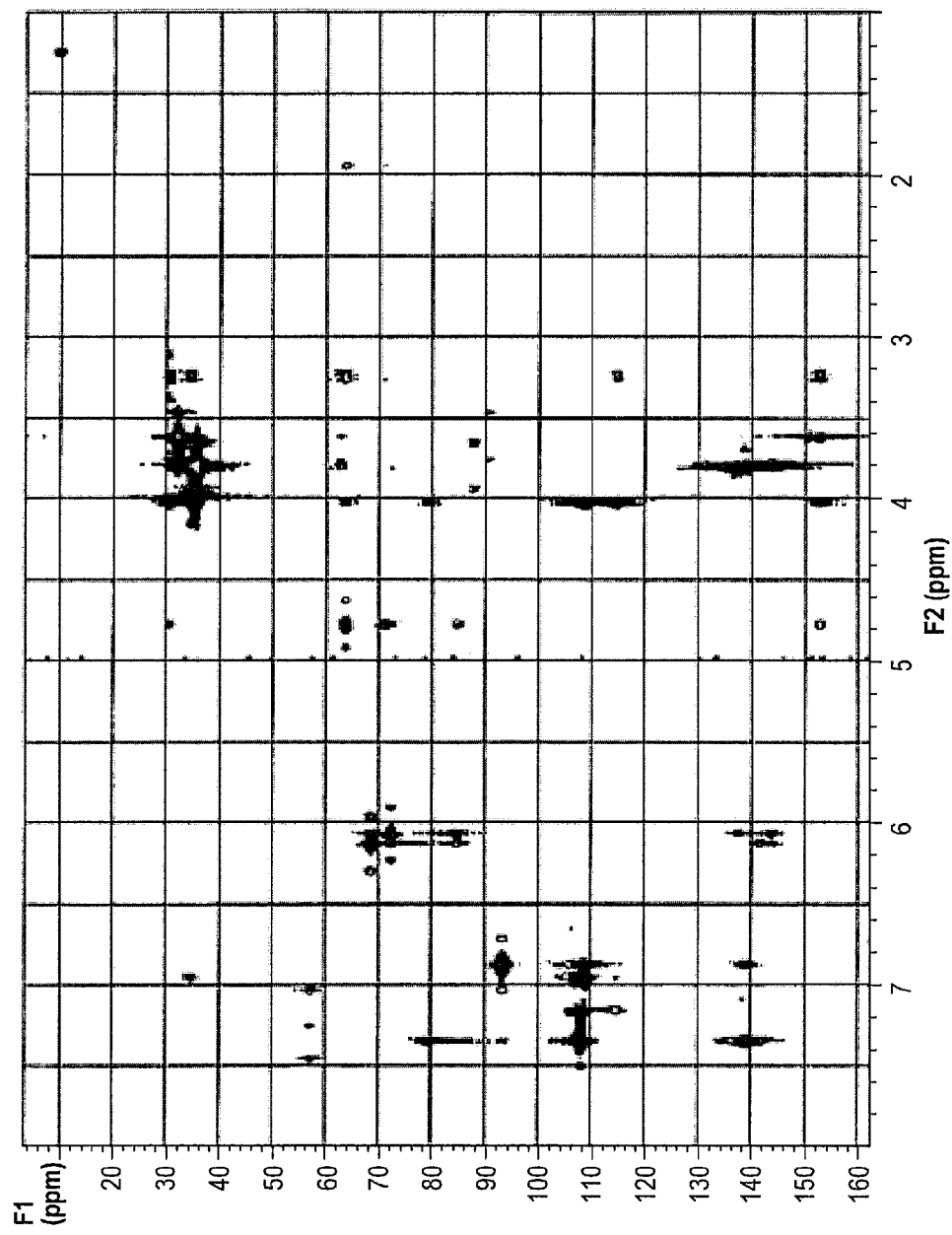
FIG. 17 shows the HMBC spectrum of synthetic exo methyl rocaglate 29 (500 MHz, CHCl$_3$, 25° C.).
Figure 18:
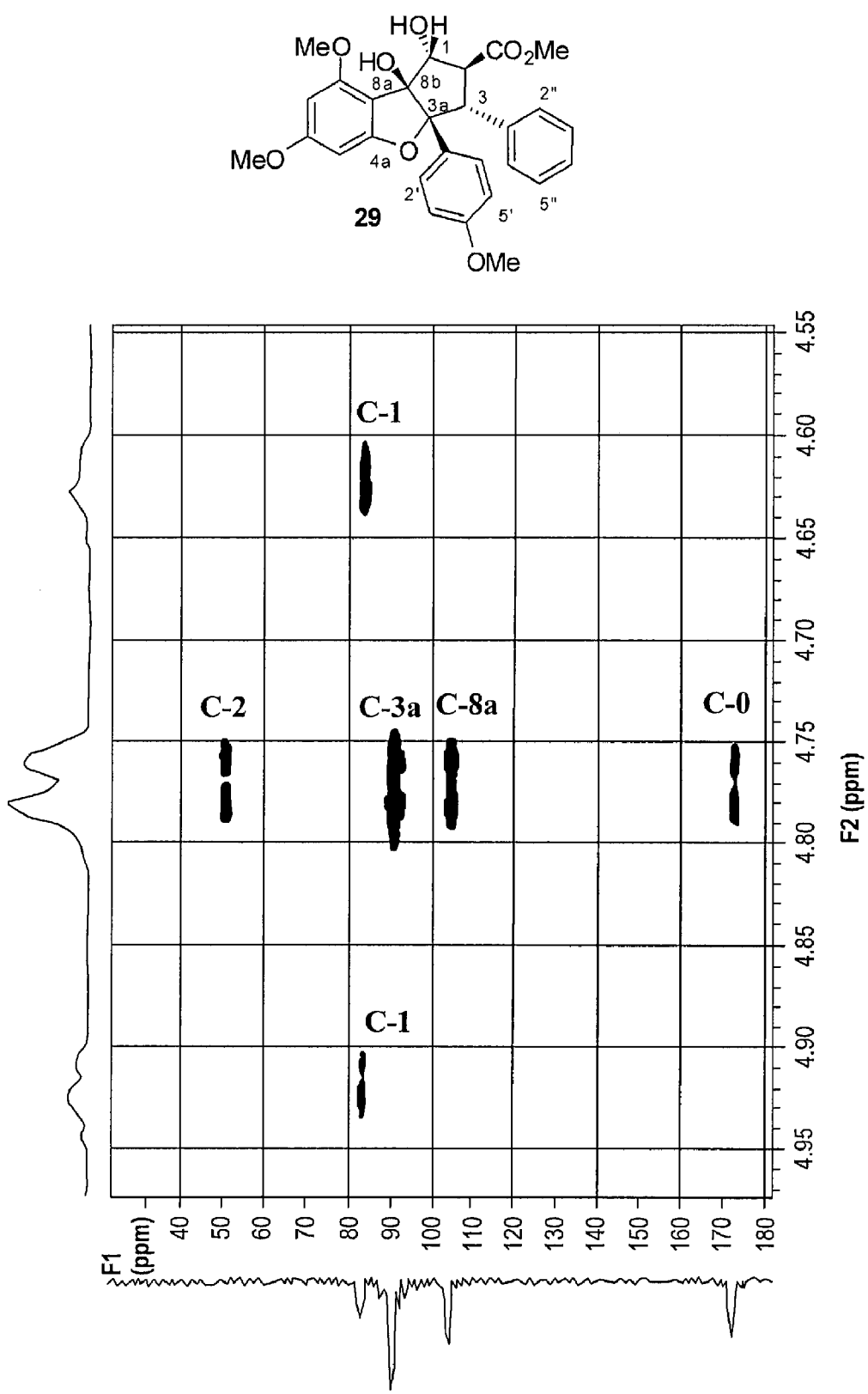
FIG. 18 shows the HMBC spectrum of synthetic exo methyl rocaglate 29 (500 MHz, CHCl$_3$, 25° C.).

Hydroxyl-directed reduction of keto rocaglate 27, which is described in Example 7, afforded (±)-methyl rocaglate 28 (51%) and the corresponding exo stereoisomer 29 (27%) (B. Trost et al., J. Am. Chem. Soc., 1990, 112: 9022-9024). The $^1$H-NMR and $^{13}$C-NMR spectra of compounds 28 and 29 are reported in FIG. 14 and FIG. 15, respectively. Spectral data for synthetic compound 28 were in full agreement with those reported for natural methyl rocaglate (F. Ishibashi et al., Phytochemistry, 1993, 32: 307-310) (see Example 7). Similarly, spectral data for synthetic 29 were in full agreement with those reported for natural methyl rocaglate (G. A. Kraus and J. O. Sy, J. Org. Chem., 1989, 54: 77-83).

Methyl cinnamate was used as dipolarophile in most of the experiments reported herein. However, as will be appreciated by those skilled in the art, any dipolarophile exhibiting reactivity toward a photochemically generated oxidopyrylium species can be used in the practice of the synthetic methods disclosed herein.

III. Chemical Modifications of Aglain/Rocaglamide/Forbaglin Derivatives

As will be appreciated by those of ordinary skill in the art, initially formed aglain derivatives as well as the forbaglins and rocaglamides derived from them can be further chemically modified to obtain new derivatives of the aglain/rocaglamide/forbaglin family.

For example, chemical modifications may be performed to study structure-activity relationships with the goal of developing compounds that possess improved biological activity and that fulfill all stereoelectronic, physicochemical, pharmacokinetic, and toxicologic factors required for clinical usefulness. In such studies, molecular structure and biological activity are correlated by observing the results of systemic structural modification on defined biological endpoints. For example, comparison of the activity of structurally-related compounds may help identify positions and/or chemical motifs that play an important role in biological activity. Similarly, analysis of the effects of the stereochemistry (i.e., the arrangement of atoms in space) of these chemically modified compounds on biological endpoints may help identify conformations that are favorable to the biological activity. The present invention is intended to encompass chemically modified derivatives of the aglain/rocaglamide/forbaglin family obtained by the methods disclosed herein.

Figure 19:
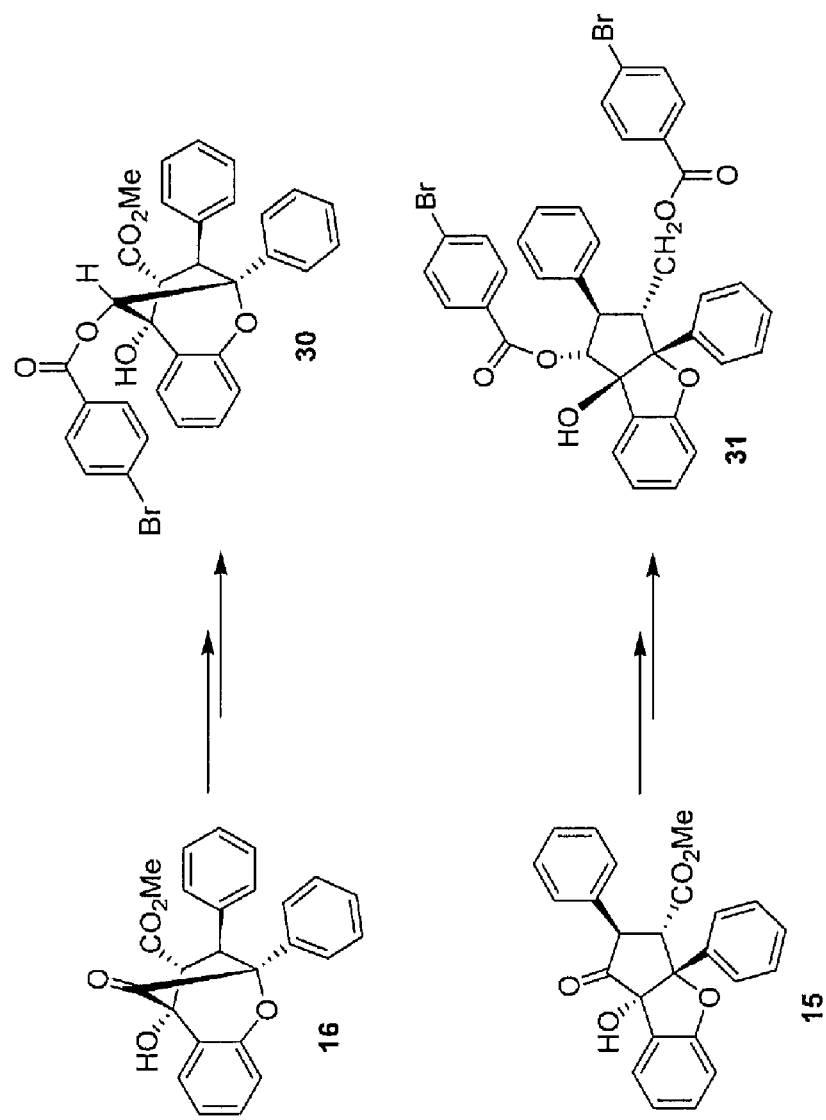
FIG. 19 shows the chemical structures of compounds 30 and 31, obtained from chemical modifications of compounds 16 and 15, respectively.

Examples of such chemical modifications are described in Examples 8 and 9 in the case of compounds 16 and 15, respectively. The chemical structures of the products of these chemical modifications (compound 30 and compound 31, respectively) are shown on FIG. 19.

IV. Uses of Aglain/Rocaglamide/Forbaglin Derivatives

As mentioned above, compounds in the rocaglamide/aglain/forbaglin family have been demonstrated to exhibit biological activity. In particular, a number of these compounds are potent natural insecticides (B. W. Nugroho et al., Phytochemistry, 1997, 45: 1579-1585; B. W. Gussregen et al., Phytochemistry, 1997, 44: 1455-1461; G. Brader et al., J. Nat. Prod., 1998, 61: 1482-1490; J. Hiort Chaidir et al., Phytochemistry, 1999, 52: 837-842; B. W. Nugrobo et al., Phytochemistry, 1999, 51: 367-376).

Moreover, rocaglamide derivatives have been found to exhibit cytostatic activity in human cancer cell lines (B. Cui et al., Tetrahedron, 1997, 53: 17625-17632; T. S. Wu et al., J. Nat. Prod., 1997, 60: 606-608; S. K, Lee et al., Chem. Biol. Interact., 1998, 115: 215-228) with effects comparable to those observed with established anticancer drugs such as vinblastine sulfate and actinomycin D (F. I. Bohnenstengel et al., Z. Naturforsch. [α], 1999, 54: 55-60; F. I. Bohnenstengel et al., Z. Naturforsch. [α], 1999, 54: 1075-1083). In particular, the rocaglate silvestrol 2 (see FIG. 1) has been shown to display cytotoxic activity against human cancer cells comparable to the anticancer drug Taxol (B. Y. Hwang et al., J. Org. Chem., 2004, 69: 3350-3358). Other studies have revealed that these compounds block cell cycle progression and induce apoptosis at nanomolar concentrations in colorectal tumor cell lines (B. Hausott et al, Int. J. Cancer, 2004, 109: 933-940). Experimental results reported in this study suggest that apoptosis is induced via a p38-mediated stress pathway (B. Hausott et al, Int. J. Cancer, 2004, 109: 933-940). Furthermore, rocaglamides have been demonstrated to block protein biosynthesis (T. Ohse et al., J. Nat. Prod., 1996, 650-653) and to induce growth arrest in the G2/M phase in certain tumor cells (F. I. Bohlienstengel et al., Z. Naturforsch. [α], 1999, 54: 1075-1083).

More recently, it was shown that rocaglamides represent highly potent and specific inhibitors of TNF-α (tumor necrosis factor-alpha) and PMA (porbol 12-myristate 13 acetate)-induced NF-κB (nuclear factor-kappa B) activity in different mouse and human T cell lines. The $IC_{50}$ values observed for rocaglamide derivatives were in the nanomolar range whereas aglain derivatives proved inactive. Rocaglamide and several of its derivatives are among the strongest inhibitors of NF-κB-induced gene activation known so far (B. Baumann et al., J. Biol. Chem., 2002, 277: 44791-44800).

Agents that can suppress NF-κB activation have, in principle, the potential to prevent or delay onset or treat NF-κB-linked diseases. On activation, NF-κ-B induces the expression of more than 200 genes, that have been shown to suppress apoptosis, induce cellular transformation, proliferation, invasion, metastasis, chemoresistance, radioresistance, and inflammation (A. Garg and B. B. Aggarwal, Leukemia, 2002, 16: 1053-1056). The activated form of NF-κB has been found to mediate cancer (A. Garg and B. B. Aggarwal, Leukemia, 2002, 16: 1053-1056; A Lin and M. Karin, Semin. Cancer Biol., 2003, 13: 107-114; R. Z. Orlowski and A. S. Baldwin, Trends Mol. Med., 2002, 8: 385-389), atherosclerosis (G. Valen et al., J. Am. Coll. Cardiol., 2001, 38: 307-314), myocardial infarction (W. K. Jones et al., Cardiovasc. Toxicol., 2003, 3: 229-254), diabetes (S. E. Shoelson et al., Int. J. Obes. Relat. Metab. Disord., 2003, 27(Suppl. 3): S49-52), allergy (L. Yang et al., J. Exp. Med., 1998, 188: 1739-1750; J. Das et al., Nature Immunol., 2001, 2: 45-50), asthma (R. Gagliardo et al., Am. J. Respir. Crit. Care Med., 2003, 168: 1190-1198), arthritis (A. K. Roshalk et al., Curr. Opin. Pharmacol., 2002, 2: 316-321), Crohn's disease (D. A. van Heel et al., Hum. Mol. Genet., 2002, 11: 1281-1289), multiple sclerosis (C. J. Huang et al., Int. J. Dev. Neurosci., 2002, 20: 289-296), Alzheimer's disease (M. P. Mattson and S. Camandola, J. Clin. Invest., 2001, 107: 247-254; B. Kaltschmidt et al., Proc. Natl. Acad. Sci. USA, 1997, 94: 2642-2647), osteoporosis, psoriasis, septic shock, AIDS and other inflammatory diseases (J. R. Burke, Curr. Opin. Drug Discov. Devel., 2003, 6: 720-728; Y. Yamamoto and R. B. Gaynor, Curr. Mol., Med., 2001, 1: 287-296; Y. Yamamoto and R. B. Gaynor, J. Clin. Invest., 2001, 107: 135-142).

Interestingly, a synthetic derivative of the natural product rocaglaol was recently found to exhibit neuroprotective activity in vitro and in animal models of Parkinson's disease and traumatic brain injury (T. Falirig et al., Mol. Pharmacol., (Fast Forward" publications), Feb. 16, 2005). Experimental data reported in this study suggest that by inhibiting NF-κB and AP-1 (activator protein-1) signaling, this rocaglaol derivative is able to reduce tissue inflammation and neuronal cell death resulting in significant neuroprotection in animal models of acute and chronic neurodegeneration.

Accordingly, another aspect of the present invention relates to the use of derivatives of the rocaglamide/aglain/forbaglin family for the manufacture of medicaments for use in the treatment of various disease states, including cancer and cancerous conditions, conditions associated with cellular hyperproliferation, and NF-κB-associated conditions. Preferably, the rocaglamide derivatives used in the manufacture of these medicaments are prepared by the inventive methods disclosed herein.

Cancer and cancerous conditions that can be treated using such medicaments may be selected from the group consisting of leukemia, sarcoma, breast, colon, bladder, pancreatic, endometrial, head and neck, mesothelioma, myeloma, oesophagal/oral, testicular, thyroid, cervical, bone, renal, uterine, prostate, brain, lung, ovarian, skin, liver and bowel and stomach cancers, tumors and melanomas. Conditions associated with cellular hyperproliferation that can be treated using the inventive medicaments may be selected from the group consisting of atherosclerosis, restenosis, rheumatoid arthritis, osteoarthritis, inflammatory arthritis, psoriasis, periodontal disease and virally induced cellular hyperproliferation. NF-κB associated conditions that can be treated using the medicaments disclosed herein may be selected from the group consisting of immunological disorders, septic shock, transplant rejection, radiation damage, reperfusion injuries after ischemia, arteriosclerosis and neurodegenerative diseases.

The medicaments according to the present invention may be in a liquid, aerosol or solid dosage form, and may be manufactured into any suitable formulation including, but not limited to, solutions, suspensions, micelles, emulsions, microemulsions, syrups, elixirs aerosols, ointments, gels suppositories, capsules, tablets, pills, dragees, and the like, as will be required for the appropriate route of administration.

Any suitable route of administration of the inventive medicaments is encompassed by the present invention including, but not limited to, oral, intravenous, intraperitoneal, intramuscular, subcutaneous, inhalation, intranasal, topical, rectal or other administration route known in the art. The route of administration, formulation and dosage of the medicament will be dependent upon a variety of factors including the pathophysiological condition to be treated and the severity and/or extent of the disorder, the age, sex, weight and general health of the particular patient, the potency, bioavailability, in vivo half-life and severity of the side effects of the specific rocaglamide derivative(s) employed in the manufacture of the medicament, the time of administration, the duration of the treatment, drugs used in combination or coincidental with the specific rocaglamide derivative(s) employed, and similar factors well known in the art. These factors are readily determined in the course of therapy. Alternatively or additionally, the dosage to be administered can be determined from studies using animal models for the particular condition to be treated, and/or from animal or human data obtained for compounds which are known to exhibit similar pharmacological activities. A medicament may be formulated in such a way that the total dose required for each treatment is administered by multiple dose or in a single dose. In certain embodiments, the medicament is manufactured or formulated in dosage unit form. The expression "dosage unit form", as used herein, refers to a physically discrete unit of medicament appropriate for the condition/patient to be treated.

In certain embodiments, a medicament according to the present invention comprises one or more rocaglamide derivatives as active ingredients. In other embodiments, the medicament further comprises one or more other therapeutic agents. The nature of such additional therapeutic agent(s) will depend on the condition to be treated by administration of the medicament. The ability to determine combinations of compounds suitable to treat particular disorders is well within the capabilities of trained scientists or physicians. For example, a medicament according to the present invention for use in the treatment of cancer may further comprise approved chemotherapeutic drugs, including, but not limited to, alkylating drugs (mechlorethamine, chlorambucil, Cyclophosphamide, Melphalan, Ifosfamide), antimetabolites (Methotrexate), purine antagonists and pyrimidine antagonists (6-Mercaptopurine, 5-Fluorouracil, Cytarabile, Gencitabine), spindle poisons (Vinblastine, Vincristine, Vinorelbine, Paclitaxel), podophyllotoxins (Etoposide, Irinotecan, Topotecan), antibiotics (Doxorubicin, Bleomycin, Mitomycin), nitrosoureas (Carmustine, Lomustine), inorganic ions (Cisplatin, Carboplatin), enzymes (Asparaginase), and hormones (Tamoxifen, Leuprolide, Flutamide, and Megestrol), to name a few. For a more comprehensive discussion of updated cancer therapies see, http://www.nci.nih.gov/, a list of the FDA approved oncology drugs at http://www.fda.gov/cder/cancer/druglistframe.htm, and The Merck Manual, 7th Ed. 1999, the entire contents of which are hereby incorporated by reference.

In addition to the active ingredient(s), the medicament may further comprise one or more pharmaceutically acceptable carriers, including, but not limited to, inert diluents, dispersion media, solvents, solubilizing agents, suspending agents, emulsifying agents, wetting agents, coatings, isotonic agents, sweetening, flavoring and perfuming agents, antibacterial and antifungal agents, absorption delaying agents, and the like. The use of such media and agents for the manufacture of medicaments is well known in the art (see, for example, Remington's Pharmaceutical Sciences, E. W. Martin, 18$^{th}$ Ed., 1990, Mack Publishing Co., Easton, Pa.).

EXAMPLES

The following examples describe some of the preferred modes of making and practicing the present invention. However, it should be understood that these examples are for illustrative purposes only and are not meant to limit the scope of the invention. Furthermore, unless the description in an Example is presented in the past tense, the text, like the rest of the specification, is not intended to suggest that experiments were actually performed or data were actually obtained.

The novel biomimetic approach to the synthesis of rocaglamides, aglains and forbaglins has recently been described, by the Applicants, in a scientific article (B. Gerard et al., J. Am. Chem. Soc., 2004, 126: 13620-13621), which is incorporated herein by reference in its entirety.

General Information

Melting points were recorded on a MeI-Temp (Laboratory Devices). Yields refer to chromatographically and spectroscopically pure materials, unless otherwise stated. Methylene chloride, acetonitrile, methanol, and benzene were purified by passing through two packed columns of neutral alumina (Glass Contour, Irvine, Calif.). 3-Hydroxyflavone was purchased from Indofine Chemical Company, Inc. (Hillsborough, N.J.).

Nuclear Magnetic Resonance. $^1$H-NMR spectra were recorded at 400 MHz at ambient temperature with CDCl$_3$ as solvent unless otherwise stated. $^{13}$C-NMR spectra were recorded at 75.0 MHz at ambient temperature with CDCl$_3$ as solvent unless otherwise stated. Chemical shifts are reported in parts per million (ppm) relative to CDCl$_3$ ($^1$H, δ 7.24; $^{13}$C, δ 77.0) or acetone-d$_6$ ($^1$H, δ2.04; $^{13}$C, δ 207.6, 30.0). Data for $^1$H-NMR are reported as follows: chemical shift, integration, multiplicity (abbreviations are as follows: app=apparent, par obsc=partially obsclue, ovrlp=overlapping, s=singlet, d=doublet, t=triplet, q=quartet, m=multiplet) and coupling constants. All $^{13}$C-NMR spectra were recorded with complete proton decoupling.

Infrared Spectroscopy. Infrared spectra were recorded on a Nicolet Nexus 670 FT-IR spectrophotometer. Low and high-resolution mass spectra were obtained at the Boston University Mass Spectrometry Laboratory using a Finnegan MAT-90 spectrometer.

Chromatography. HPLC analyses were carried out on an Agilent 1100 series HPLC (CHIRALCEL OD, Column No. OD00CE-AI015 and Agilent Zorbax SB-C18). Analytical thin layer chromatography was performed using 0.25 mm silica gel 60-F plates; and flash chromatography, using 200-400 mesh silica gel (Scientific Absorbents, Inc.).

Photochemical Irradiation. Photochemical irradiation experiments were performed using a Hanovia 450 W medium pressure mercury lamp housed in a water-cooled quartz immersion well or using an ethylene glycol cooling system (Neslab, RTE-140). Pyrex test tubes (16×100 mm) were mounted on a support approximately 0.5 cm from the immersion well lamp. An uranium filter was obtained from James Glass (Hanover, Mass.).

All other reactions were carried out in oven-dried glassware under an argon atmosphere unless otherwise noted.

Example 1

Photochemical Irradiation of 3-Hydroxyflavone

Irradiation of 3-Hydroxyflavone in the Presence of Methyl Cinnamate

To a (16×100 mm) test tube was added 3-hydroxyflavone 13 (400 mg, 1.7 mmol) and methyl cinnamate 14 (650 mg, 4 mmol) in 8 mL of anhydrous acetonitrile. After degassing with argon for 5 minutes, the mixture was irradiated (Hanovia UV lamp uranium filter, water used for cooling) at room temperature for 2 hours. The solution was concentrated in vacuo to afford a pink-yellow oil.

Purification via flash chromatography (60:40 hexanes/EtOAc) yielded 92 mg (0.23 mmol, 15%) of cyclopenta[b]tetrahydrobenzofuran 15 and 370 mg (0.94 mmol, 56%) of a mixture of cyclopenta[bc]benzopyran 16 and benzo[b]cyclobutapyran-8-one 17 as colorless solid. Compound 17 was quantitatively converted to cyclopenta[bc]benzopyran 16 by thermolysis (EtOAc, 65° C., 4 hours).

Cyclopenta[b]tetrahydrobenzofuran 15. White solid: nip 76-78° C.; IR ν$_{max}$ (film): 3449, 3064, 3033, 2955, 2920, 1740, 1697, 1682, 1596, 1476, 1254, 1223, 755 cm$^{-1}$; $^1$H-NMR (400 MHz, CDCl$_3$) δ 7.46-6.97 (14H, m), 4.48 (1H, d, J=13 Hz), 3.96 (1H, d, J=13 Hz), 3.59 (3H, s), 3.01 (1H, s) ppm; $^{13}$C-NMR (75 MHz, CDCl$_3$): 208.9, 168.8, 159.6, 136.9, 134.9, 132.1, 129.1, 129.0, 128.9, 128.3, 134.9, 132.1, 129.1, 129.0, 128.9, 128.3, 127.9, 126.5, 125.8, 124.8, 122.5, 110.7, 94.0, 87.8, 59.3, 52.4, 52.3 ppm; HRMS (EI) m/z calculated for C$_{25}$H$_{20}$O$_5$, 400.1311; found, 401.1429 (M+H).

Cyclopenta[bc]benzopyran 16. White solid: mp 78-81° C.; IR ν$_{max}$ (film): 3452, 3060, 3033, 2940, 1767, 1736, 1608, 1584, 1483, 1452, 1210, 905 cm$^{-1}$; $^1$H-NMR (400 MHz, CDCl$_3$) δ 7.34-7.82 (14H, m), 4.631 (1H, d, J=9.2 Hz), 3.645 (1 H, d, J=9.2 Hz), 3.606 (3H, s), 3.57 (1H, s) ppm; $^{13}$C-NMR (75 MHz, CDCl$_3$) δ 208.4, 170.1, 150.9, 138.2, 133.4, 130.8, 129.8, 128.9, 128.7, 128.4, 128.0, 127.9, 127.5, 127.4, 127.3, 126.8, 126.6, 124.9, 122.1, 116.1, 85.1, 79.8, 57.0, 54.2, 52.8 ppm; HRMS (CI/NH$_3$) m/z calculated for C$_{25}$H$_{20}$O$_5$, 400.1311; found, 401.1357 (M+H).

Benzo[b]cyclobutapyran-8-one 17. White solid: mp 68-70° C.; IR ν$_{max}$ (film): 3448, 2922, 2851, 1743, 1597, 1558, 1475, 1248, 1055, 998, 965, 755 cm$^{-1}$; $^1$H-NMR (400 MHz, CDCl$_3$) δ 7.63-7.61 (2H, m), 7.25-6.95 (12H, m), 4.25 (1H, d, J=8.8 Hz), 3.74 (1H, d, J=8.8 Hz), 3.55 (3H, s), 3.27 (1H, s) ppm; $^{13}$C-NMR δ 190.33, 169.6, 151.5, 139.4, 135.4, 130.2, 129.9, 128.9, 128.7, 128.4, 128.1, 127.8, 127.5, 127.4, 126.8, 124.9, 124.6, 121.3, 116.5, 97.5, 88.6, 60.9, 54.3, 52.4 ppm; HRMS (CI/NH$_3$) m/z calculated for C$_{25}$H$_{20}$O$_5$, 400.1311; found, 401.1357 (M+H).

Example 2

Conversion of Cycloadduct 16 to a Forbaglin Ring System 50 mg of cyclopenta[bc]benzopyran 16 (0.125 mmol, 1 equiv) were dissolved in a mixture of methanol (30%) and benzene (0.9 mL/2.1 mL). Pb(OAc)$_4$ (55 mg, 0.125 mmol, 1 equivalent) was then added portionwise at room temperature and the reaction was stirred for 30 minutes at room temperature. After removal of the solvent in vacuo, the resulting residue was diluted with water (5 mL) and EtOAc (5 mL). After separation of the organic layer, the aqueous layer was further extracted twice with EtOAc (5 mL). The organic extracts were combined, washed with brine, dried over MgSO$_4$, filtered, and concentrated in vacuo. Purification on silica gel (20% EtOAc in hexane) afforded 46 mg (0.11 mmol, 85%) of 18:19 as a colorless solid (2:1 mixture of keto/enol tautomers.

Benzo[b]oxepines 18/19. Colorless solid: n/p 178-181° C.; IR $\nu_{max}$ (film): 3060, 3033, 2959, 2924, 1759, 1747, 1684, 1602, 1444, 1434, 1308, 1244; 1102 cm$^{-1}$; $^1$H-NMR (400 MHz, CDCl$_3$) δ 7.64-7.62 (2H, d, J=7.2 Hz), 7.44-7.28 (8H, m), 7.18-7.16 (4H, m), 5.12 (1H, d, J=10 Hz), 4.41 (1H, d, J=10 Hz), 3.66 (3H, s), 3.16 (3H, s) ppm; $^{13}$C-NMR (75 MHz, CDCl$_3$) δ 193.2, 156.7, 154.2, 139.0, 134.8, 132.4, 129.2, 129.1, 128.9, 128.7, 128.3, 128.2, 127.8, 127.7, 127.6, 127.4, 126.9, 126.7, 122.3, 121.9, 121.8, 121.6, 64.9, 52.5, 52.2, 52.0, 51.8, 49.8, 46.7 ppm; HRMS (CI/NH$_3$) m/z calculated for C$_{26}$H$_{22}$O$_6$, 430.1416; found, 431.1516 (M+H).

Example 3

Conversion of Cycloadduct 16 to a Dehydrorocaglate Ring System

To a solution of cyclopenta[bc]benzopyran 16 (50 mg, 0.125 mmol, 1 equivalent) in MeOH (3 mL) at room temperature was added a solution of NaOMe (17 mg, 0.31 mmol, 2.5 equivalents) in MeOH (1 mL) at room temperature. The resulting solution was stirred for 40 minutes at 65° C. After quenching the reaction with saturated NH$_4$Cl at room temperature, 10 mL of EtOAc was added. The organic layer was separated and washed with water (2×5 mL) and brine (5 mL), dried over MgSO$_4$, filtered, and concentrated in vacuo. Purification on silica gel (20% EtOAc in hexane) afforded 45 mg (0.11 mmol, 90%) of the corresponding rocaglates 20/21 as a white solid.

Cyclopenta[b]tetralydrobenzofurans 20/21. White solid: mp 141-143° C. IR $\nu_{max}$ (film): 3066, 3027, 2954, 2923, 2856, 1758, 1730, 1650, 1594, 1454, 1279, 1247, 1146, 975 cm$^{-1}$; $^1$H-NMR (400 MHz, CDCl$_3$, 1:1 mixture of keto/enol tautomers 20:21) δ 7.52-6.88 (28H, m), 5.28 (1H, s), 4.13 (2H, dd, J=13.6 Hz), 3.63 (3H, s), 3.57 (3H, s), 2.66 (1H, s), 2.10 (1H, s) ppm; $^{13}$C NMR (75 MHz, CDCl$_3$) δ 204.3, 167.1, 159.8, 132.6, 131.1, 128.8, 128.0, 127.8, 127.7, 127.6, 127.6, 127.3, 127.2, 126.9, 126.8, 126.6, 126.2, 125.3, 124.8, 122.6, 121.8, 119.5, 112.4, 110.6, 98.7, 57.4, 56.7, 55.8, 52.9, 51.7 ppm; HRMS (EI) m/z calculated for C$_{25}$H$_{20}$O$_5$, 400.1 311; found, 401.1427 (M+H).

To a solution of NaH (washed with 3×10 mL hexanes, 5 mg, 0.21 mmol, 2.1 equivalents) in THF (2 mL) was added a solution of cyclopenta[bc]benzopyran 16 (40 mg, 0.10 mmol, 1 equivalent) in THF (1 mL) at room temperature. The resulting yellow solution was stirred at room temperature for 30 minutes. After addition of thionyl chloride (15 μL, 0.21 mmol, 2.1 equivalents) at room temperature, the mixture was stirred for another hour and then quenched with saturated aqueous NaHCO$_3$. 10 mL of EtOAc were then added and the organic layer was washed with 2×3 mL of water and 3 mL brine. The organic extracts were dried over MgSO$_4$, filtered, and concentrated in vacuo. Purification on silica gel (5% EtOAc in hexane) afforded 21 mg (0.048 mmol, 48%) of the corresponding 1,3,2-dioxathiolane 22 as a yellow oil.

1,3,2-Dioxathiolane 22. Yellow oil: IR $\nu_{max}$ (film): 3025, 2948, 2913, 1716, 1650, 1553, 1243, 1200, 746 cm$^{-1}$. $^1$H-NMR (400 MHz, CDCl$_3$) δ 7.46-7.07 (14H, m), 3.85 (1H, s), 3.72 (3H, s) ppm; $^{13}$C-NMR δ 190.4, 165.4, 144.9, 143.1, 132.9, 132.6, 130.8, 130.3, 130.0, 129.6, 129.2, 128.8, 128.7, 128.5, 128.1, 125.6, 124.7, 122.6, 111.1, 52.6, 52.4 ppm; HRMS (EI) m/z calculated for C$_{25}$H$_{18}$O$_6$S, 446.0824; found, 447.0805 (M+H).

Example 4

Conversion of Dehydrorocaglate Ring System to Rocaglate Ring System

To a solution of 197 mg (0.75 mmol, 6 equivalents) of Me$_4$NBH(OAc)$_3$ and 68 μL (1.25 mmol, 10 equivalents) of acetic acid in 3 mL of CH$_3$CN was added a solution of 50 mg (0.12 mmol, 1 equivalent) of keto rocaglate 20 in 1 mL of CH$_3$CN. The resulting yellow solution was stirred for 12 hours at room temperature before being quenched with 2 mL of saturated NH$_4$Cl solution. The solution was then treated with 1 mL of a 3 M aqueous solution of sodium/potassium tartrate and stirred at room temperature for 30 minutes. The aqueous solution was extracted with CH$_2$Cl$_2$ (2×5 mL). The combined organic layers were washed with brine, dried over MgSO$_4$, filtered, and concentrated in vacuo. Purification on silica gel (20% EtOAc in hexane) afforded 30 mg (0.047 mmol, 95%) of 23 as a white solid.

Cyclopenta[b]tetrahydrobenzofuran 23. White solid: mp 176-178° C.; IR $\nu_{max}$ (film): 3421, 3031, 2925, 1733, 1600, 1476, 1462, 1249, 1102, 976 cm$^{-1}$; $^1$H-NMR (400 MHz, CDCl$_3$) δ 7.41-6.96 (14H, m), 4.84 (1H, d, J=6 Hz), 4.50 (1H, d, J=13.6 Hz), 3.99 (1H, dd, J=6, 13.6 Hz), 3.66 (3H, s), 2.55 (1H, s), 1.82 (1H, s), ppm; $^{13}$C-NMR (75 MHz, CDCl$_3$) δ 171.5, 159.1, 136.8, 134.5, 131.4, 127.9, 127.7, 127.6, 127.5, 127.4, 126.8, 126.5, 126.3, 121.6, 111.0, 100.8, 93.3, 79.2, 56.0, 52.2, 50.8 ppm; LRMS (ESI+) m/z calculated for C$_{25}$H$_{22}$O$_5$, 402.1467; found, 403.0 (M+H).

Example 5

Photochemical Irradiation of Methoxy-Substituted 3-Hydroxyflavone

Synthesis of Trimethoxy-Substituted 3-Hydroxyflavone
Trimethoxy-substituted 3-hydroxyflavone 24 was synthesized following a procedure adapted from a reaction sequence reported by H. Tanaka and coworkers (Tetrahedron Lett., 2000, 41: 9735-9739). The reaction scheme is presented on FIG. 12.

Irradiation of Trimethoxy-Substituted 3-Hydroxyflavone in the Presence of Methyl Cinnamate
To a (16×100 mm) test tube was added with kaempferol derivative 24 (200 mg, 0.61 mmol), methyl cinnamate 14 (990 mg, 6.1 mmol), and 20 mL of anhydrous methanol. After degassing with argon, the mixture was irradiated (Hanovia UV lamp, uranium filter) at 0° C. for 12 hours under an argon atmosphere. The solution was concentrated in vacuo to give a yellow oil. Purification via flash chromatography (60:40 hexanes/EtOAc) afforded 100 mg (0.2 mmol, 33%) of the corresponding trimethoxy cyclopenta[bc]benzopyran derivative 25 (mixture of endo/exo cycloadducts) as a white solid and 50 mg (0.1 mmol, 17%) of benzo[b]cyclo-butapyran-8-one derivative 26 as a yellow solid.

Trimethoxy Cyclopenta[bc]benzopyran 25. White solid: mp 83-85° C. IR $v_{max}$ (film): 3475, 3013, 2943, 2832, 1786, 1737, 1611, 1590, 1510, 1450, 1255, 1146, 1094, 828 cm$^{-1}$; $^1$H-NMR (400 MHz, CDCl$_3$) δ 7.54-7.52 (2H, d, J=8.8 Hz), 7.25-7.23 (2H, d, J=8.8 Hz), 7.17-7.49 (2H, m), 7.10-7.04 (6H, m), 6.85-6.82 (2H, m), 6.64-6.60 (4H, m), 6.19-6.18 (1H, d, J=2 Hz), 6.18-6.17 (1H, d, J=2 Hz), 6.11-6.10 (1H, d, J=2 Hz), 6.08-6.07 (1H, d, J=2 Hz), 4.49-4.47 (1H, d, J=9.2 Hz), 4.191-4.168 (1H, d, J=9.2 Hz), 3.94 (1H, s), 3.84 (3H, s), 3.83 (3H, s), 3.77 (4H, m), 3.75 (3H, s), 3.71 (3H, s), 3.66 (4H, m), 3.62 (3H, s), 3.55 (3H, s), 3.29 (1H, s) ppm; $^{13}$C-NMR (70 MHz, CDCl$_3$) δ 205.5, 170.7, 170.6, 161.9, 161.3, 158.8, 158.6, 158.4, 153.6, 152.8, 139.9, 138.1, 130.1, 129.8, 128.9, 128.7, 128.2, 127.8, 127.9, 127.0, 126.5, 125.6, 113.6, 112.7, 112.6, 107.7, 106.5, 97.9, 95.5, 94.4, 94.3, 93.6, 93.4, 92.7, 88.7, 83.6, 81.04, 80.7, 62.4, 57.6, 56.1, 55.9, 55.4, 55.3, 55.1, 54.5, 53.4, 52.2, 51.8 ppm; HRMS (CI/NH$_3$) m/z calculated for C$_{28}$H$_{26}$O$_8$, 490.1628; found, 491.1739 (M+H).

Trimethoxy benzo[b]cyclobutapyran-8-one 26. Yellow solid: mp 79-81° C. IR $v_{max}$ (film): 3489, 3006, 2948, 2839, 1734, 1729, 1618, 1590, 1516, 1461, 1437, 1299, 1200, 1148, 1096, 909 cm$^{-1}$; $^1$H-NMR (400 MHz, CDCl$_3$) δ 7.53 (2H, d, J=8.8 Hz), 7.16 (2H, m), 7.01 (3H, m), 6.64 (2H, d, J=8.8 Hz), 6.19 (1H, d, J=2 Hz), 6.08 (1H, d, J=2 Hz), 4.27 (1H, s), 4.17 (1H, d, J=9.6 Hz), 3.84 (4H, m), 3.75 (3H, s), 3.67 (3H, s), 3.56 (3H, s) ppm.

Example 6

Conversion of Aglains 25 and 26 to a Keto Rocaglate Ring System

Conversion of Aglain 25

Figure 13:
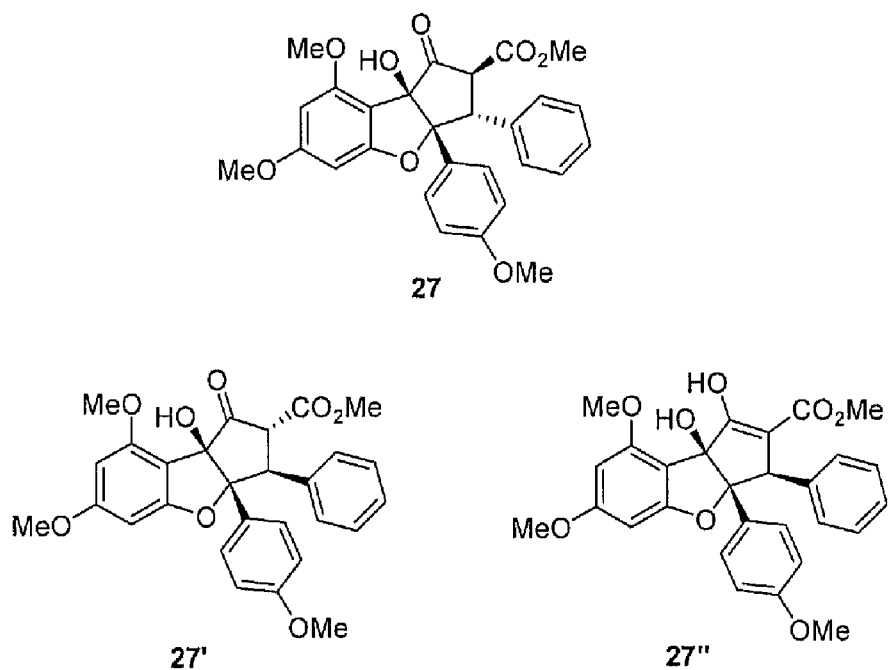
FIG. 13 shows the chemical structures of compound 27, keto isomer 27' and enol isomer 27".

To a solution of aglain 25 (60 mg, 0.12 mmol, 1 equivalent) in MeOH (4 mL) was added a solution of NaOMe (13.2 mg, 0.24 mmol, 2.5 equivalents) in MeOH (1 mL) at room temperature. The resulting solution was stirred for 40 minutes at 65° C. After quenching the reaction with saturated NH$_4$Cl, 10 mL of EtOAc was then added, and the organic layer was washed with water (2×5 mL) and brine (5 mL). The organic layer was dried over MgSO$_4$, filtered, and concentrated in vacuo to afford 57 mg (0.12 mmol, 95%) of crude ketol shift product 27/27'/27" as a yellow oil which was used without further purification (3:1 mixture of endo:exo isomers 27'/27" and 27, see chemical structures of 27, 27', 27" on FIG. 13).

Trimethoxy rocaglate 27/27'/27". Yellow oil: IR $v_{max}$ (film): 3501, 3006, 2947, 2926, 2839, 1762, 1734, 1615, 1513, 1450, 1440, 1255, 1213, 1146, 1033, 1076 cm$^{-1}$; $^1$H-NMR (400 MHz, CDCl$_3$, 1:1 mixture of keto/enol tautomers 27': 27") δ 7.34-7.32 (2H, d, J=6.8 Hz), 7.20-7.19 (2H, m), 7.09-6.86 (15H, m), 6.65 (2H, d, J=8.8 Hz), 6.51 (2H., d, J=6.8 Hz), 6.33 (1H, d, J=1.6 Hz), 6.17 (1H, d, J=1.6 Hz), 6.13 (1H, d, J=1.6 Hz), 6.12 (1H, d, J=1.6 Hz), 6.05 (1H, d, J=1.6 Hz), 6.00 (1H, d, J=1.6 Hz), 4.46 (1H, s), 4.42 (1H, d, J=14.8 Hz), 4.36 (1H, d, J=14.8 Hz), 4.22 (1H, d, J=13.6 Hz), 4.04 (1H, d, 13.6 Hz), 3.84 (3H, s), 3.08-3.79 (9H, m), 3.77 (9H, m), 3.70 (6H, m), 3.64 (6H, m), 3.57 (3H, s), 3.30 (1H, s), 3.01 (1 H, s) ppm; HRMS (EI) m/z calculated for C$_{28}$H$_{26}$O$_8$, 490.1628; found, 490.9634 (M+H).

Conversion of Aglain 26

Benzo[b]cyclobutapyran-8-one 26 was subjected to the aforementioned conditions using 20 mg (0.041 mmol, 1 equivalent) of 26 in MeOH (2 mL) and NaOMe (5 mg, 0.09 mmol, 2.5 equivalents) in MeOH (1 mL). 18 mg of crude ketol shift product 27 (0.036, 90%) was isolated and used without further purification (only the endo isomer was isolated).

Example 7

Hydroxyl-Directed Reduction of Keto Rocaglate 27

Hydroxyl-Directed Reduction of Trimethoxy Keto Rocaglate 27

To a solution of 184 mg (0.70 mmol, 6 equivalents) of Me$_4$NBH(OAc)$_3$ and 63 µL (1.16 mmol, 10 equivalents) of acetic acid in 3 mL of CH$_3$CN was added a solution of 57 mg (0.12 mmol, 1 equivalent) of 27 in 1 mL of CH$_3$CN. The resulting yellow solution was stirred for 12 hours at room temperature before being quenched with 2 mL of saturated NH$_4$Cl. The solution was then treated with 1 mL of a 3 M aqueous solution of sodium/potassium tartrate and stirred at room temperature for 30 minutes. The aqueous solution was extracted with CH$_2$Cl$_2$ (2×5 mL). The combined organic layers were washed with brine, dried over MgSO$_4$, filtered and concentrated in vacuo. Purification on silica gel (40% EtOAc in hexane) afforded 30 mg (0.030 mmol, 51%) of the corresponding endo methyl rocaglate 28 and 18 mg (0.017 mmol, 27%) of the corresponding exo methyl rocaglate 29.

Endo Methyl Rocaglate 28. White solid: nip 92-93° C.; R $v_{max}$ (film): 3013, 2954, 2926, 2853, 1734, 1615, 1517, 1457, 1433, 1262, 1195, 1150, 1031, 832 cm$^{-1}$; $^1$H-NMR (400 MHz, CDCl$_3$) δ 7.09 (2H, d, J=9.2 Hz), 7.05-7.03 (3H, m), 6.84 (2H, m), 6.65 (2H, d, J=9.2 Hz), 6.27 (1H, d, J=2 Hz), 6.1 (1H, d, J=2 Hz), 5.01 (1H, dd, J=6.4, 1.2 Hz), 4.28 (1H, d, J=14.4 Hz), 3.80 (1H, dd, J=14.4, 6.4 Hz), 3.86 (3H, s), 3.82 (3H, s), 3.69 (3H, s), 3.63 (3H, s), 3.50 (1H, s), 1.81 (1H, br) ppm; $^{13}$C-NMR (75 MHz, CDCl$_3$) δ 170.5, 164.1, 160.9, 158.8, 157.0, 137.0, 129.0, 128.4, 127.8, 127.7, 126.5, 112.7, 107.7, 101.9, 93.7, 92.7, 89.5, 79.6, 60.4, 55.8, 55.1, 55.0, 51.9, 50.6 ppm; δ HRMS (CI/NH$_3$) m/z calculated for C$_{28}$H$_{28}$O$_8$, 492.1784; found, 493.1891 (M+H).

Exo Methyl Rocaglate 29. Foamy yellow: solid mp 84-85° C. IR $v_{max}$ (film): 3031, 3006, 2958, 2936, 2846, 1730, 1636, 1430, 1307, 1258, 1132, 103 cm$^{-1}$; $^1$H-NMR (400 MHz, CDCl$_3$) δ 7.34 (2H, d, J=8.8 Hz), 7.17-1.15 (3H, m), 6.95-6.94 (2H, m), 6.87 (2H, d, J=8.8 Hz), 6.12 (1H, d, J=1.6 Hz), 6.06 (1H, d, J=1.6 Hz), 4.76 (1H, dd, J=10.2, 1.6 Hz), 4.02 (1H, d, J=12.8 Hz), 3.82 (3H, s), 3.78 (3H, s), 3.77 (3H, s), 3.60 (3H, s), 3.23 (1H, dd, J=12.8, 10.2 Hz), 1.81 (1H, s) ppm; $^{13}$C-NMR (75 MHz, CDCl$_3$) δ 173.1, 164.1, 162.0, 159.4, 157.9, 135.0, 129.1, 128.4, 128.0, 127.3, 119.7, 113.6, 105.1, 99.5, 92.6, 91.4, 88.8, 83.9, 55.8, 55.8, 55.4, 54.8, 52.3, 50.9 ppm; HRMS (CI/NH$_3$) m/z calculated for C$_{28}$H$_{28}$O$_8$, 492.1784; found, 493.1891 (M+H).

The crude ketol shift product 27 obtained from benzo[b] cyclobutapyran-8-one derivative 26 was subjected to the aforementioned conditions using 58 mg of Me$_4$NBH(OAc)$_3$ (0.22 mmol, 6 equivalents), 20 µL (0.37 mmol, 10 equivalents) in 3 mL of MeCN, and 18 mg (0.037 mmol, 1 equivalent) of compound 26. 13 mg of endo methyl rocaglate 28 (0.021 mmol, 75%) was obtained.

Tables 1, 2, and 3 shown below summarize data comparison of natural (F. Ishibashi et al., Phytochemistry, 1993, 32: 307-310) and synthetic endo methyl rocaglate 28.

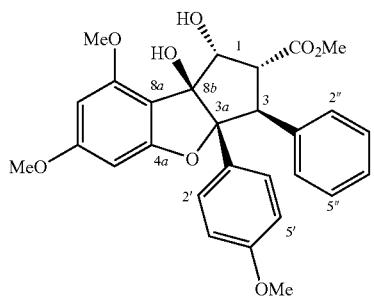

TABLE 1

$^1$H-NMR Data (400 MHz, CDCl$_3$) for natural and synthetic endo methyl rocaglate 28.

| | $^1$H-NMR (400 Hz in CDCl$_3$) | |
|---|---|---|
| Position | Natural | Synthetic 28 |
| 1 | 5.02 (dd, 1.6, 6.8) | 5.01 (dd, 1.2, 6.4) |
| 2β | 3.91 (dd, 6.8, 14.4) | 3.91 (dd, 6.4, 14.4) |
| 3α | 4.32 (d, 14.4) | 4.27 (d, 14.4) |
| 5 | 6.29 (d, 2.4) | 6.26 (d, 2) |
| 7 | 6.13 (d, 2.4) | 6.10 (d, 2) |
| 2', 6' | 7.11 (d, 8.8) | 7.10 (d, 9.2) |
| 3', 5' | 6.68 (d, 8.8) | 6.65 (d, 9.2) |
| 2", 6" | 6.88 (m) | 6.85 (m) |
| 3", 4", 5" | 7.07 (m) | 7.04 (m) |
| OMe-6 | 3.88 (s) | 3.86 (s) |
| OMe-8 | 3.84 (s) | 3.81 (s) |
| OMe-4' | 3.71 (s) | 3.67 (s) |
| CO$_2$Me | 3.65 (s) | 3.62 (s) |
| OH | 1.78, 3.60 (br, s) | 1.88, 3.50 (br, s) |

TABLE 2

$^{13}$C-NMR Data (75 MHz, acetone-d$_6$) for natural and synthetic endo methyl rocaglate 28.

| | $^{13}$C NMR (75 Hz) in acetone d$_6$ | |
|---|---|---|
| Position | Natural | Synthetic 28 |
| 1 | 80.6 | 80.3 |
| 2 | 51.5 | 51.1 |
| 3 | 55.8 | 55.5 |
| 3a | 102.6 | 102.2 |
| 5 | 89.8 | 89.4 |
| 7 | 92.8 | 92.3 |
| 8a | 112.8 | 112.4 |
| 8b | 94.2 | 94.1 |
| 1' | 128.9 | 128.4 |
| 2', 6' | 129.9 | 129.6 |
| 3', 5' | 112.8 | 112.4 |
| 1" | 139.2 | 138.8 |
| 2", 6" | 128.2 | 128.4 |
| 3", 5" | 128.8 | 128.4 |
| 4" | 126.8 | 126.4 |
| 4a, 6, 8, 4' | 158.6, 159.3, 161.7, 164.6 | 158.3, 158.9, 161.4, 164.3 |
| ArOMe | 55.2, 55.9, 56.0 | 54.8, 55.3, 55.5 |
| C=O | 170.7 | 170.4 |
| CO$_2$Me | 51.5 | 51.1 |

TABLE 3

Miscellaneous data for natural and synthetic endo methyl rocaglate 28

| | Natural methyl rocaglate | Synthetic methyl rocaglate 28 |
|---|---|---|
| Mp | 88-91 | 92-93 |
| HRMS (EI), m/z (rel. int.) | 492.1797 [M]$^+$ 492 (3), 390 (6), 313 (46), 300 (100), 285 (59), 181 (66), 135 (78), 131 (50), 103 (55). | 492.1814 [M]$^+$ 492 (2), 390 (5), 313 (40), 300 (100), 285 (23), 181 (21), 135 (16), 131 (24), |
| IR $\nu_{max}$ cm$^{-1}$ (KBr) | 3489, 1750, 1623, 1611, 1513, 1247, 1218, 1200, 1149, 1118 | 3486, 1734, 1615, 1517, 1251, 1212, 1195, 1150, 1115. |

Tables 4 and 5 shown below summarize data comparison of compound 29 and exo methyl rocaglate synthesized by Kraus and Sy (G. A. Kraus and J. O, Sy, J. Org. Chem., 1989, 54: 77-83).

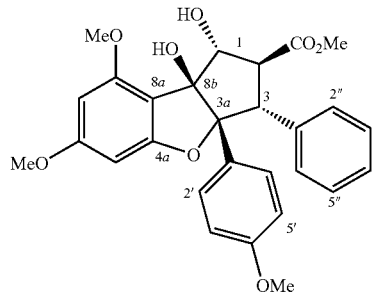

TABLE 4

$^1$H-NMR Data (400 MHz, CDCl$_3$) for Kraus' exo methyl rocaglate and compound 29.

| | $^1$H NMR (400 Hz) in CDCl$_3$ | |
|---|---|---|
| Position | Exo methyl rocaglate | 29 |
| 1 | 4.77 (d, 11) | 4.76 (dd, 1.6, 10.2) |
| 2α | 3.24 (dd, 11, 13) | 3.23 (dd, 10.2, 12.8) |
| 3β | 4.03 (d, 13) | 4.02 (d, 12.8) |
| 5 | 6.12 (d, 2) | 6.12 (d, 1.6) |
| 7 | 6.05 (d, 2) | 6.06 (d, 1.6) |
| 2', 6' | 7.33 (d, 8) | 7.34 (d, 8.8) |
| 3', 5' | 6.87 (d, 8) | 6.87 (d, 8.8) |
| 2", 6" | 6.94 (m) | 6.95 (m) |
| 3", 4", 5" | 7.16 (m) | 7.16 (m) |
| Ar—OMe | 3.81, 3.78, 3.76 | 3.82, 3.78, 3.77 |
| CO$_2$Me | 3.60 | 3.60 |

TABLE 5

$^{13}$C-NMR Data (75 MHz, CDCl$_3$) for Kraus'exo methyl rocaglate and compound 29.

| | $^{13}$C NMR (75 MHz) in CDCl$_3$ | |
|---|---|---|
| Position | Exo methyl rocaglate | Compound 29 |
| 1 | 83.8 | 83.9 |
| 2 | 50.8 | 50.90 |
| 3 | 55.7 | 55.9 |
| 3a | 91.2 | 91.4 |
| 5 | 88.7 | 88.7 |
| 7 | 92.5 | 92.6 |

TABLE 5-continued

13C-NMR Data (75 MHz, CDCl₃)for Kraus'exo methyl rocaglate and compound 29.

| | 13C NMR (75 MHz) in CDCl₃ | |
|---|---|---|
| Position | Exo methyl rocaglate | Compound 29 |
| 8a | 105.0 | 105.1 |
| 8b | 99.3 | 99.5 |
| 1' | 129.0 | 129.1 |
| 2', 6' | missing | 119.6 |
| 3', 5' | 113.5 | 113.6 |
| 1" | 134.8 | 134.9 |
| 2", 6" | 128.3 | 128.4 |
| 3", 5" | 127.8 | 127.9 |
| 4" | 127.1 | 127.3 |
| 4a, 6, 8, 4' | 163.9, 161.9, 159.2, 156.8 | 164.1, 162.0, 159.4, 157.9 |
| ArOMe | 55.7, 55.3, 54.7 | 55.8, 55.4, 54.8 |
| C=O | 172.95 | 173.1 |
| CO₂Me | 52.1 | 52.3 |

Example 8

Reduction of Cyclopenta[bc]benzopyran 16

To a solution of cyclopenta[bc]benzopyran 16 (100 mg, 0.25 mmol, 1 equivalent) in 10 mL of MeOH was added sodium borohydride (15 mg, 0.375 mmol, 1.5 equivalent) portionwise over 5 minutes at 0° C. The resulting solution was warmed to room temperature and stirred for 4 hours. The reaction was then quenched with saturated NH₄Cl, and diluted with EtOAc (10 mL) and water (10 mL). After separation of the organic layer, the aqueous layer was extracted twice with EtOAc (5 mL). The organic extracts were combined, washed with brine, dried over MgSO₄, filtered, and concentrated in vacuo.

The resulting diol (75 mg, 0.18 mmol, 1 equivalent) was directly subjected to acylation using 4-bromobenzoyl chloride (94 mg, 0.43 mmol, 1.2 equivalent) and DMAP (44 mg, 0.36 mmol, 2 equivalents) in 3 mL of CH₂Cl₂. The reaction was stirred at room temperature for 24 hours. The reaction mixture was diluted using CH₂Cl₂ (5 mL) and washed with water (2×5 mL). The organic layer was washed with brine, dried over MgSO₄, filtered, and concentrated in vacuo. Purification on silica gel (30% EtOAc in hexane) provided 95 mg (0.16 mmol, 85%) of 4-bromobenzoate 30 as a colorless solid.

4-Bromobenzoate 30. Colorless solid: mp 73-74 (benzene); IR $\nu_{max}$ (film): 3468, 3065, 3032, 2952, 2926, 2854, 1725, 1612, 1590, 1484, 1458, 1269, 911, 754; 1H-NMR (400 MHz, CDCl₃) δ 7.46-7.43 (2H, d, J=10.2 Hz), 7.28-7.19 (6H, m), 7.00-6.90 (10H, m), 6.47 (1H, s), 4.20-4.18 (1H, s, 8.4 Hz), 3.80 (1H, s), 3.63-3.61 (1H, d, J=8.4 Hz), 3.48 (3H, s) ppm; 13C-NMR (75 MHz, CDCl₃) δ 170.4, 166.2, 152.0, 139.2, 136.4, 131.7, 131.5, 129.9, 129.2, 128.8, 128.2, 127.9, 127.8, 127.7, 126.9, 126.5, 124.8, 123.6, 120.9, 115.7, 87.8, 77.8, 73.8, 60.5, 55.3, 52.4 ppm; HRMS (CI/NH₃) m/z calculated for $C_{32}H_{25}BrO_6$, 584.0835; found, 585.0931 (M+H).

Figure 20:
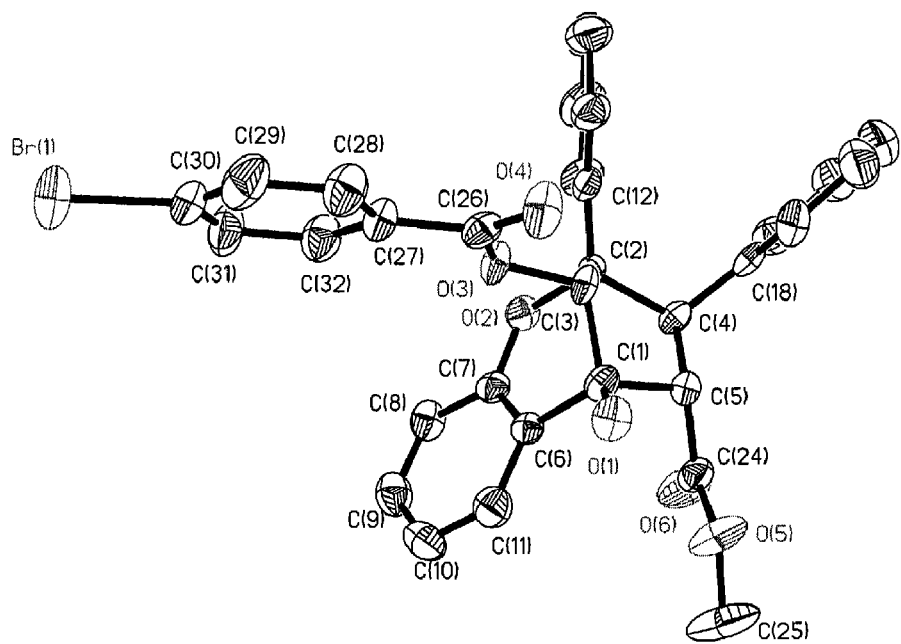
FIG. 20 shows the X-ray Crystal Structure of Compound 30.

The X-ray crystal structure of compound 30 is presented on FIG. 20.

Crystals of compound 30 suitable for X-ray analysis were obtained by slow evaporation from benzene. Crystallographic data have been deposited with the Cambridge Crystallographic Data Centre (CCDC 248425). Copies of the data can be obtained free of charge on application to the CCDC, (12 Union Road, Cambridge CB21EZ, UK; Fax: (+44)-1223-336-033; e-mail: deposit@ccdc.cam.ac.uk).

Crystal data and structure refinement for compound 30 are presented in Table 6.

TABLE 6

Crystal data and structure refinement for compound 30.

| Identification code | Compound 30 |
|---|---|
| Empirical formula | C50 H43 Br O6 |
| Formula weight | 819.75 |
| Temperature | 213(2) K |
| Wavelength | 0.71073 Å |
| Crystal system | Monoclinic |
| Space group | P2(1)/c |
| Unit cell dimensions | a = 12.027(2) Å   α = 90°. |
| | b = 27.228(5) Å   β = 95.966(4)° |
| | c = 12.927(2) Å   γ = 90° |
| Volume | 4210.2(13) Å³ |
| Z | 4 |
| Density (calculated) | 1.293 Mg/m³ |
| Absorption coefficient | 1.026 mm⁻¹ |
| F(000) | 1704 |
| Crystal size | 0.10 × 0.08 × 0.08 mm³ |
| Theta range for data collection | 1.70 to 25.00°. |
| Index ranges | −14 <= h <= 14, −32 <= k <= 26, −12 <= l <= 15 |
| Reflections collected | 22422 |
| Independent reflections | 7405 [R(int) = 0.1260] |
| Completeness to theta = 25.00° | 99.9% |
| Absorption correction | None |
| Refinement method | Full-matrix least-squares on F² |
| Data/restraints/parameters | 7405/0/516 |
| Goodness-of-fit on F² | 0.998 |
| Final R indices [I > 2sigma(I)] | R1 = 0.0655, wR2 = 0.1101 |
| R indices (all data) | R1 = 0.2038, wR2 = 0.1455 |
| Largest diff. peak and hole | 0.504 and −0.513 e · Å⁻³ |

Example 9

Reactivity of Cyclopenta[bc]benzopyran 15

To a solution of lithium aluminium hydride (26 mg, 0.89 mmol, 3 equivalents) in THF (5 mL) at 0° C. was added a solution of cyclopenta[b]tetrahydrobenzofuran 15 (90 mg, 0.225 mmol, 1 equivalent) in 2 mL of THF. The resulting solution was warmed to room temperature and stirred for 3 hours. The reaction was then cooled at 0° C. and quenched with 1 mL of water followed by 1 mL of 1 N aqueous NaOH. The resulting solution was filtered and the filtrate was evaporated in vacuo to afford the crude triol (63 mg, 0.17 mmol, 75%).

The crude triol was then directly subjected to acylation with 4-bromobenzoyl chloride (82 mg, 0.34 mmol, 2.2 equivalents) and DMAP (63 mg, 0.51 mmol, 3 equivalents) in 5 mL of CH₂Cl₂. The reaction was then stirred for 24 hours at room temperature. The mixture was diluted using CH₂Cl₂ (5 mL) and washed with water (2×5 mL). The organic layer was washed with brine, dried over MgSO₄, filtered, and concentrated in vacuo. Purification on silica gel (30% EtOAc in hexane) afforded 100 mg (0.14 mmol, 80%) of bis-4-bromobenzoate 31 as a colorless solid, Bis-4-bromobenzoate 31. Colorless solid: mp 256-257° C. (petroleum ether/chloroform); IR $\nu_{max}$ (film): 3420, 3035, 2956, 2870, 1717, 1701, 1590, 1475, 1465, 1398, 1365, 1271, 1216, 1125 cm⁻¹; 1H-NMR (400 MHz, CDCl₃) δ 7.70-7.68 (2H, d, J=8.4 Hz), 7.59-7.56 (2H, d, J=8.4 Hz), 7.51-7.48 (2H, d, J=8.4 Hz), 7.40-7.18 (14H, m), 6.98-6.59 (2H, d, J=8.4 Hz), 5.93 (1H, d, J=11.2 Hz), 4.53 (1H, dd, J=11.2, 8.4 Hz), 4.33 (1H, dd, J=11.2, 5.6 Hz), 3.53 (1H, m), 3.19 (1H, dd, J=12.4, 11.6 Hz), 2.98 (3H, s) 2.01 (1H, s) ppm; 13C-NMR (75 MHz, CDCl₃) δ 166.2, 165.4, 159.6, 137.5, 137.0, 131.8, 131.3, 131.2, 131.0, 129.0, 128.7, 128.4, 128.2, 127.9, 127.8, 127.8, 127.8, 127.7, 127.7, 126.7, 126.5, 121.5, 110.1, 97.5, 89.3, 86.8, 62.9, 50.4, 48.4, 29.6 ppm; 8 HRMS (CI/NH$_3$) m/z calculated for C$_{38}$H$_{28}$Br$_2$O$_6$, 738.0253; found, 739.0217 (M+H).

Figure 21:
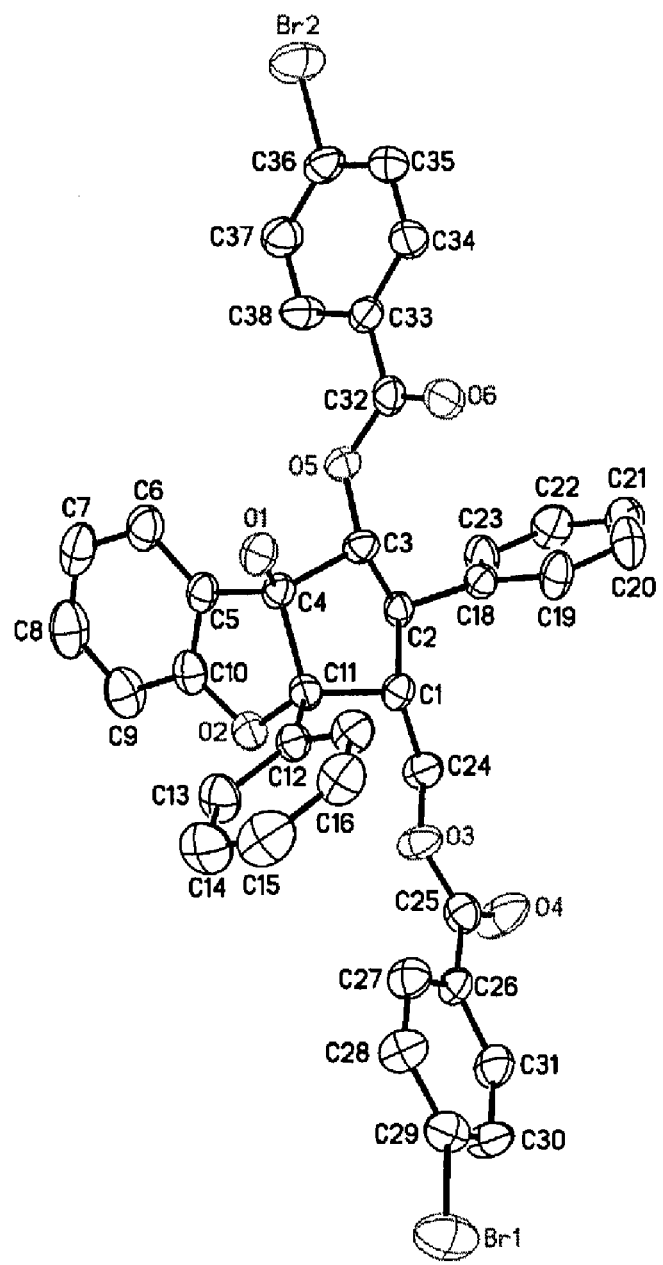
FIG. 21 shows the X-ray Crystal Structure of Compound 31.

The X-ray crystal structure of compound 31 is presented on FIG. 21. Crystals of compound 31 suitable for X-ray analysis were obtained by slow evaporation from benzene. Crystallographic data have been deposited with the Cambridge Crystallographic Data Centre (CCDC 248425).

Crystal data and structure refinement for compound 31 are presented in Table 7.

TABLE 7

Crystal data and structure refinement for compound 31.

| | |
|---|---|
| Identification code | Compound 31 |
| Empirical formula | C38 H28 Br2 O6 |
| Formula weight | 740.42 |
| Temperature | 295(2) K |
| Wavelength | 0.71073 Å |
| Crystal system | Monoclinic |
| Space group | P2(1)/c |
| Unit cell dimensions | a = 25.4111(10) Å   α = 90°. |
| | b = 16.5031(6) Å    β = 106.6770(10)°° |
| | c = 16.4599(6) Å    γ = 90° |
| Volume | 6612.3(4) Å$^3$ |
| Z | 8 |
| Density (calculated) | 1.488 Mg/m$^3$ |
| Absorption coefficient | 2.498 mm$^{-1}$ |
| F(000) | 2992 |
| Crystal size | 0.40 × 0.15 × 0.03 mm$^3$ |
| Theta range for data collection | 0.84 to 20.81° |
| Index ranges | −25 <= h <= 25, −13 <= k <= 16, |
| | −14 <= l <= 16 |
| Reflections collected | 23839 |
| Independent reflections | 6644 [R(int) = 0.0507] |
| Completeness to theta = 25.00° | 95.9% |
| Absorption correction | None |
| Refinement method | Semiempirical by SADABS |
| Data/restraints/parameters | 6644/0/829 |
| Goodness-of-fit on F$^2$ | 1.022 |
| Final R indices [I > 2sigma(I)] | R1 = 0.0940, wR2 = 0.1169 |
| R indices (all data) | R1 = 0.2038, wR2 = 0.1455 |
| Largest diff. peak and hole | 0.385 and −0.467 e · Å$^{-3}$ |

What is claimed is:

1. A method comprising:
   photochemically generating an oxidopyrylium species from a 3-hydroxychromone derivative; and
   performing a cycloaddition reaction between the oxidopyrylium species and a dipolarophile to form a cycloadduct.

2. The method of claim 1, wherein the oxidopyrylium species is generated via a process comprising an excited state intramolecular proton transfer.

3. The method of claim 1, wherein the oxidopyrylium species is photochemically generated from a 3-hydroxychromone derivative with the following chemical structure:

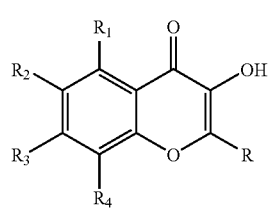

(I)

wherein R$_1$, R$_2$, R$_3$, R$_4$ and R are identical or different and selected from the group consisting of hydrogen, halogen, hydroxy, alkoxy, aryloxy, heteroalkoxy, heteroaryloxy, thioalkyl, thioaryl, acyl, aliphatic, alicyclic, heteroaliphatic, heterocyclic, aromatic, heteroaromatic, aryl, heteroaryl, alkylamino, amino alkyl, arylamino, amino aryl, a protecting group, —NO$_2$, —CN, —CF$_3$, —CH$_2$CF$_3$, —CHCl$_2$, —CH$_2$OH, —CH$_2$CH$_2$OH, —CH$_2$SO$_2$CH$_3$, —C(=O)R$_x$, —CO$_2$(R$_x$), —C(=O)N(R$_x$)$_2$, —OC(=O)N(R$_x$)$_2$, —OC(=O)R$_x$, —OCO$_2$R$_x$, —S(O)R$_x$, —S(O)$_2$R$_x$, —NR$_x$(CO)R$_x$, —N(R$_x$)CO$_2$R$_x$, —N(R$_x$)C(=O)N(R$_x$)$_2$, —N(R$_x$)S(O)$_2$R$_x$, and —S(O)$_2$N(R$_x$)$_2$, wherein each occurrence of R$_x$ is independently selected from the group consisting of hydrogen, aliphatic, alicyclic, heteroaliphatic, heterocyclic, aromatic, heteroaromatic, aryl, and heteroaryl.

4. The method of claim 1, wherein the oxidopyrylium species is photochemically generated from a 3-hydroxychromone derivative with the following chemical structure:

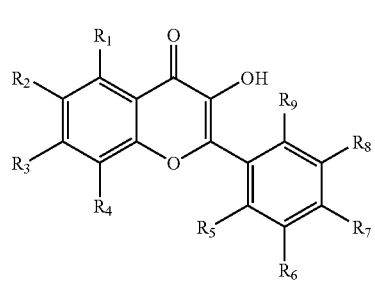

(II)

wherein R$_1$, R$_2$, R$_3$, R$_4$, R$_5$, R$_6$, R$_7$, R$_8$ and R$_9$ are identical or different and selected from the group consisting of hydrogen, halogen, hydroxy, alkoxy, aryloxy, heteroalkoxy, heteroaryloxy, thioalkyl, thioaryl, acyl, aliphatic, alicyclic, heteroaliphatic, heterocyclic, aromatic, heteroaromatic, aryl, heteroaryl, alkylamino, amino alkyl, arylamino, amino aryl, a protecting group, —NO$_2$, —CN, —CF$_3$, —CH$_2$CF$_3$, —CHCl$_2$, —CH$_2$OH, —CH$_2$CH$_2$OH, —CH$_2$SO$_2$CH$_3$, —C(=O)R$_x$, —CO$_2$(R$_x$), —C(=O)N(R$_x$)$_2$, —OC(=O)N(R$_x$)$_2$, —OC(=O)R$_x$, —OCO$_2$R$_x$, —S(O)R$_x$, —S(O)$_2$R$_x$, —NR$_x$(CO)R$_x$, —N(R$_x$)CO$_2$R$_x$, —N(R$_x$)C(=O)N(R$_x$)$_2$, —N(R$_x$)S(O)$_2$R$_x$, and —S(O)$_2$N(R$_x$)$_2$, wherein each occurrence of R$_x$ is independently selected from the group consisting of hydrogen, aliphatic, alicyclic, heteroaliphatic, heterocyclic, aromatic, heteroaromatic, aryl, and heteroaryl.

5. The method of claim 4, wherein the 3-hydroxychromone derivative has one of the following chemical structures:

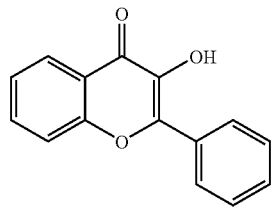

-continued

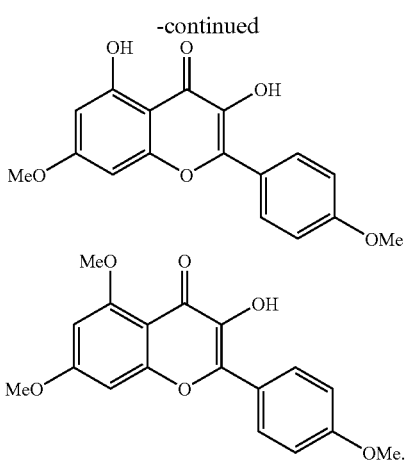

6. The method of claim 1, wherein the cycloaddition reaction comprises a 1,3-dipolar cycloaddition reaction.

7. The method of claim 1, further comprising converting the cycloadduct.

8. The method of claim 7, wherein the cycloadduct is converted into a compound selected from the group consisting of:

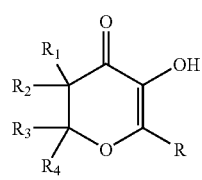
(III)

wherein:
R$_a$ is

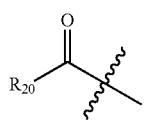

and R$_b$ is

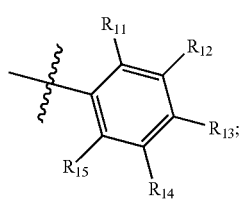

R$_{10}$ is selected from the group consisting of hydrogen, hydroxy, alkoxy, aryloxy, heteroalkoxy, heteroaryloxy, acyl, aliphatic, alicyclic, heteroaliphatic, heterocyclic, aromatic, heteroaromatic, aryl, heteroaryl, alkylamino, amino alkyl, arylamino, amino aryl, and a protecting group;

R' is selected from the group consisting of hydrogen, alkoxy, aryloxy, heteroalkoxy, heteroaryloxy, acyl, aliphatic, alicyclic, heteroaliphatic, heterocyclic, aromatic, heteroaromatic, aryl, heteroaryl, alkylamino, amino alkyl, arylamino, amino aryl, a protecting group, —CH$_2$OH, —CH$_2$CH$_2$OH, —CH$_2$SO$_2$CH$_3$, —C(=O)R$_x$, —CO$_2$(R$_x$), —C(=O)N(R$_x$)$_2$, —S(O)R$_x$, —NR$_x$(CO)R$_x$, —N(R$_x$)CO$_2$R$_x$, —N(R$_x$)C(=O)N(R$_x$)$_2$, and —N(R$_x$)S(O)$_2$R$_x$; and R$_1$, R$_2$, R$_3$, R$_4$, R, R'', R$_{11}$, R$_{12}$, R$_{13}$, R$_{14}$, and R$_{15}$ are identical or different and selected from the group consisting of hydrogen, halogen, hydroxy, alkoxy, aryloxy, heteroalkoxy, heteroaryloxy, thioalkyl, thioaryl, acyl, aliphatic, alicyclic, heteroaliphatic, heterocyclic, aromatic, heteroaromatic, aryl, heteroaryl, alkylamino, amino alkyl, arylamino, amino aryl, a protecting group, —NO$_2$, —CN, —CF$_3$, —CH$_2$CF$_3$, —CHCl$_2$, —CH$_2$OH, —CH$_2$CH$_2$OH, —CH$_2$SO$_2$CH$_3$, —C(=O)R$_x$, —CO$_2$(R$_x$), —C(=O)N(R$_x$)$_2$, —OC(=O)N(R$_x$)$_2$, —OC(=O)R$_x$, —OCO$_2$R$_x$, —S(O)R$_x$, —S(O)$_2$R$_x$, —NR$_x$(CO)R$_x$, —N(R)OCO$_2$R$_x$, —N(R$_x$)C(=O)N(R$_x$)$_2$, —N(R$_x$)S(O)$_2$R$_x$, and —S(O)$_2$N(R$_x$)$_2$;

wherein each occurrence of R$_x$ is independently selected from the group consisting of hydrogen, aliphatic, alicyclic, heteroaliphatic, heterocyclic, aromatic, heteroaromatic, aryl, and heteroaryl.

9. The method of claim 3 or 4, wherein:
the dipolarophile is of formula (IV):

(R$_a$)HC=CH(R$_b$)                                      (IV);

and the cycloadduct is of formula (V) or (V'):

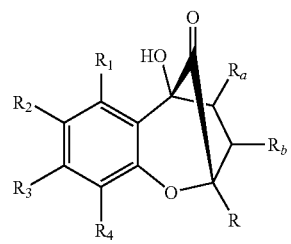
(V)

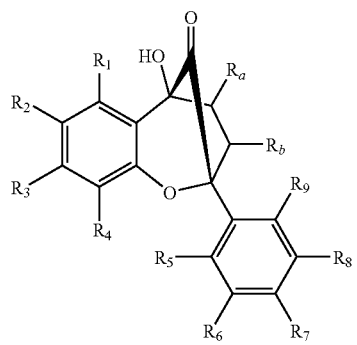
(V')

wherein:
R$_a$ is

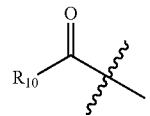

and $R_b$ is

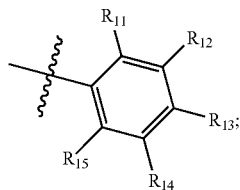

$R_{10}$ is selected from the group consisting of hydrogen, hydroxy, alkoxy, aryloxy, heteroalkoxy, heteroaryloxy, acyl, aliphatic, alicyclic, heteroaliphatic, heterocyclic, aromatic, heteroaromatic, aryl, heteroaryl, alkylamino, amino alkyl, arylamino, amino aryl, and a protecting group; and $R_{11}$, $R_{12}$, $R_{13}$, $R_{14}$, and $R_{15}$ are identical or different and selected from the group consisting of hydrogen, halogen, hydroxy, alkoxy, aryloxy, heteroalkoxy, heteroaryloxy, thioalkyl, thioaryl, acyl, aliphatic, alicyclic, heteroaliphatic, heterocyclic, aromatic, heteroaromatic, aryl, heteroaryl, alkylamino, amino alkyl, arylamino, amino aryl, a protecting group, $-NO_2$, $-CN$, $-CF_3$, $-CH_2CF_3$, $-CHCl_2$, $-CH_2OH$, $-CH_2CH_2OH$, $-CH_2SO_2CH_3$, $-C(=O)R_x$, $-CO_2(R_x)$, $-C(=O)N(R_x)_2$, $-OC(=O)N(R_x)_2$, $-OC(=O)R_x$, $-OCO_2R_x$, $-S(O)R_x$, $-S(O)_2R_x$, $-NR_x(CO)R_x$, $-N(R_x)CO_2R_x$, $-N(R_x)C(=O)N(R_x)_2$, $-N(R_x)S(O)_2R_x$, and $-S(O)_2N(R_x)_2$, wherein each occurrence of $R_x$ is independently selected from the group consisting of hydrogen, aliphatic, alicyclic, heteroaliphatic, heterocyclic, aromatic, heteroaromatic, aryl, and heteroaryl.

10. The method of claim 9, wherein the 3-hydroxychromone derivative has one of the following chemical structures:

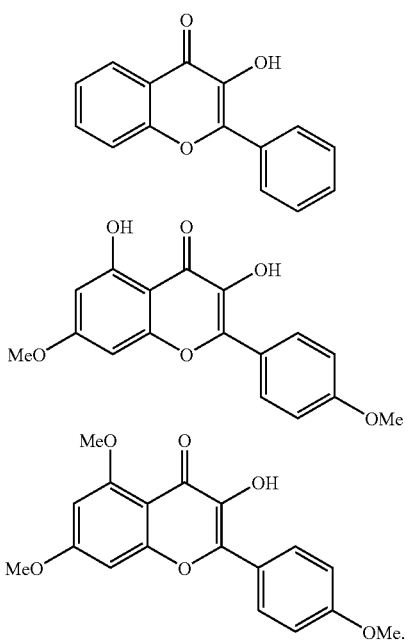

11. The method of claim 9, further comprising converting the compound of formula (V) into a compound of formula (VI):

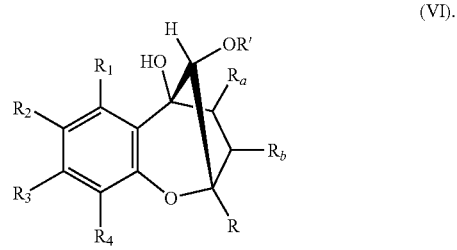

wherein R' is selected from the group consisting of hydrogen, alkoxy, aryloxy, heteroalkoxy, heteroaryloxy, acyl, aliphatic, alicyclic, heteroaliphatic, heterocyclic, aromatic, heteroaromatic, aryl, heteroaryl, alkylamino, amino alkyl, arylamino, amino aryl, a protecting group, $-CH_2OH$, $-CH_2CH_2OH$, $-CH_2SO_2CH_3$, $-C(=O)R_x$, $-CO_2(R_x)$, $-C(=O)N(R_x)_2$, $-S(O)R_x$, $-NR_x(CO)R_x$, $-N(R_x)CO_2R_x$, $-N(R_x)C(=O)N(R_x)_2$, and $-N(R_x)S(O)_2R_x$, wherein each occurrence of $R_x$ is independently selected from the group consisting of hydrogen, aliphatic, alicyclic, heteroaliphatic, heterocyclic, aromatic, heteroaromatic, aryl, and heteroaryl.

12. The method of claim 9, further comprising converting the compound of formula (V') into a compound of formula (VI'):

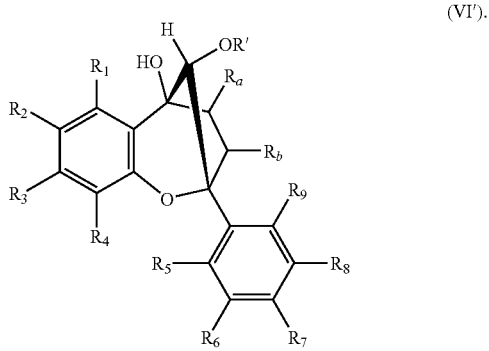

wherein R' is selected from the group consisting of hydrogen, alkoxy, aryloxy, heteroalkoxy, heteroaryloxy, acyl, aliphatic, alicyclic, heteroaliphatic, heterocyclic, aromatic, heteroaromatic, aryl, heteroaryl, alkylamino, amino alkyl, arylamino, amino aryl, a protecting group, $-CH_2OH$, $-CH_2CH_2OH$, $-CH_2SO_2CH_3$, $-C(=O)R_x$, $-CO_2(R_x)$, $-C(=O)N(R_x)_2$, $-S(O)R_x$, $-NR_x(CO)R_x$, $-N(R_x)CO_2R_x$, $-N(R_x)C(=O)N(R_x)_2$, and $-N(R_x)S(O)_2R_x$, wherein each occurrence of $R_x$ is independently selected from the group consisting of hydrogen, aliphatic, alicyclic, heteroaliphatic, heterocyclic, aromatic, heteroaromatic, aryl, and heteroaryl.

13. The method of claim 12, wherein the 3-hydroxychromone derivative has one of the following chemical structures:

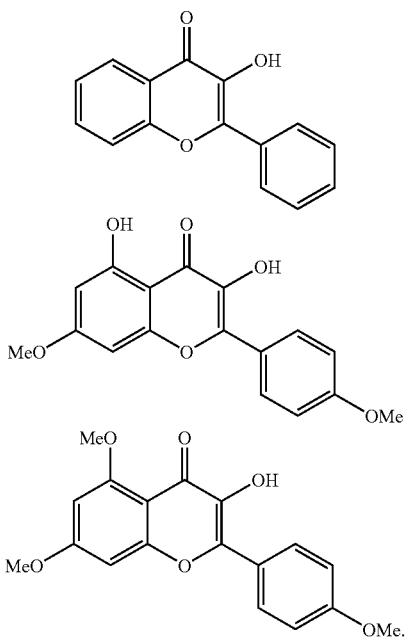

14. The method of claim 11 or 12, wherein converting the compound of formula (V) or (V') into a compound of (VI) or (VI') comprises a reduction.

15. The method of claim 14, wherein the reduction comprises using NaBH₄ or Me₄NBH(OAc)₃.

16. The method of claim 11 or 12, wherein converting the compound of formula (V) or (V') into a compound of (VI) or (VI') comprises addition of a nucleophile.

17. The method of claim 9, further comprising converting the compound of formula (V) into a compound of formula (VII):

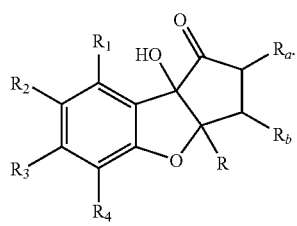

18. The method of claim 9, further comprising converting the compound of formula (V') into a compound of formula (VII'):

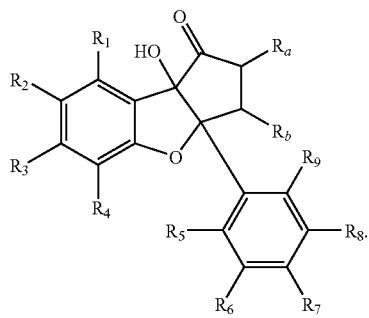

19. The method of claim 18, wherein the 3-hydroxychromone derivative has one of the following chemical structures:

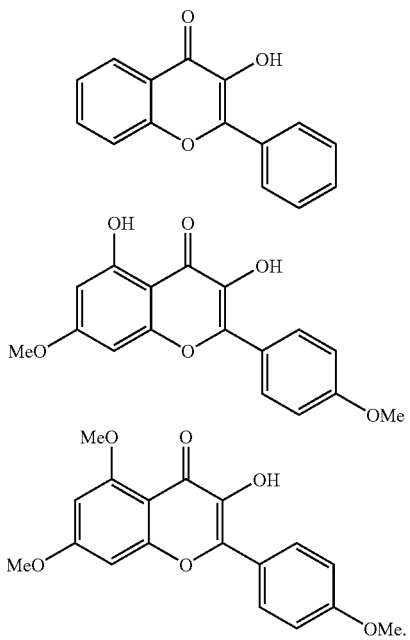

20. The method of claim 17 or 18, wherein converting the compound of formula (V) or (V') into a compound of formula (VII) or (VII') comprises an α-ketol (acyloin) rearrangement and, optionally, a hydroxyl-directed reduction.

21. The method of claim 20, wherein the α-ketol (acyloin) rearrangement comprises a base-mediated reaction.

22. The method of claim 9, further comprising converting the compound of formula (V) into a compound of formula (VIII):

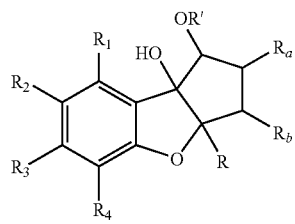

wherein R' is selected from the group consisting of hydrogen, alkoxy, aryloxy, heteroalkoxy, heteroaryloxy, acyl, aliphatic, alicyclic, heteroaliphatic, heterocyclic, aromatic, heteroaromatic, aryl, heteroaryl, alkylamino, amino alkyl, arylamino, amino aryl, a protecting group, —CH₂OH, —CH₂CH₂OH, —CH₂SO₂CH₃, —C(=O)R$_x$, —CO₂(R$_x$), —C(=O)N(R$_x$)₂, —S(O)R$_x$, —NR$_x$(CO)R$_x$, —N(R$_x$)CO₂R$_x$, —N(R$_x$)C(=O)N(R$_x$)₂, and —N(R$_x$)S(O)₂R$_x$, wherein each occurrence of R$_x$ is independently selected from the group consisting of hydrogen, aliphatic, alicyclic, heteroaliphatic, heterocyclic, aromatic, heteroaromatic, aryl, and heteroaryl.

23. The method of claim 9, further comprising converting the compound of formula (V') into a compound of formula (VIII'):

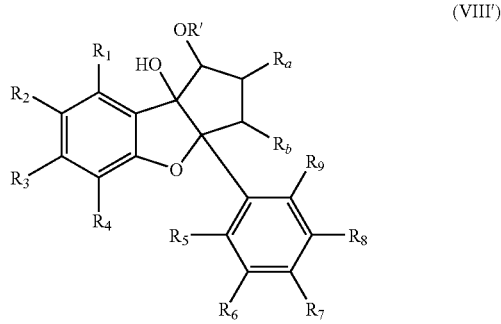

(VIII')

wherein R' is selected from the group consisting of hydrogen, alkoxy, aryloxy, heteroalkoxy, heteroaryloxy, acyl, aliphatic, alicyclic, heteroaliphatic, heterocyclic, aromatic, heteroaromatic, aryl, heteroaryl, alkylamino, amino alkyl, arylamino, amino aryl, a protecting group, —CH$_2$OH, —CH$_2$CH$_2$OH, —CH$_2$SO$_2$CH$_3$, —C(=O) R$_x$, —CO$_2$(R$_x$), —C(=O)N(R$_x$)$_2$, —S(O)R$_x$, —NR$_x$(CO)R$_x$, —N(R$_x$)CO$_2$R$_x$, —N(R$_x$)C(=O)N(R$_x$)$_2$, and —N(R$_x$)S(O)$_2$R$_x$, wherein each occurrence of R$_x$ is independently selected from the group consisting of hydrogen, aliphatic, alicyclic, heteroaliphatic, heterocyclic, aromatic, heteroaromatic, aryl, and heteroaryl.

24. The method of claim 23, wherein the 3-hydroxychromone derivative has one of the following chemical structures:

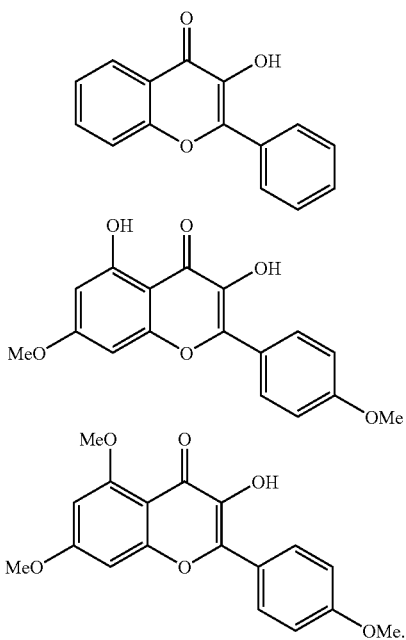

25. The method of claim 22 or 23, wherein converting the compound of formula (V) or (V') into a compound of formula (VIII) or (VIII') comprises an α-ketol (acyloin) rearrangement and, optionally, a hydroxyl-directed reduction.

26. The method of claim 25, wherein the α-ketol (acyloin) rearrangement comprises a base-mediated reaction.

27. The method of claim 9, further comprising converting the compound of formula (V) into a compound of formula (IX):

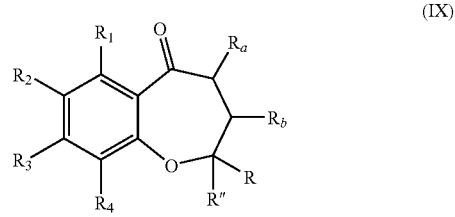

(IX)

wherein R'' is selected from the group consisting of hydrogen, halogen, hydroxy, alkoxy, aryloxy, heteroalkoxy, heteroaryloxy, thioalkyl, thioaryl, acyl, aliphatic, alicyclic, heteroaliphatic, heterocyclic, aromatic, heteroaromatic, aryl, heteroaryl, alkylamino, amino alkyl, arylamino, amino aryl, a protecting group, —NO$_2$, —CN, —CF$_3$, —CH$_2$CF$_3$, —CHCl$_2$, —CH$_2$OH, —CH$_2$CH$_2$OH, —CH$_2$SO$_2$CH$_3$, —C(=O)R$_x$, —CO$_2$ (R$_x$), —C(=O)N(R$_x$)$_2$, —OC(=O)N(R$_x$)$_2$, —OC(=O)R$_x$, —OCO$_2$R$_x$, —S(O)R$_x$, —S(O)$_2$R$_x$, —NR$_x$(CO)R$_x$, —N(R$_x$)CO$_2$R$_x$, —N(R$_x$)C(=O)N(R$_x$)$_2$, —N(R$_x$)S(O)$_2$R$_x$, and —S(O)$_2$N(R$_x$)$_2$, wherein each occurrence of R$_x$ is independently selected from the group consisting of hydrogen, aliphatic, alicyclic, heteroaliphatic, heterocyclic, aromatic, heteroaromatic, aryl, and heteroaryl.

28. The method of claim 9, further comprising converting the compound of formula (V') into a compound of formula (IX'):

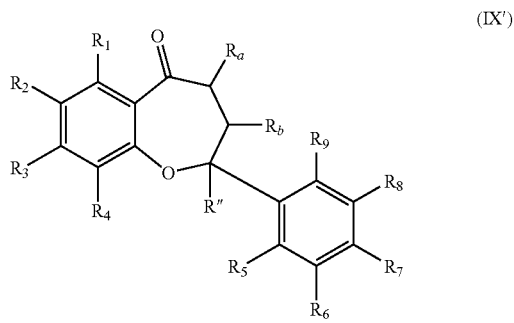

(IX')

wherein R'' is selected from the group consisting of hydrogen, halogen, hydroxy, alkoxy, aryloxy, heteroalkoxy, heteroaryloxy, thioalkyl, thioaryl, acyl, aliphatic, alicyclic, heteroaliphatic, heterocyclic, aromatic, heteroaromatic, aryl, heteroaryl, alkylamino, amino alkyl, arylamino, amino aryl, a protecting group, —NO$_2$, —CN, —CF$_3$, —CH$_2$CF$_3$, —CHCl$_2$, —CH$_2$OH, —CH$_2$CH$_2$OH, —CH$_2$SO$_2$CH$_3$, —C(=O)R$_x$, —CO$_2$ (R$_x$), —C(=O)N(R$_x$)$_2$, —OC(=O)N(R$_x$)$_2$, —OC(=O)R$_x$, —OCO$_2$R$_x$, —S(O)R$_x$, —S(O)$_2$R$_x$, —NR$_x$(CO)R$_x$, —N(R$_x$)CO$_2$R$_x$, —N(R$_x$)C(=O)N(R$_x$)$_2$, —N(R$_x$)S(O)$_2$R$_x$, and —S(O)$_2$N(R$_x$)$_2$, wherein each occurrence of R$_x$ is independently selected from the group consisting of hydrogen, aliphatic, alicyclic, heteroaliphatic, heterocyclic, aromatic, heteroaromatic, aryl, and heteroaryl.

29. The method of claim 28, wherein the 3-hydroxy-chromone derivative has one of the following chemical structures:
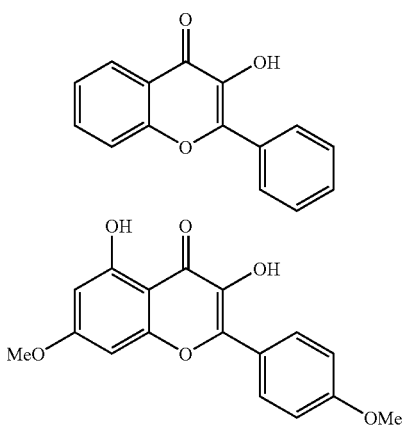
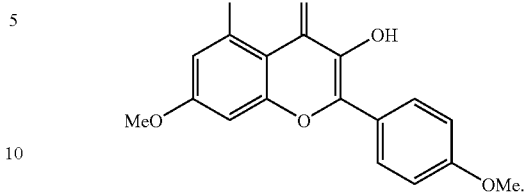
30. The method of claim 27 or 28, wherein converting the compound of formula (V) or (V') into a compound of formula (IX) or (IX') comprises an oxidative cleavage.
31. The method of claim 30, wherein the oxidative cleavage comprises using Pb(OAc)$_4$.
* * * * *